US006958336B2

(12) United States Patent
Barrish et al.

(10) Patent No.: US 6,958,336 B2
(45) Date of Patent: Oct. 25, 2005

(54) THIAZOLYL INHIBITORS OF TEC FAMILY TYROSINE KINASES

(75) Inventors: Joel C. Barrish, Richboro, PA (US); Jagabandhu Das, Mercerville, NJ (US); Steven B. Kanner, Princeton, NJ (US); Chunjian Liu, Pennington, NJ (US); Steven H. Spergel, Warrington, PA (US); John Wityak, Robbinsville, NJ (US); Arthur M. P. Doweyko, Long Valley, NJ (US); Joseph A. Furch, III, Lawrenceville, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/641,933

(22) Filed: Aug. 15, 2003

(65) Prior Publication Data

US 2004/0067990 A1 Apr. 8, 2004

Related U.S. Application Data

(62) Division of application No. 10/027,982, filed on Dec. 20, 2001, now Pat. No. 6,706,717.
(60) Provisional application No. 60/257,830, filed on Dec. 21, 2000.

(51) Int. Cl.$^7$ .................. A61K 31/496; C07D 417/10; C07D 417/12
(52) U.S. Cl. .................. 514/252.19; 544/367
(58) Field of Search .............. 514/252.19; 544/367

(56) References Cited

U.S. PATENT DOCUMENTS 6,040,321 A 3/2000 Kim et al.
6,114,365 A 9/2000 Pevarello et al.
6,262,096 B1 7/2001 Kim et al.

FOREIGN PATENT DOCUMENTS

| | | |
|---|---|---|
| EP | 0117082 | 1/1984 |
| EP | 0412404 | 7/1990 |
| EP | 0928790 | 12/1998 |
| EP | 0928793 | 12/1998 |
| WO | WO99/00357 | 1/1999 |
| WO | WO99/65884 | 12/1999 |
| WO | WO00/28710 | 1/2000 |
| WO | WO00/17175 | 3/2000 |
| WO | WO00/24724 | 5/2000 |
| WO | WO00/26202 | 5/2000 |
| WO | WO00/26203 | 5/2000 |
| WO | WO00/39101 | 7/2000 |
| WO | WO 00/62778 | 10/2000 |
| WO | WO00/75120 | 12/2000 |
| WO | WO01/10865 | 2/2001 |
| WO | WO01/17995 | 3/2001 |
| WO | WO01/35959 | 5/2001 |
| WO | WO01/64653 | 9/2001 |
| WO | WO01/64654 | 9/2001 |
| WO | WO01/64655 | 9/2001 |

OTHER PUBLICATIONS

Cancer and Metastasis Reviews (1998), 17(1), 91–106.*
Science (1999), vol. 286, 531–537.*

* cited by examiner

Primary Examiner—Kamal A. Saeed
Assistant Examiner—Rebecca Anderson
(74) Attorney, Agent, or Firm—Terence J. Bogie

(57) ABSTRACT

Novel thiazolyl compounds and salts thereof, pharmaceutical compositions containing such compounds, and methods of using such compounds in the treatment of Tec family tyrosine kinase-associated disorders such as cancer, immunologic disorders and allergic disorders.

17 Claims, No Drawings

THIAZOLYL INHIBITORS OF TEC FAMILY TYROSINE KINASES

This application is a Divisional Application of prior application Ser. No. 10/027,982 filed on Dec. 20, 2001, now U.S. Pat. No. 6,706,717, which claims priority to U.S. Provisional Application Ser. No. 60/257,830 filed Dec. 21, 2000, the entirety of which is incorporated herein by reference.

FIELD OF THE INVENTION

The present invention provides for thiazolyl compounds useful as inhibitors of Tec family tyrosine kinases (especially inhibitors of Emt) and to pharmaceutical compositions containing such compounds. The present invention further provides for methods of using such compounds as immunosuppressive, anti-inflammatory, anti-allergic, and anti-cancer agents.

BACKGROUND OF THE INVENTION

The present invention relates to inhibitors of the Tec family tyrosine kinases, and particularly, inhibitors of Emt. The Tec family kinases include Emt [expressed mainly in T cells; Gibson, S. et al., Blood 82, 1561–1572 (1993)], Txk [T-cell expressed kinase; Haire, R. N. et al., Hum. Mol. Genet. 3, 897–901 (1994)], Tec [tyrosine kinase expressed in hepatocellular carcinoma cells; Mano et al., Oncogene 5, 1781–1786 (1990)], Btk [Bruton's tyrosine kinase; Vetrie, D. et al., Nature 361, 226–233, (1993)], and Bmx [bone marrow kinase, X-linked; Tamagnon, L. et al., Oncogene 9, 3683–3688 (1994)].

Mammalian immunity relies on the activation of T cells upon antigen presentation. The molecular mechanisms of T cell activation are initiated by the sequential activation of three distinct classes of non-receptor protein tyrosine kinases (PTK) following the engagement of the T cell antigen receptor (TCR). These three classes of PTK are the Src family kinases (Lck and Lyn), the Syk family kinases (ZAP-70 and Syk), and the Tec family kinases (Emt, Txk, and Tec). Inhibition of one or more of these kinases will impede the initiation signals and block T cell activation following antigen presentation. Thus, small molecular weight inhibitors of these kinases can be applied to treat the diseases that are associated with unwanted T cell activation.

Emt, also known as Itk (Interleukin-2-inducible T cell kinases) or Tsk (T-cell-specific tyrosine kinase), is expressed solely in T, natural killer, and mast cells. Emt is tyrosine-phosphorylated and activated in response to cross-linking of TCR, CD28, or CD2; and has been implicated in thymocyte development and the activation of T cells through TCR and CD28 engagement. Inside the cells, Emt is regulated by membrane recruitment followed by Lck phosphorylation and autophosphorylation. Emt is recruited to the membrane rafts for Lck phosphorylation through the interaction between the pleckstrin homology (PH) domain of Emt and the membrane lipid, phosphotidylinositol (3,4,5)-triphosphate [Bunnell et al., J. Biol. Chem. 275, 2219–2230 (2000)].

Gene knockout studies reveal that mice lacking Emt have decreased numbers of mature thymocyte, especially CD4+ T cells. The T cells isolated from such mice are compromised in their proliferative response to allogeneic MHC stimulation, and to anti-TCR/CD3 cross-linking [Liao X. C. and Littman, D. R., Immunity 3, 757–769 (1995)]. These T cells also exhibit defective PLCγ1 tyrosine phosphorylation, inositol triphosphate production, $Ca^{2+}$ mobilization, and cytokine production (such as IL-2 and IFNγ) in response to TCR cross-linking [Schaeffer, E. M. et al., Science 284, 638–641 (1999)]. This genetic evidence indicates that Emt activity plays a requisite role in TCR signal transduction; and selective inhibition of Emt should have immunosuppressive, anti-inflammatory, and anti-proliferative effects. In addition, Emt-deficient mice are unable to establish functional Th2 cells (the IL-4 producing cells) and such mice are unable to clear parasitic infections depending upon a Th2 response [Fowell, D. J. et al., Immunity 11, 399–409 (1999)]. This observation also suggests that Emt may be an attractive target for modulating dysregulated allergic pathways mediated by Th2 cells.

SUMMARY OF THE INVENTION

The present invention provides thiazolyl compounds of the following formula I and salts thereof for use as Emt tyrosine kinase inhibitors:

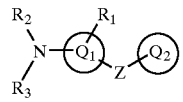

I where $Q_1$ is thiazolyl;

$Q_2$ is aryl or heteroaryl optionally independently substituted with one or more (preferably one to three) substituents $R_{1a}$;

Z is (1) —O—,
(2) —S—,
(3) —$NR_4$—,
(4) —$CR_4R_5$—,
(5) —$CR_4R_5$—O—$CR_{4a}R_{5a}$—,
(6) —$CR_4R_5$—$NR_{4b}$—$CR_{4a}R_{5a}$—,
(7) —$CR_4R_5$—S—$CR_{4a}R_{5a}$—,
(8) —$CR_4R_5$—O—,
(9) —O—$CR_4R_5$—,
(10) —$CR_4R_5$—$NR_{4b}$—,
(11) —$NR_{4b}$—$CR_4R_5$—,
(12) —$CR_4R_5$—S—,
(13) —S—$CR_4R_5$—,
(14) —$S(O)_q$— where q is 1 or 2,
(15) —$CR_4R_5$—$S(O)_q$—, or
(16) —$S(O)_q$—$CR_4R_5$—;

$R_1$ and $R_{1a}$ are independently (1) hydrogen or $R_6$,
(2) —OH or —$OR_6$,
(3) —SH or —$SR_6$,
(4) —$C(O)_qH$, —$C(O)_qR_6$, or —O—$C(O)_qR_6$,
(5) —$SO_3H$ or —$S(O)_qR_6$,
(6) halo,
(7) cyano,
(8) nitro,
(9) -$Z_4$-$NR_7R_8$,
(10) -$Z_4$-$N(R_9)$-$Z_5$-$NR_{10}R_{11}$,
(11) -$Z_4$-$N(R_{12})$-$Z_5$-$R_6$, or
(12) —$P(O)(OR_6)_2$;

$R_2$ and $R_3$ are each independently H, -$Z_4$-$R_{6a}$, or -$Z_4$-$NR_{7a}R_{8a}$ $R_4$, $R_{4a}$, $R_{4b}$, $R_5$ and $R_{5a}$, are each independently hydrogen, alkyl, aryl, aralkyl, cycloalkyl, or heteroarylalkyl;

$R_6$, $R_{6a}$, $R_{6b}$ and $R_{6c}$ are independently alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$, $R_7$, $R_{7a}$, $R_8$, $R_{8a}$, $R_9$, $R_{10}$, $R_{11}$ and $R_{12}$ (1) are each independently hydrogen, or -$Z_4R_{6b}$; or (2) $R_7$ and $R_8$ or $R_{7a}$ and $R_{8a}$ may together be alkylene, alkenylene, or heteroalkylene, completing a 3- to 8-membered saturated or unsaturated ring with the nitrogen atom to which they are attached, which ring is unsubstituted or substituted with $Z_1$, $Z_2$ and one or more groups $Z_3$, or (3) any two of $R_9$, $R_{10}$ and $R_{11}$ may together be alkylene, alkenylene or heteroalkylene completing a 3- to 8-membered saturated or unsaturated ring together with the nitrogen atoms to which they are attached, which ring is unsubstituted or substituted with one or more $Z_1$, $Z_2$ and $Z_3$;

$Z_1$, $Z_2$ and $Z_3$ are each independently (1) hydrogen or $Z_6$, (2) —OH or —$OZ_6$, (3) —SH or —$SZ_6$, (4) —C(O)$_q$H, —C(O)$_q Z_6$, or —O—C(O)$_q Z_6$, (5) —$SO_3H$, —S(O)$_q Z_6$, or S(O)$_q$N($Z_9$)$Z_6$, (6) halo, (7) cyano, (8) nitro, (9) -$Z_4$-N$Z_7Z_8$,

(10) -$Z_4$-N($Z_9$)-$Z_5$-N$Z_7Z_8$,

(11) -$Z_4$-N($Z_{10}$)-$Z_5$-$Z_6$,

(12) -$Z_4$-N($Z_{10}$)-$Z_5$-H,

(13) oxo,

(14) any two of $Z_1$, $Z_2$, and $Z_3$ on a given substituent may together be alkylene or alkenylene completing a 3- to 8-membered saturated or unsaturated ring together with the atoms to which they are attached; or

(15) any two of $Z_1$, $Z_2$, and $Z_3$ on a given substituent may together be —O—CH$_2$)$_q$—O—;

$Z_4$ and $Z_5$ are each independently (1) a single bond, (2) -$Z_{11}$-S(O)$_q$-$Z_{12}$-, (3) -$Z_{11}$-C(O)-$Z_{12}$-, (4) -$Z_{11}$-C(S)-$Z_{12}$-, (5) -$Z_{11}$-O-$Z_{12}$-, (6) -$Z_{11}$-S-$Z_{12}$-, (7) -$Z_{11}$-O—C(O)-$Z_{12}$-, (8) -$Z_{11}$-C(O)—O-$Z_{12}$-; or (9) alkyl $Z_6$ and $Z_{6a}$ are independently (i) alkyl, hydroxyalkyl, alkoxyalkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl;

(ii) a group (i) which is itself substituted by one or more of the same or different groups (i); or (iii) a group (i) or (ii) which is independently substituted by one or more (preferably 1 to 3) of the groups (2) to (15) of the definition of $Z_1$;

$Z_7$, $Z_8$, $Z_9$ and $Z_{10}$ (1) are each independently hydrogen or -$Z_4$-$Z_{6a}$;

(2) $Z_7$ and $Z_8$ may together be alkylene, alkenylene, or heteroalkylene completing a 3- to 8-membered saturated or unsaturated ring together with the atoms to which they are attached, which ring is unsubstituted or substituted with one or more $Z_1$, $Z_2$ and $Z_3$, or (3) $Z_7$ or $Z_8$, together with $Z_9$, may be alkylene, alkenylene, or heteroalkylene completing a 3- to 8-membered saturated or unsaturated ring together with the nitrogen atoms to which they are attached, which ring is unsubstituted or substituted with one or more $Z_1$, $Z_2$ and $Z_3$;

$Z_{11}$ and $Z_{12}$ are each independently (1) a single bond, (2) alkylene, (3) alkenylene, or (4) alkynylene.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The term "heteroalkylene" refers to alkylene or alkenylene groups containing one or more heteroatoms N, O or S.

The terms "ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

The terms "cycloalkyl" refers to saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

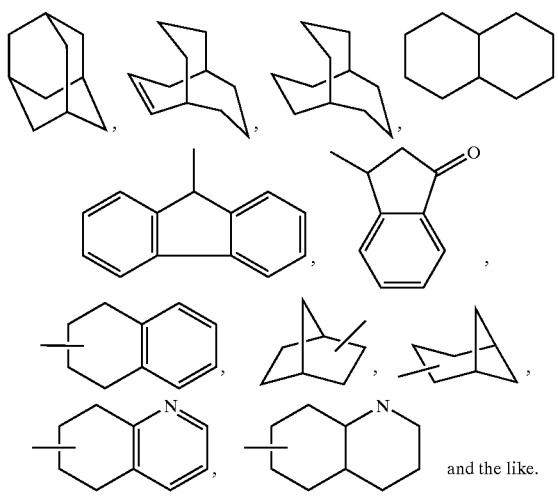

and the like.

The terms "halogen" and "halo" refer to fluorine, chlorine, bromine and iodine.

The terms "heterocycle", "heterocyclic" or "heterocyclo" refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, 5-tetrazolyl,

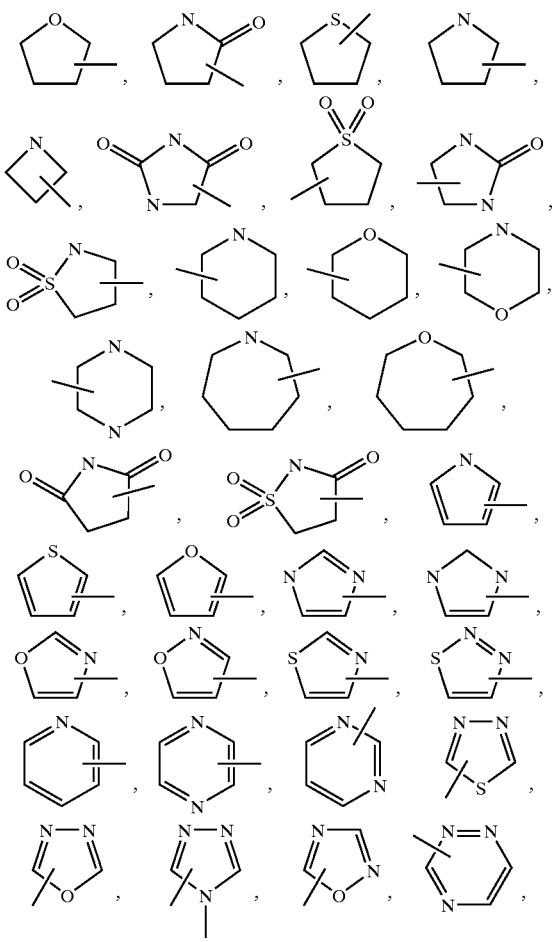

and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl

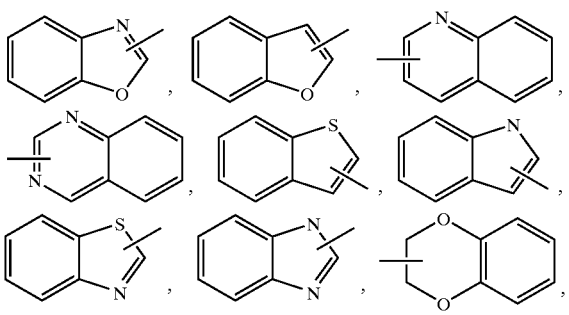

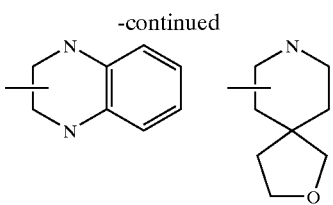

and the like.

Exemplary tricyclic heterocyclic groups include carbazolyl, benzidolyl, phenanthrolinyl, acridinyl, phenanthridinyl, xanthenyl and the like.

The term "heteroaryl" refers to a 5- or 6-membered aromatic ring which includes 1, 2, 3 or 4 hetero atoms such as nitrogen, oxygen or sulfur, and such rings fused to an aryl, cycloalkyl, or heterocyclo ring (e.g. benzothiophenyl, indolyl), and includes possible N-oxides, such as

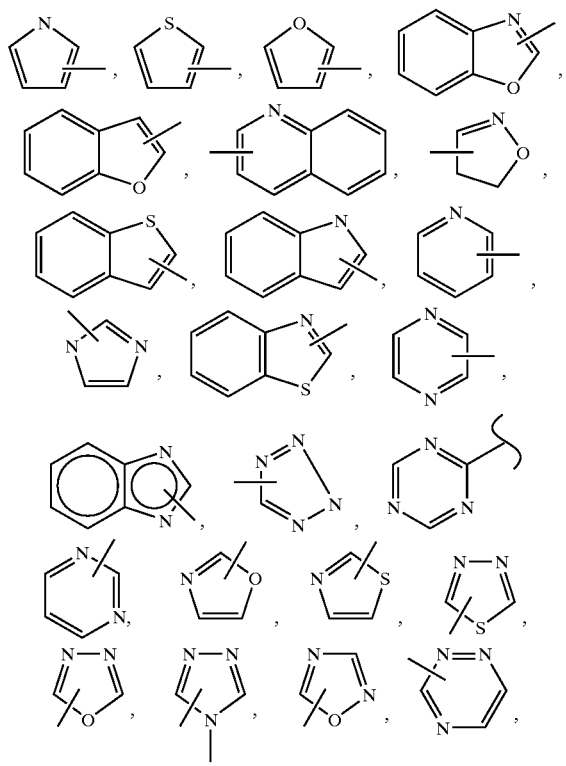

and the like.

Where q is 1 or 2, "—C(O)$_q$H" denotes —C(O)—H or —C(O)—OH; "—C(O)$_q$R$_6$" or "—C(O)$_q$Z$_6$" denote, respectively, —C(O)—R$_6$ or —C(O)—OR$_6$, or —C(O)-Z$_6$ or —C(O)—OZ$_6$; "—O—C(O)$_q$R$_6$" or "—O—C(O)$_q$Z$_6$" denote, respectively, —O—C(O)—R$_6$ or —O—C(O)—OR$_6$, or —O—C(O)—Z$_6$ or —O—C(O)—OZ$_6$; and "—S(O)$_q$R$_6$" or "—S(O)$_q$Z$_6$" denote, respectively, —SO—R$_6$ or —SO$_2$—R$_6$, or —SO—Z$_6$ or —SO$_2$—Z$_6$.

Compounds of the formula I may in some cases form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

Preferred compounds within the scope of the formula I include those wherein:

$Q_2$ is phenyl optionally substituted with one or more groups as defined in $R_{1a}$ (especially, alkyl, hydroxy, alkoxy, haloalkoxy, halo, nitro, —C(O)$_q$R$_6$, —C(O)$_q$H, -Z$_4$-NR$_7$R$_8$, -Z$_4$-N(R$_{12}$)-Z$_5$-Z$_6$, or -Z$_4$-N(R$_9$)-Z$_5$-NR$_{10}$R$_{11}$);

Z is selected from —S—, —CR$_4$R$_5$—S—, —S—CR$_4$R$_5$—, —CR$_4$R$_5$—O—CR$_{4a}$R$_{5a}$—, —CR$_4$R$_5$—NR$^4$—CR$_{4a}$R$_{5a}$—, —CR$_4$R$_5$—, —CR$_4$R$_5$—SO$_2$—or —CR$_4$R$_5$—S(O)—;

R$_1$ is hydrogen;
R$_2$ is hydrogen or alkyl; and
R$_3$ is H, -Z or -Z$_4$NR$_{7a}$R$_{8a}$.

More preferred compounds within the scope of formula I include those wherein:

$Q_2$ is phenyl optionally substituted with one or more groups selected from alkyl, alkoxy, hydroxy, —C(O)R$_6$ (especially wherein R$_6$ is optionally substituted alkyl or heterocyclo (especially piperazinyl), —C(O)NR$_7$R$_8$ or —NR$_7$R$_8$;

Z is selected from —CR$_4$R$_5$—O—CR$_{4a}$R$_{5a}$—, —S—, —CR$_4$R$_5$—S— or —S—CR$_4$R$_5$—;

R$_1$ is hydrogen;
R$_2$ is hydrogen or alkyl; and
R$_3$ is -Z$_4$R$_{6a}$, especially where:

(a) Z$_4$ is a single bond and R$_{6a}$ is optionally substituted heteroaryl (preferably pyridinyl, pyrimidinyl, or quinolinyl optionally substituted with one or more Z$_1$, Z$_2$ or Z$_3$ which are preferably alkyl, hydroxyalkyl, halo, -Z$_4$-NZ$_7$Z$_8$, —C(O)$_q$H, —C(O)$_q$Z$_6$, —OZ$_6$ or heterocyclo)

(b) Z$_4$ is —C(O)— and R$_{6a}$ is
(1) aryl (especially phenyl) optionally substituted with one or more Z$_1$, Z$_2$ or Z$_3$ (preferably -Z$_4$-NZ$_7$Z$_8$, —OZ$_a$, hydroxy, heterocyclo, or alkyl which may be optionally substituted with any of the preceding preferred Z$_1$, Z$_2$ or Z$_3$ groups) (where present, at least one substituent is preferably in the para position);
(2) alkyl optionally substituted with one or more Z$_1$, Z$_2$ or Z$_3$;
(3) cycloalkyl (especially cyclopropyl) optionally substituted with one or more Z$_1$, Z$_2$ or Z$_3$ (especially aryl, aralkyl, halo, hydroxy, —C(O)$_q$H, —C(O)$_q$Z$_6$ or alkyl optionally substituted with hydroxy, —OZ$_6$ or -Z$_4$-NZ$_7$Z$_8$)); or
(4) heterocyclo (especially pyrrolidinyl, piperidyl, piperidenyl, piperazinyl, pyrrolyl, imidazolyl, pyrazolyl, pyridinyl or pyrimidinyl) optionally substituted with one or more Z$_1$, Z$_2$ or Z$_3$ (especially -Z$_4$-NZ$_7$Z$_8$, —C(O)$_q$H, —C(O)$_q$Z$_6$, or alkyl optionally substituted with hydroxy, —OZ$_6$ or -Z$_4$-NZ$_7$Z$_8$); or (c) Z$_4$ is —C(O)—O— and R$_{6a}$ is alkyl, cycloalkyl, aryl or aralkyl, any of which may be optionally substituted with one or more Z$_1$, Z$_2$ or Z$_3$.

Preferred compounds within the scope of formula I include compounds of the following formula II:

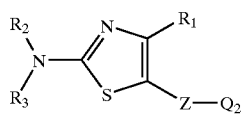

II where Z, Q$_2$, R$_1$, R$_2$ and R$_3$ are as described above (including the description of preferred substituents). Additionally, preferred compounds within the scope of formula II include compounds of the following formulae IIIa, IIIb and IIIc:

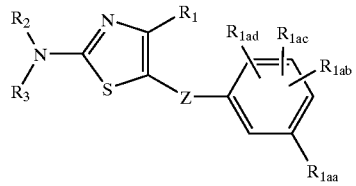

IIIa

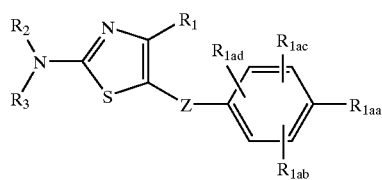

IIIb

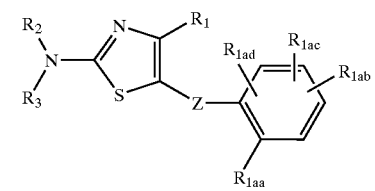

IIIc where

Z is as described above (preferably —S—, —CR$_4$R$_5$—S—, or —S—CR$_4$R$_5$— where R$_4$ and R$_5$ are H);

R$_1$ is as described above (preferably H);

R$_2$ and R$_3$ are as described above (including the description of preferred substituents);

R$_{1aa}$ is —C(O)$_q$H, —C(O)$_q$R$_6$, -Z$_4$-NR$_7$R$_8$, -Z$_4$-N(R$_9$)-Z$_5$-NR$_{10}$R$_{11}$ or -Z$_4$-N(R$_9$)-Z$_5$-R$_6$;

and

R$_{1ab}$, R$_{1ac}$ and R$_{1ad}$ are independently selected from any R$_1$ group (especially, H, alkyl, hydroxy, nitro, halo, —OR$_6$, —NR$_7$R$_8$, —C(O)$_q$H or —C(O)$_q$R$_6$).

Preferred compounds within the scope of formulae III include compounds of the following formula IV

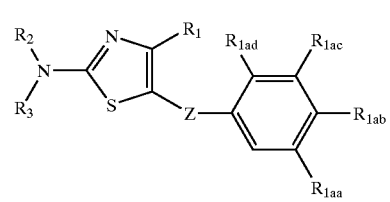

IV where

Z, R$_1$, R$_{1aa}$, R$_2$, and R$_3$ are as described above; and

One of R$_{1ab}$, R$_{1ac}$ and R$_{1ad}$ is H and the other two are independently alkyl, alkoxy, haloalkoxy, hydroxy, nitro, halo, —NR$_7$R$_8$, —C(O)$_q$H or —C(O)$_q$R$_6$) (preferably alkyl or alkoxy). (preferably, R$_{1c}$ is H when Z is —S—, and R$_{1d}$ is H when Z is —S—CR$_4$R$_5$— or —O—CR$_4$R$_5$—);

Compounds within the scope of formula IV include compounds of the following formula V:

IV

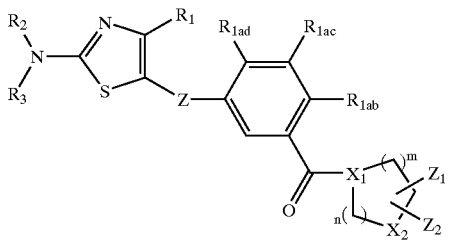

where
Z, $R_1$, $R_{1ab}$, $R_{1ac}$, $R_{1ad}$, $R_2$ and $R_3$ are described for formula IV;
$X_1$ is C or N (preferably N);
$X_2$ is $CZ_{3a}$, $NZ_{3a}$, O or S (preferably $CZ_{3a}$, $NZ_{3a}$ or O) (more preferably $NZ_{3a}$);
$Z_1$ and $Z_2$ are as described for formula I (preferably H);
$Z_{3a}$ is H, hydroxy, optionally substituted alkyl (especially optionally substituted with hydroxy, cyano, aryl, —$OZ_6$, -$Z_4$-$NZ_7Z_8$, —$C(O)_qH$ or —$C(O)_qZ_6$), optionally substituted heterocyclo (preferably optionally substituted piperidinyl, tetrazolyl, pyridinyl, pyrimidinyl, or pyrrazolyl), optionally substituted aryl or aralkyl (especially optionally substituted with halo), —$OZ_6$, —$C(O)_qH$, —$C(O)_qZ_{6a}$, -$Z_4$-$NZ_7Z_8$ (especially where $Z_4$ is a bond or —C(O)—), or -$Z_4$-N($Z_{10}$)-$Z_5$-$Z_6$ (especially where $Z_4$ is a bond or —C(O)— and $Z_5$ is —O—, —$SO_2$—, or —C(O)O—);
n is 1 to 3; and
m is zero to 2.

Methods of Preparation

The compounds of the formula I may be prepared by methods such as those illustrated in the following Schemes A through C and I through VIII. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined elsewhere in the specification or as specifically defined in a scheme.

The methods described herein may be carried out with starting materials and/or reagents in solution or alternatively, where appropriate, with one or more starting materials or reagents bound to a solid support (see (1) Thompson, L. A., Ellman, J. A., Chemical Reviews, 96, 555–600 (1996); (2) Terrett, N. K., Gardner, M., Gordon, D. W., Kobylecki, R. J., Steele, J., Tetrahedron, 51, 8135–8173 (1995); (3) Gallop, M. A., Barrett, R. W., Dower, W. J., Fodor, S. P. A., Gordon, E. M., Journal of Medicinal Chemistry, 37, 1233–1251 (1994); (4) Gordon, E. M., Barrett, R. W., Dower, W. J., Fodor, S. P. A., Gallop, M. A., Journal of Medicinal Chemistry, 37, 1385–1401 (1994); (5) Balkenhohl, F., von dem Bussche-Hünnefeld, Lansky, A., Zechel, C., Angewandte Chemie International Edition in English, 35, 2288–2337 (1996); (6) Balkenhohl, F., von dem Bussche-Hünnefeld, Lansky, A., Zechel, C., Angewandte Chemie, 108, 2436–2487 (1996); and (7) Sofia, M. J., Drugs Discovery Today, 1, 27–34 (1996)).

Compounds of formula I that contain chiral centers maybe obtained in non-racemic form by non-racemic synthesis or resolution by methods well known to those skilled in the art. Compounds that are non-racemic are designated as "chiral" in the examples.

In the examples described below it may be necessary to protect reactive functionality such as hydroxy, amino, thio or carboxy groups, where these are desired in the final product, to avoid their unwanted participation in reactions. The introduction and removal of protecting groups are well known to those skilled in the art, for example see (Green, T. W. in "Protective Groups in Organic Synthesis", John Wiley and Sons, 1991).

Scheme A

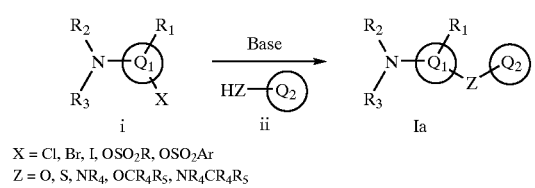

X = Cl, Br, I, $OSO_2R$, $OSO_2Ar$
Z = O, S, $NR_4$, $OCR_4R_5$, $NR_4CR_4R_5$

Scheme A illustrates a general method for forming compound Ia which is a compound of formula I where Z=O, S, or $NR_4$. Compound Ia can be formed by reacting compound i with compound ii in the presence of an organic or inorganic base e.g. alkalimetal alkoxide, alkyl or aryl lithium, or Grignard reagent in a protic or aprotic solvent e.g. tetrahydrofuran, ether, methyl alcohol, ethanol or dimethyl formamide at a temperature of 78° C. to 100° C.

Scheme B

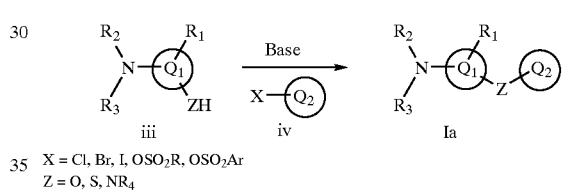

X = Cl, Br, I, $OSO_2R$, $OSO_2Ar$
Z = O, S, $NR_4$

Scheme B illustrates a general method for forming compound Ia which is a compound of formula I where Z=O, S, NR4. Compound Ia can be formed by reacting compound iii with compound iv in presence of an organic or inorganic base e.g. alkali metal alkoxide, alkalimetal hydride, alkyl or aryl lithium or Grignard reagent in a protic or a protic solvent e.g. THF, ether, methanol, ethanol or DMF at a temperature of −78° C. to 100° C.

Scheme C

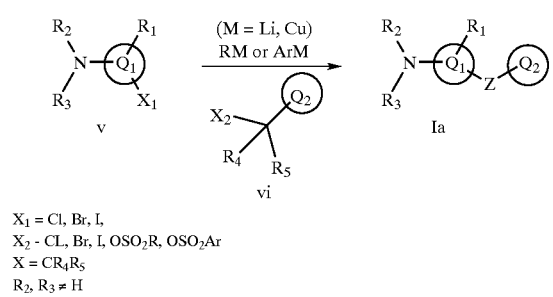

$X_1$ = Cl, Br, I,
$X_2$ - CL, Br, I, $OSO_2R$, $OSO_2Ar$
X = $CR_4R_5$
$R_2$, $R_3$ ≠ H

Scheme C illustrates a general method for forming Compound Ib which is a compound of formula I where Z=$CR_4R_5$. Compound Ib can be formed by reacting Compound v with an organometallic reagent e.g. alkyl or aryl lithium or cuprate or Grignard reagent and then reacting with Compound vi in an aprotic solvent e.g. ether, THF, DMF at a temperature of −78° C. to 60° C.

Methods for preparing preferred examples of compound I are illustrated in Schemes I to IX.

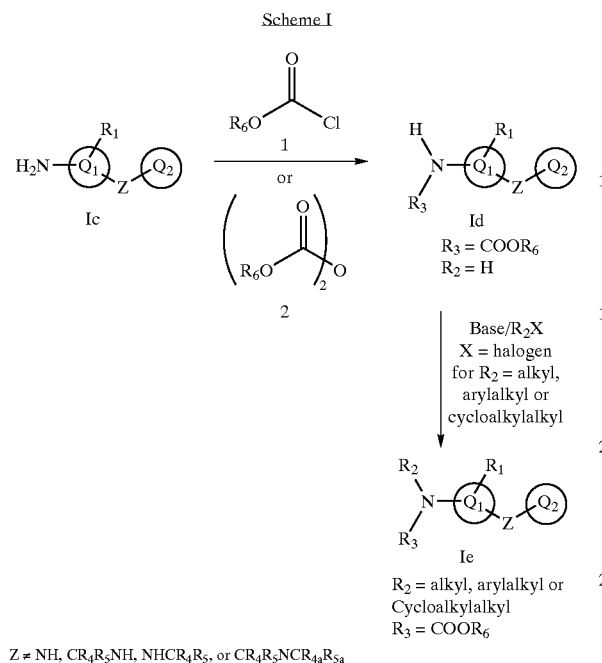

As shown in Scheme I, amine Ic which can be formed by methods described in Schemes A, B or C can be reacted with a chloroformate 1 or dicarbonate 2 to form Id. Compound Id can be treated with a base such as sodium hydride, sodium/potassium hexamethyl disilazide, or lithium diisopropylamide (LDA), and an alkylating agent $R_2X$ where X is halogen and $R_2$ is preferably alkyl, arylalkyl or cycloalkylalkyl to form Compound Ie.

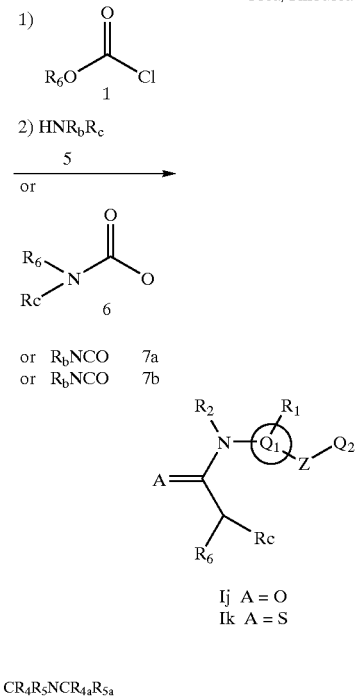

Scheme II illustrates methods which may be used for the preparation of Compounds Ig, Ih, Ii, Ij and Ik which are compounds of formula I where $R_2$ is any group as defined, $R_3$ is an acyl or thioacyl, Z is not —NH and $R_1$ is not a primary or secondary amine. Ig, Ih, Ii, Ij and Ik have other particular substituents which are specified in this Scheme and below. The starting compound If can be prepared by suitable methods described in Schemes A, B or C.

Amide Ig can be prepared by treatment of amine If with a carboxylic acid 3 in the presence of reagents which activate the carboxyl group for reaction as described above, for example BOP reagent, HATU and carbodiimides such as DCC or EDCI either alone or in combination with a hydroxybenzotriazole. Alternatively, the alidhalide 4 may be reacted with amine compound If in presence of an acid scavenger such as pyridine ordiisopropyl ethyl amine. The corresponding thioamide Ih can be prepared by treatment of amide Ig with Lawesson's reagent as described above. Carbamate Ii can be prepared by treatment of amine compound If with a chloroformate 1 or dicarbonate 2 in the presence of an acid scavenger such as diisopropylethylamine, triethylamine or an aqueous inorganic base such as sodium/potassium bicarbonate, sodium/potassium carbonate or hydroxide.

The urea Ij may be prepared by treatment of amine compound If with either: 1) a chloroformate 1, such as phenyl chloroformate, followed by reaction with an amine 5; 2) a carbamoyl chloride 6 in presence of an acid scavenger such as diisopropylethylamine; or 3) reaction with an isocyanate 7a (where $R_c$ in Ii=H). The corresponding thiourea Ik may be prepared by treatment of amine compound Ie with a isothiocyanate 7b.

Ra is selected from those groups included in the definition of $R_{6a}$ such that the group —C(═A)—$R_a$ is an acyl group within the definition of $R_3$. Rb and Rc are selected from those groups included in the definitions of $R_{7a}$ and $R_{8a}$, such that the group —C(=A)—N(Rb)(Rc) is an acyl or thioacyl group within the definition of $R_3$.

Scheme III

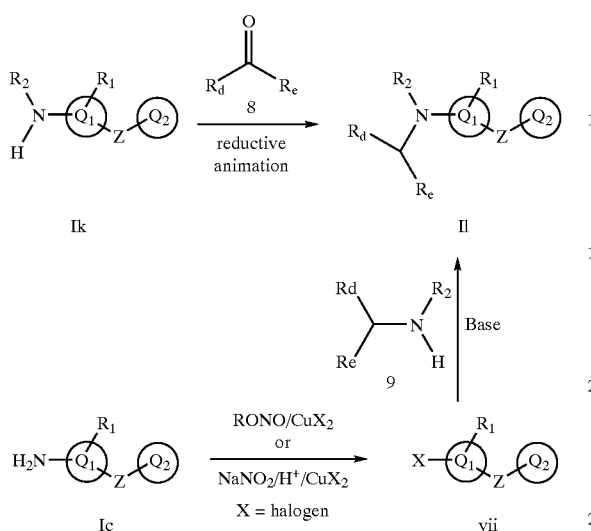

Ik  Il

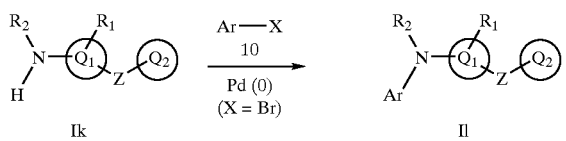

Ic  vii $R_2$ = any group as defined other than acyl
$R_3$ = alkyl, cycloalkyl, cycloalkylalkyl, cycloalkenylalkyl, aralkyl or saturated heterocycle
$Z \ne$ NH, $CR_4R_5NH$, $NHCR_4R_5$, or $CR_4R_5NCR_{4a}R_{5a}$ Scheme III illustrates a method which can be used for the preparation of Il, which is a compound of formula I where $R_2$ is any group as defined other than acyl, and which is selected such that the nitrogen to which it is attached is basic, R3 is alkyl, cycloalkyl, cycloalkyl-alkyl, cycloalkenylalkyl, aralkyl or saturated heterocycle and Z is not —NH. The starting compounds Ik and Ic can be prepared by suitable methods described in Schemes A, B and C. As shown in Scheme III, amine compound Ik is reacted with an aldehyde or ketone 8 under reductive amination conditions described above to give the Compound Il. Compound Il may also be prepared by treatment of an amine compound Ic, where $R_2$ and $R_3$ are hydrogen, with t-butyl/t-amyl nitrite or sodium nitrite and an acid such as HCl, $H_2SO_4$ in presence of a copper (II) halide to give the halo compound vii, followed by displacement with amine 9 in the presence or absence of a base such as sodium or potassium hydride or the like (see Lee et al., J. Heterocyclic Chemistry 22, 1621, 1985). Rd and Re are independently selected from hydrogen, alkyl, aryl, cycloalkyl or cycloalkenyl or together are alkylene or alkenylene completing a 3- to 8-membered saturated or unsaturated ring, such that the group —CH(Rd)(Re) is a group within the definition of R.

Scheme IV

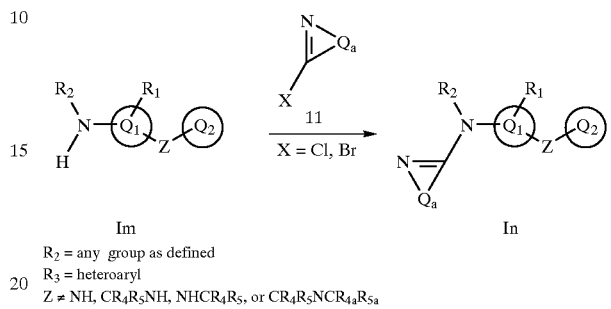

Ik  Il $R_2$ = any group as defined other than acyl
$R_3$ = aryl, heteroaryl
$Z \ne$ NH, $CR_4R_5NH$, $NHCR_4R_5$, or $CR_4R_5NCR_{4a}R_{5a}$ As shown in Scheme IV, when $R_2$ is any group as defined other than acyl, and is selected such that the nitrogen to which it is attached is basic, $R_3$ is an aryl or heteroaryl, amine compound Ik may be reacted with a halophenyl or haloheteroaromatic group 10 in the presence of a Pd(0) catalyst (See J. Am. Chem. Soc. 118, 7215, 1996) to give amine Il, which is a compound of formula I having the particular substituents described in this Scheme. The starting compound Il can be prepared by suitable methods described in Scheme A, B or C.

Scheme V

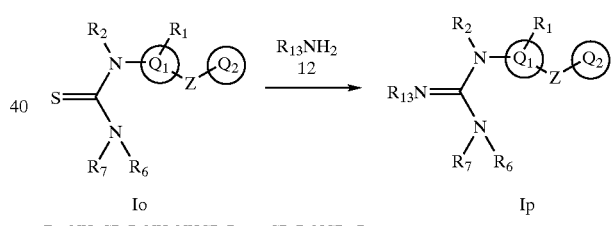

Im  In $R_2$ = any group as defined
$R_3$ = heteroaryl
$Z \ne$ NH, $CR_4R_5NH$, $NHCR_4R_5$, or $CR_4R_5NCR_{4a}R_{5a}$ As shown in Scheme V, when $R_2$ is any group as defined, $R_3$ is a heteroaromatic group, amine compound, Im may be reacted, in the presence of a base if needed, with a 2-halo-substituted heteroaromatic compound 11 where $Q_a$, together with atoms to which it is bonded, forms a 5- or 6-membered monocyclic or 10- to 12-membered bicyclic heteroaromatic group (such as forming 2-chloropyridine, 2-chloropyrimidine or 2-chloroquinoline) to give the amine compound In, where In is a compound of formula I having the particular substituents described in this scheme. The starting compound Im can be prepared by suitable methods described in Schemes A, B and C.

Scheme VI

Io  Ip $Z \ne$ NH, $CR_4R_5NH$, $NHCR_4R_5$, or $CR_4R_5NCR_{4a}R_{5a}$

As shown in Scheme VI, thiourea compound Io may be reacted with the appropriate amine 12 in the presence of bis-(2-oxo-3-oxazolidinyl) phosphinic chloride (BOP chloride), benzotriazol-1-yloxy-tris (dimethylamino) phosphonium hexafluoro-phosphate (BOP-reagent), [O-(7-azabenzotriazol-1-yl)-1,1,3,3-tetramethyl-uronium] hexafluorophosphate (HATU) and a carbodiimide such as dicyclohexylcarbodiimide (DCC) or 3-ethyl-e (dimethylamino) propyl carbodiimide (EDCI) or diisopropylcarbodiimide (DIC) in the presence of an organic base such as triethylamine, diisopropylethylamine or dimethylaminopyridine in solvents such as dimethylformamide, dichloromethane or tetrahydrofuran to form compound Ip, which is a compound of formula I having the particular substituents described in this scheme.

Alternatively, compound Io can be reacted with the appropriate amine 12 in the presence of a mercury (II) salt such as mercury chloride, or by other known methods in the literature, to form Ip. The starting material Io can be prepared by suitable methods described in Schemes A, B, or C or Scheme II.

Scheme VII

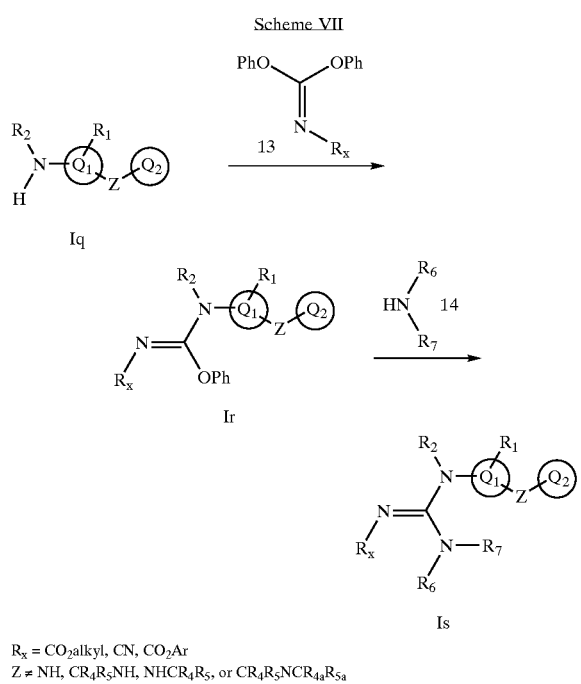

$R_x = CO_2$alkyl, CN, $CO_2$Ar
$Z \neq$ NH, $CR_4R_5$NH, NHCR$_4$R$_5$, or CR$_4$R$_5$NCR$_{4a}$R$_{5a}$ As shown in Scheme VII, amine Iq can be reacted with diphenyl cyanocarbonimidate 13 either alone or in the presence of a base such as sodium hydride, sodium/ potassium hexamethyldisilazide or dimethylaminopyridine in acetonitrile, tetrahydrofuran or dimethylformamide at room temperature or elevated temperature to form intermediate compound Ir which can be reacted with amine 14 to form compound Is, which is a compound of formula I having the particular substituents described in this scheme. The starting material Iq can be prepared by suitable methods described in Schemes A, B or C.

Scheme VIII

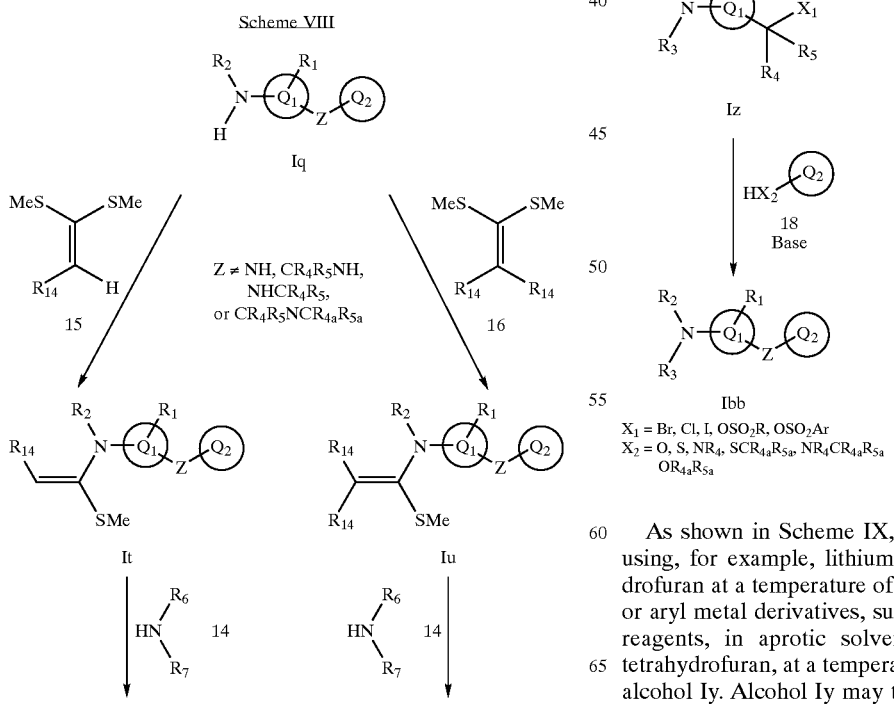

As shown in Scheme VIII, compound Iq can be reacted with either 15 or 16 either alone or in the presence of a base such as sodium hydride, sodium/potassium hexamethyldisilazide or dimethylaminopyridine in dimethylformamide or tetrahydrofuran at room temperature or elevated temperature to form compounds It or Iu, respectively, which can be reacted separately with amine 14 at room temperature or elevated temperature to form compound Iv or Iw, respectively. Compounds Iv and Iw are compounds of formula I having the particular substituents as described in this scheme. The starting material Iq can be prepared by suitable methods described in Schemes A, B or C.

Scheme IX

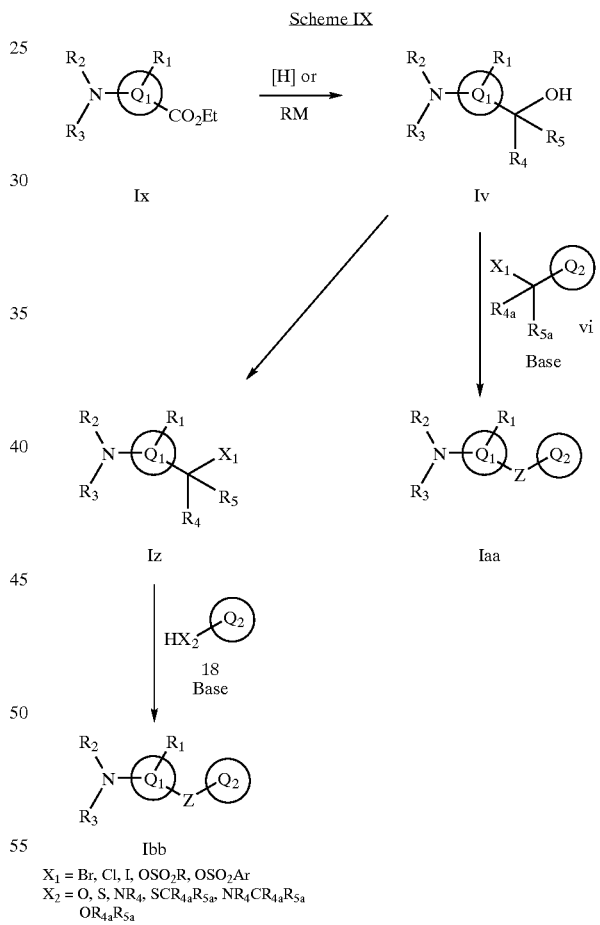

$X_1 = $ Br, Cl, I, OSO$_2$R, OSO$_2$Ar
$X_2 = $ O, S, NR$_4$, SCR$_4$R$_{5a}$, NR$_4$CR$_{4a}$R$_{5a}$
OR$_{4a}$R$_{5a}$

As shown in Scheme IX, compound Ix may be reduced using, for example, lithium aluminum hydride in tetrahydrofuran at a temperature of 0–55° C., or reacted with alkyl or aryl metal derivatives, such as alkyl lithium or Grignard reagents, in aprotic solvents such as diethyl ether or tetrahydrofuran, at a temperature of −78 to 100° C. to afford alcohol Iy. Alcohol Iy may then be reacted with compound vi alone or in the presence of organic or inorganic bases, such as sodium hydride, lithium hexamethyldisilazide, or potassium t-butoxide and the like, in a solvent such as dimethylformamide, and at a temperature of 0–100° C. to give compound Iaa. Alternatively, the alcohol moiety of Iy may be transformed into a leaving group via tosylation or conversion to a halide and then reacted with compound 18 alone or in the presence of bases such as sodium hydride in solvents such as tetrahydrofuran or dimethylformamide at a temperature from 0–100° C. to give compound Ibb.

Utility

The compounds of the present invention are immunosuppressive, anti-inflammatory, anti-allergic, and anti-cancer agents. The compounds of the present invention inhibit Tec family tyrosine kinases (especially Emt) and are thus useful in the treatment, including prevention and therapy, of Tec family tyrosine kinase-associated disorders, especially Emt-associated disorders. "Tec family tyrosine kinase-associated disorders" are those disorders which result from aberrant Tec family tyrosine kinase activity, and/or which are alleviated by the inhibition of one or more of these enzymes. Compounds within the scope of the present invention selectively inhibit Emt and are thus useful in the treatment, including prevention and therapy, of a range of disorders associated with the activation of Emt (e.g., inflammatory disorders, allergic disorders and cancer). In addition to Emt, the compounds of the present invention inhibit other Tec family kinases including Btk, Txk, Tec, and Bmx and are useful in the treatment of the disorders associated with the activation of these Tec family kinases. Such disorders are exemplified by, but are not limited to, transplant rejection; transplantation tolerance induction; arthritis including rheumatoid arthritis, psoriatic arthritis, and osteoarthritis; multiple sclerosis; chronic obstructive pulmonary disease (COPD) such as emphysema; inflammatory bowel diseases including ulcerative colitis and Crohn's disease; lupus (systemic lupus erythematosis); graft vs. host disease; T-cell mediated hypersensitivity diseases including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrom; autoimmune hyperthyroidism such as Graves's disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; diabetes (both type I and type II); other autoimmune diseases; cancers such as leukemias and lymphomas; glomerulonephritis; serum sickness; uticaria; allergic diseases including respiratory allergies (asthma, hayfever, allergic rhinitis) and skin allergies; scleracierma; mycosis fungoides; acute inflammatory responses (such as acute respiratory distress syndrome and ischemia/reperfusion injury); dermatomyositis; alopecia areata; chronic actinic dermatitis; eczema; Behcet's disease; Pustulosis palmoplanteris; Pyoderma gangrenum; Sezary's syndrom; atopic dermatitis; systemic schlerosis; and morphea.

In a particular embodiment, the compounds of the present invention are useful for the treatment of the aforementioned exemplary disorders irrespective of their etiology, for example, for the treatment of transplant rejection, rheumatoid arthritis, multiple sclerosis, chronic obstructive pulmonary disease, inflammatory bowel disease, lupus, graft vs. host disease, T-cell mediated hypersensitivity disease, psoriasis, Hashimoto's thyroiditis, Guillain-Barre syndrom, cancer, contact dermatitis, allergic disease such as allergic rhinitis, asthma, ischemric or reperfusion injury, or atopic dermatitis whether or not associated with the Tec family tyrosine kinases.

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene glycol).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to protein tyrosine kinase-associated disorders.

The compounds of the present invention may be employed alone or in combination with each other and/or other suitable therapeutic agents useful in the treatment of Tec family tyrosine kinase-associated disorders such as Emt inhibitors other than those of the present invention, antiinflammatories, antiproliferatives, chemotherapeutic agents, immunosuppressants, anticancer agents and cytotoxic agents.

Exemplary such other therapeutic agents include the following: protein tyrosine kinase inhibitors (such as those disclosed in WO 00/62778), cyclosporins (e.g., cyclosporin A), CTLA4-Ig, LEA-29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, phosphodiesterase (PDE) inhibitors, antihistamines, $p^{38}$ MAPK inhibitors, $LTD_4$ inhibitors such as zafirlukast (ACCOLATE) and montelukast (SINGULAIR), TNF-α inhibitors such as tenidap, anti-TNF antibodies or soluble TNF receptor such as etanercept (Enbrel), rapamycin (sirolimus or Rapamune), leflunimide (Arava), and cyclooxygenase-2 (COX-2) inhibitors such as celecoxib (Celebrex) and rofecoxib (Vioxx), or derivatives thereof, and the PTK inhibitors disclosed in the following U.S. Patent Applications, incorporated herein by reference in their entirety: Ser. No. 60/056,770, filed Aug. 25, 1997, Ser. No. 60/069,159, filed Dec. 9, 1997, Ser. No. 09/097,338, filed Jun. 15, 1998, Ser. No. 60/056,797, filed Aug. 25, 1997, Ser. No. 09/094,797, filed Jun. 15, 1998, Ser. No. 60/065,042, filed Nov. 10, 1997, Ser. No. 09/173,413, filed Oct. 15, 1998, Ser. No. 60/076,789, filed Mar. 4, 1998, and Ser. No. 09,262,525, filed Mar. 4, 1999. See the following documents and references cited therein: Hollenbaugh, D., Douthwright, J., McDonald, V., and Aruffo, A., "Cleavable CD40Ig fusion proteins and the binding to sgp[39]", J. Immunol. Methods (Netherlands), 188(1), p. 1–7 (Dec. 15 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", EMBO J (England), 11(12), p 4313–4321 (December 1992); and Moreland, L. W. et al., "Treatment of rheumatoid arthritis with a recombinant human tumor necrosis factor receptor (p75)-Fc fusion protein, New England J. of Medicine, 337(3), p. 141–147 (1997).

Exemplary classes of anti-cancer agents and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A–F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy.

Representative examples of these classes of anti-cancer and cytotoxic agents include, but are not limited to, mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodernolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: epothilone derivatives as found in U.S. Ser. No. 09/506,481 filed Feb. 17, 2000; German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253, and WO 00/00485; cyclin dependent kinase inhibitors as found in WO 99/24416; and prenyl-protein transferase inhibitors as found in WO 97/30992 and WO 98/54966.

The above other therapeutic agents, when employed in combination with the compounds of the present invention, may be used, for example, in those amounts indicated in the Physicians' Desk Reference (PDR) or as otherwise determined by one of ordinary skill in the art.

Compounds within the scope of the present invention can be assayed for Tec family tyrosine kinase inhibitory activity using methods such as those described by Hawkins, J. and Marcy, A. *Prot. Express. Purif.* 2001, 22, 211–219, employing modifications readily known to those of skill in the art.

The following example compounds are Tec family tyrosine kinase inhibitors (especially Emt inhibitors) and illustrate embodiments of the present invention. These examples are not intended to limit the scope of the claims. Compounds of the Examples are identified by the example and step in which they are prepared (for example, "1A" denotes the title compound of step A of Example 1), or by the example only where the compound is the title compound of the example (for example, "2" denotes the title compound of Example 2).

EXAMPLE 1

N-[5-[[3-[(4-Acetylpiperazin-1-yl)carbonyl]phenyl]thio]thiazol-2-yl]-4-(N,N-dimethylamino)benzamide

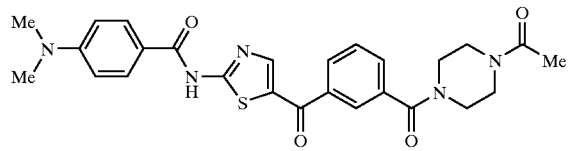

A. 3-[(2-Aminothiazol-5-yl)thio]benzoic acid methyl ester

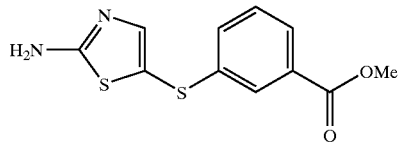

A 4.37 M solution of sodium methoxide in methanol (10 mL, 43.7 mmol) was added dropwise to a stirred suspension of 2-amino-5-bromothiazole hydrochloride (2.16 g, 10 mmol) and 3-carboxythiophenol (1.85 g, 12 mmol) in methanol (75 mL) at 0–5° C. The solution was allowed to warm to rt. for 2 h and a 4 M solution of hydrogen chloride in dioxane (15 mL, 60 mmol) was added. The suspension was stirred at rt. overnight and concentrated. The crude residue was diluted with satd. aqueous sodium bicarbonate solution (50 mL). The precipitated solid was filtered and washed with water (20 mL, 5×) and ether (20 mL, 5×). The solid was filtered and dried in vacuo at 60° C. to obtain the titled compound (1.97 g, 75%).

B. 3-[[2-[[(1,1-Dimethylethoxy)carbonyl]amino]thiazol-5-yl]thio]benzoic acid methyl ester

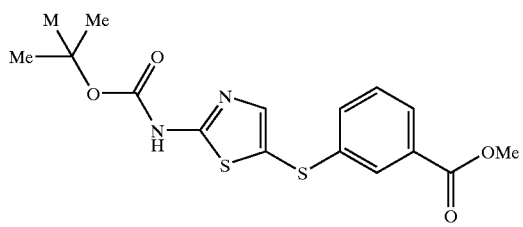

Di-t-butylcarbonate (4.36 g, 20 mmol) was added to a stirred solution of 2-amino-5-[(3-carbomethoxyphenyl)thio]thiazole (1.33 g, 5 mmol) and 4-N,N-dimethylaminopyridine (62 mg, 0.5 mmol) in THF (120 mL). The solution was stirred at rt. for 6 h and concentrated. The residue was purified using flash column chromatography on silica gel. Elution with 10% EtOAc in hexanes followed by 25% EtOAc in hexanes afforded a mixture of the titled compound and the corresponding bis(tert-butoxycarbonyl)amino adduct (1.8 g) as an oil.

C. 3-[[2-[[(1,1-Dimethylethoxy)carbonyl]amino]thiazol-5-yl]thio]benzoic acid

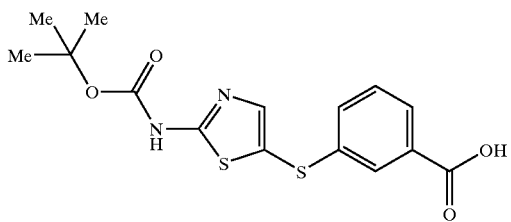

A 1 N aqueous sodium hydroxide solution (50 mL, 50 mmol) was added dropwise to a stirred solution of 2-tert-butoxycarbonylamino-5-[(3-carbomethoxyphenyl)thio]thiazole (1.8 g, (contaminated with bis(tert-butoxycarbonyl)amino adduct)) in a methanol-THF mixture (160 mL, 3:1). The solution was stirred at rt. for 24 h and concentrated. The residue was acidified with 2 N aqueous HCl (30 mL) and the suspension was extracted with dichloromethane-methanol mixture (120 mL, 3:1, 2×). The combined organic extract was dried (MgSO$_4$), filtered and concentrated in vacuo to obtain the titled compound (1.32 g, 75% overall yield from Example 1, part A) as an off-white solid.

D. 5-[[3-[(4-Acetylpiperazin-1-yl)carbonyl]phenyl]thio]thiazol-2-ylcarbamic acid 1,1-(dimethylethyl) ester

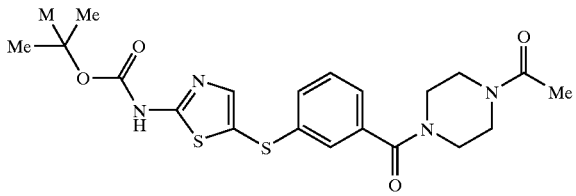

A suspension of 2-tert-butoxycarbonylamino-5-[(3-carboxyphenyl)thio]thiazole (528 mg, 1.5 mmol), N-acetylpiperazine (239 mg, 1.87 mmol), ethyl-3-(3-dimethylamino)propyl carbodiimide hydrochloride (400 mg, 2 mmol), 1-hydroxy-7-azabenzotriazole (272 mg, 2 mmol) and diisopropylethylamine (560 µL, 4 mmol) in THF (20 mL) was heated to 55° C. for 2 h. The mixture was cooled to rt. and concentrated. The residue was purified using column chromatography on silica gel eluted with 2% methanol in dichloromethane followed by 5% methanol in dichloromethane to obtain the titled compound (400 mg, 58%) as a white foam.

E. 4-Acetyl-1-[3-[(2-aminothiazol-5-yl)thio]benzoyl]piperazine

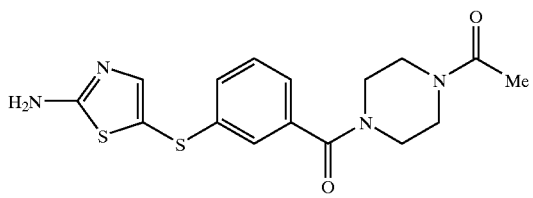

A solution of 2-tert-butoxycarbonylamino-5-[(3-N-acetylpiperazinylcarboxamidophenyl)thio]thiazole (400 mg, 0.87 mmol) in trifluoroacetic acid (6 mL) was stirred at rt. for 2 h. The solution was concentrated and the residue was partitioned between dichloromethane (30 mL) and satd. aqueous sodium bicarbonate solution (20 mL). The aq. layer was extracted with dichloromethane (20 mL). The dichloromethane extracts were combined, dried (MgSO$_4$), filtered and concentrated under reduced pressure and in vacuo to obtain the titled compound (300 mg, 95%) as a white solid.

F. N-[5-[[3-[(4-Acetylpiperazin-1-yl)carbonyl]phenyl]thio]thiazol-2-yl]-4-(N,N-dimethylamino)benzamide

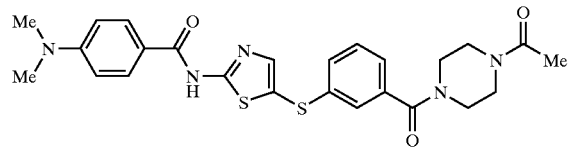

A stirred suspension of 2-amino-5-[(3-N-acetylpiperazinylcarboxamido-phenyl)-thio]thiazole (30 mg, 0.08 mmol), and 4-N,N-dimethylaminobenzoyl chloride (45.6 mg, 0.25 mmol) in dichloromethane (6 mL) was cooled to 0° C. and treated with pyridine (130 µL). The cooling bath was removed and the solution was stirred at rt. for 2 h. The mixture was concentrated in vacuo and the residue was purified using reversed phase automated preparative HPLC (conditions: YMC S5 ODS A 20×100 mm column, 15 min gradient starting from 10% solvent B (90% MeOH, 10% H$_2$O, 0.1% TFA) and 90% solvent A (10% MeOH, 90% H$_2$O, 0.1% TFA) to 90% solvent B and 10% solvent A, flow rate 20 mL/min, λ=220 nM to obtain the titled compound (8.7 mg, 21%) as a yellow solid: (M+H)$^+$= 510.27.

EXAMPLE 2

4-Acetyl-1-[5-[[2-[N-(6-bromopyridin-2-yl)amino]thiazol-5-yl]thio]-2-methylbenzoyl]piperazine

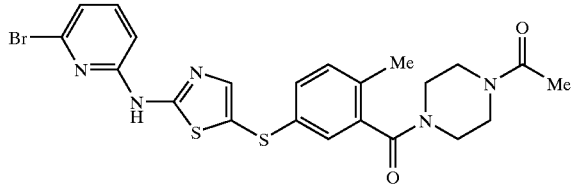

A. N-[[N-(6-Bromopyridin-2-yl)amino]thioxo]benzamide

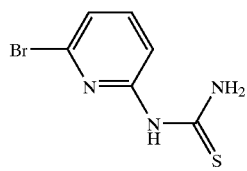

A solution of 2-amino-6-bromopyridine (3 g, 17.34 mmol) and benzoyl isothiocyanate (2.3 mL, 17.34 mmol) in acetone (30 mL) was stirred at rt. for 35 min. The suspension was cooled in an ice-water bath, diluted with water (150 mL) and stirred for several min. The precipitate was filtered, washed with water and dried in vacuo. The solid was triturated with ether to obtain the titled compound (4.99 g, 86%) as an off-white solid.

B. N-(6-Bromopyridin-2-yl)thiourea

A suspension of 2-bromo-6-benzoylthioureidopyridine (4.99 g, 14.84 mmol) in 10% aqueous sodium hydroxide solution (10.4 mL, 26 mmol) was stirred at rt. for 10 min and then under reflux for an additional 10 min. The mixture was cooled to 0° C. and acidified with 1 N aqueous HCl solution to pH 4.0 and then adjusted to pH 8.5 with satd. aqueous potassium bicarbonate solution. The mixture was stirred at 0° C. for several min and the precipitate was filtered, washed several times with water and dried in vacuo over P$_2$O$_5$ to obtain the titled compound (3.23 g, 94%) as a white solid.

C. 6-Bromo-N-(2-thiazolyl)pyridin-2-amine

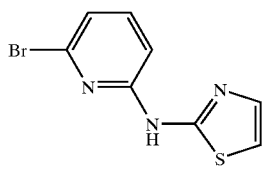

A suspension of 2-bromo-6-thioureidopyridine (3 g, 12.92 mmol) and chloroacetaldehyde (3.28 mL, 25.85 mmol) in ethanol (27 mL) and water (7 mL) was heated at reflux for 4.75 h. The solution was concentrated in vacuo and the residue was diluted with 1 N aqueous NaOH solution at 0° C., stirred for 10 min, and the pH was then adjusted to 8.5 by addition of 6 N aqueous HCl solution. The precipitate was collected by filtration, washed several times with water and dried in vacuo over $P_2O_5$ to obtain the titled compound (3.17 g, 96%) as a light yellow solid.

D. 6-Bromo-N-(5-bromo-2-thiazolyl)pyridin-2-amine

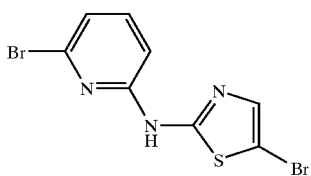

A solution of bromine (1.1 mL, 20.9 mmol) in acetic acid (15 mL) was added dropwise to a solution of 2-[(6-bromo-2-pyridinyl)amino]thiazole (2.68 g, 10.46 mmol) in acetic acid (23 mL) at 40° C. After addition, the mixture was stirred at rt. for 3 h. The mixture was diluted with aqueous potassium hydrogen sulfate solution (60 mL) at 0° C. and stirred for several min. The precipitated solid was filtered, washed several times with water and dried in vacuo over $P_2O_5$ to obtain the titled compound (3.28 g, 94%) as an off-white solid.

E. 5-[[2-[N-(6-Bromopyridin-2-yl)amino]thiazol-5-yl]thio]-2-methylbenzoic acid

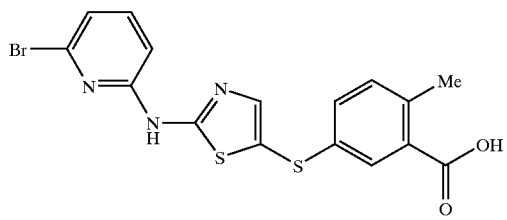

A suspension of 2-[(6-bromo-2-pyridinyl)amino]-5-bromothiazole (100 mg, 0.3 mmol), 3-carboxy-4-methylthiophenol (170 mg, 0.98 mmol) and sodium methoxide (210 µL, 25% w/w solution in methanol, 0.9 mmol) in methanol (4.9 mL) and THF (2 mL) was heated to 54° C. for 5.5 h. Supplemental sodium methoxide solution (1.42 mL) was added in portions over a period of 5 h. The mixture was heated to 54° C. for 16 h and concentrated. The residue was diluted with 1 N aqueous HCl solution at 0° C. and stirred for several minutes. The precipitated solid was filtered, washed several times with water and ether, and dried in vacuo over $P_2O_5$. Trituration with ether afforded the titled compound (103 mg, 81%) as an off-white solid.

F. 4-Acetyl-1-[5-[[2-[N-(6-bromopyridin-2-yl)amino]thiazol-5-yl]thio]-2-methylbenzoyl]piperazine

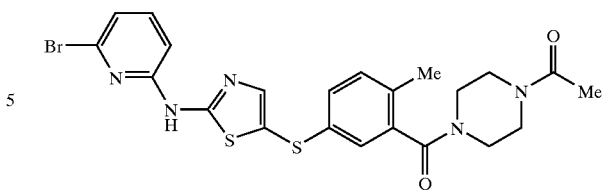

A suspension of 2-[(6-bromo-2-pyridinyl)amino]-5-(3-carboxy-4-methylphenyl-1-thio)thiazole (103 mg, 0.24 mmol), N-acetylpiperazine (37.2 mg, 0.29 mmol), ethyl-3-(3-dimethylamino)propyl carbodiimide hydrochloride (55.6 mg, 0.29 mmol), 1-hydroxy-7-azabenzotriazole (39.5 mg, 0.29 mmol) and diisopropylethylamine (130 µL, 0.72 mmol) in THF (10.5 mL) was heated to 58° C. for 1 h. The mixture was concentrated in vacuo and the residue was purified using column chromatography on silica gel. Elution with 1% methanol in dichloromethane followed by 2% and 4% methanol in dichloromethane afforded the titled compound (110 mg, 86%) as a yellow solid: mass spectrum $(M+H)^+$= 533.89.

EXAMPLE 3

4-Acetyl-1-[5-[[2-[N-(2-pyridinyl)amino]thiazol-5-yl]thio]-2-methylbenzoyl]piperazine

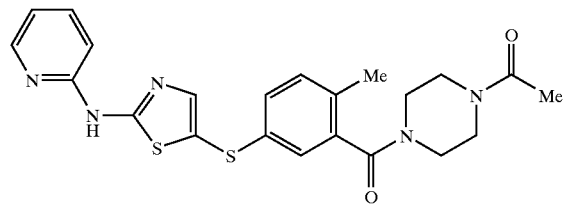

A. N-[[N-(2-Pyridinyl)amino]thioxo]benzamide

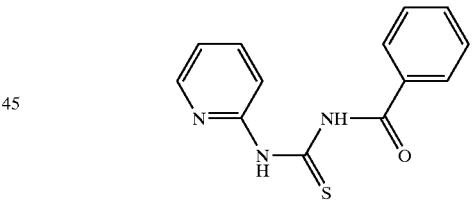

This material was prepared by an analogous method as that of Example 2, part A, except using 2-aminopyridine to give the title compound as an ochre solid (100%).

B. N-(2-Pyridinyl)thiourea

This material was prepared by an analogous method as that described in Example 2, part B, except using the compound described in Example 3, part A to give the title compound as a yellow powder (73%).

C. N-(2-Thiazolyl)-2-pyridinamine

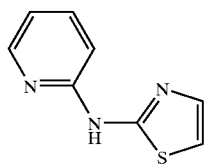

Example 3C was prepared by an analogous method as that of Example 2C, except using the compound described in Example 3, part B to give the title compound as an off-white solid (79%).

D. N-(5-Bromothiazol-2-yl)-2-pyridinamine

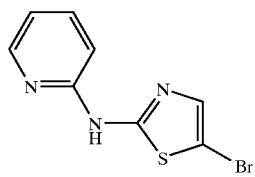

Example 3D was prepared by an analogous method as that of Example 2D, except using the compound described in Example 3, part C to give the title compound as an off-white solid (95%).

E. 2-Methyl-5-[[2-[N-(2-pyridinyl)amino]thiazol-5-yl]thio]benzoic acid

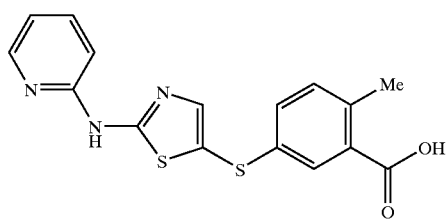

Example 3E was prepared by an analogous method as that of Example 2E, except using the compound described in Example 3, part D to give the title compound as a pale tan solid (84%).

F. 4-Acetyl-1-[5-[[2-[N-(2-pyridinyl)amino]thiazol-5-yl]thio]-2-methylbenzoyl]piperazine

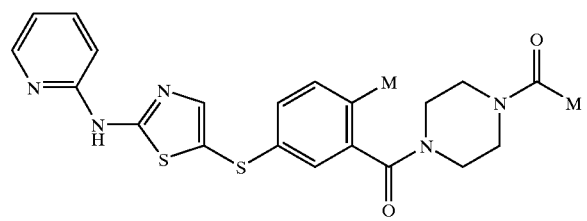

Example 3F was prepared by an analogous method as that of Example 2F, except using the compound described in Example 3, part E to give the title compound as an off-white solid: mass spectrum $(M+H)^+$=454.11.

EXAMPLE 4

4-Acetyl-1-[3-[[2-[N-(6-bromopyridin-2-yl)amino]thiazol-5-yl]thio]benzoyl]piperazine

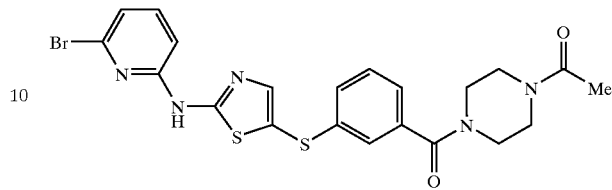

A. 3-[[2-[N-(6-Bromopyridin-2-yl)amino]thiazol-5-yl]thio]benzoic acid

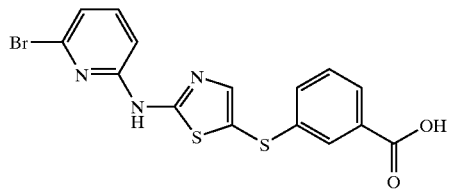

Example 4A was prepared by an analogous method as that of Example 2E, except using 3-carboxythiophenol in place of 3-carboxy-4-methylthiophenol to give the title compound as a solid.

B. 4-Acetyl-1-[3-[[2-[N-(6-bromopyridin-2-yl)amino]thiazol-5-yl]thio]benzoyl]piperazine

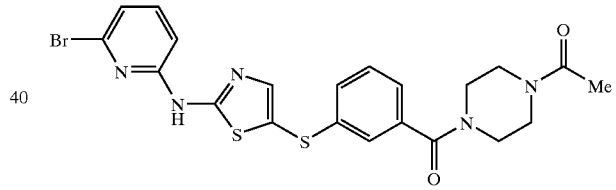

Example 4B was prepared by an analogous method as that of Example 2F, except using the compound described in Example 4, part A to give the title compound as a light peach-colored solid: mass spectrum $(M+H)^+$=520.13.

EXAMPLE 5

4-Acetyl-1-[3-[[2-[N-(2-pyridinyl)amino]thiazol-5-yl]thio]benzoyl]piperazine

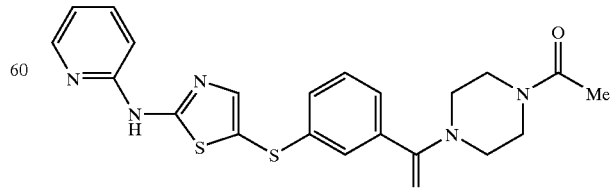

A. 3-[[2-[N-(2-Pyridinyl)amino]thiazol-5-yl]thio]benzoic acid

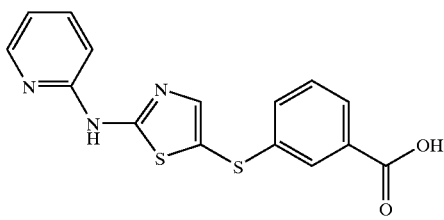

Example 5A was prepared by an analogous method as that of Example 2E, except using the compound described in Example 3, part D and 3-carboxythiophenol in place of 3-carboxy-4-methylthiophenol to give the title compound as a solid.

B. 4-Acetyl-1-[3-[[2-[N-(2-pyridinyl)amino]thiazol-5-yl]thio]benzo-yl]piperazine

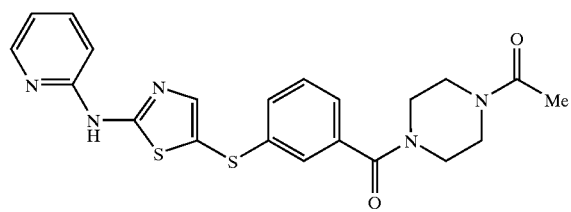

Example 5B was prepared by an analogous method as that of Example 2F, except using the compound described in Example 5, part A to give the title compound as an off-white solid: mass spectrum $(M+H)^+=440.3$.

EXAMPLE 6

4-Acetyl-1-[3-[[2-[N-(6-methylpyridin-2-yl)amino]thiazol-5-yl]thio]benzoyl]piperazine

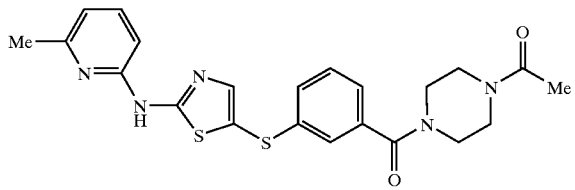

Example 6 was prepared by an analogous method as that of Example 2, except using 2-amino-6-methylpyridine in place of 2-amino-6-bromopyridine in Example 2A and 3-carboxythiophenol in place of 3-carboxy-4-methylthiophenol in Example 2E to give the title compound as a white solid: mass spectrum $(M+H)^+=454.11$.

EXAMPLE 7

4-Acetyl-1-[3-[[2-[N-(5-bromo-6-methylpyridin-2-yl)amino]thiazol-5-yl]thio]benzoyl]piperazine

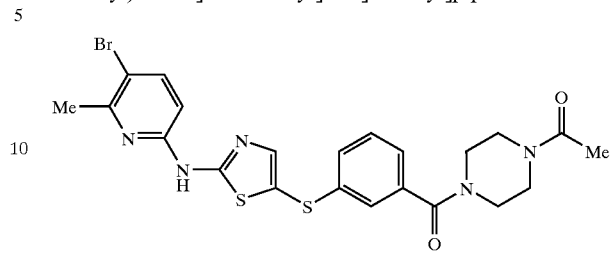

Example 7 was prepared by an analogous method as that of Example 2, except using 2-amino-5-bromo-6-methylpyridine in place of 2-amino-6-bromopyridine in Example 2A and 3-carboxythiophenol in place of 3-carboxy-4-methylthiophenol in Example 2E to give the title compound as a light tan solid: mass spectrum $(M+H)^+=534$.

EXAMPLE 8

4-Acetyl-1-[3-[[2-[N-(2-quinolinyl)amino]thiazol-5-yl]thio]benzoyl]piperazine

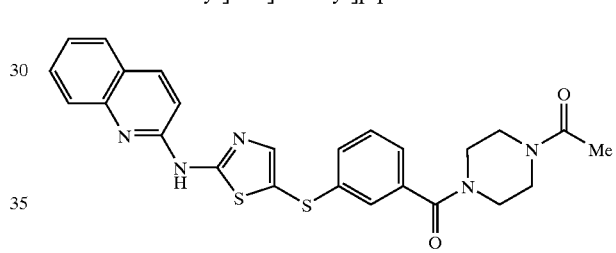

Example 8 was prepared by an analogous method as that of Example 2, except using 2-amino-quinoline in place of 2-amino-6-bromopyridine in Example 2A and 3-carboxythiophenol in place of 3-carboxy-4-methylthiophenol in Example 2E to give the title compound as a yellow solid: mass spectrum $(M+H)^+=490.08$.

EXAMPLE 9

4-Acetyl-1-[3-[[2-[N-(2-pyridinyl)amino]thiazol-5-yl]thiol]-4-methylbenzoyl]piperazine

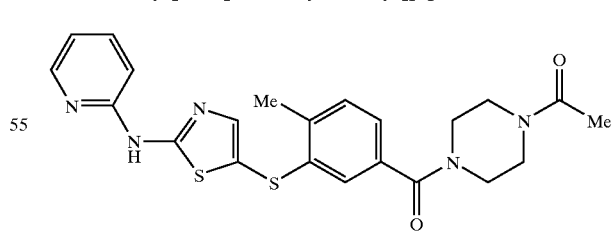

Example 9 was prepared by an analogous method as that of Example 2, except using 2-amino-pyridine in place of 2-amino-6-bromopyridine in Example 2A and 3-carboxy-6-methylthiophenol in place of 3-carboxy-4-methylthiophenol in Example 2E to give the title compound as a white solid: mass spectrum $(M+H)^+=454.13$.

EXAMPLE 10

4-Acetyl-1-[3-[[2-[N-[6-(1-piperidinyl)pyridin-2-yl]amino]thiazol-5-yl]thio]benzoyl]piperazine

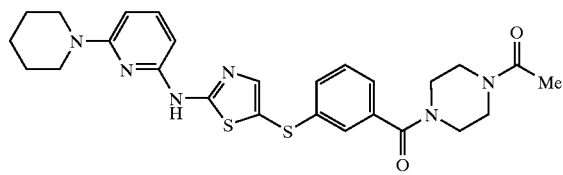

A solution of Example 4 (30 mg, 0.058 mmol), piperidine (86 μL, 0.87 mmol), 4-dimethylaminopyridine (7.1 mg, 0.058 mmol) in pyridine (300 μL) was heated to 134° C. in a sealed vial under nitrogen for 8.75 h. Most of pyridine was removed on a speed-vac at 40° C. The residue was purified using reversed phase automated preparative HPLC (conditions: YMC S5 ODS A 20×100 mm column, 15 min gradient starting from 10% solvent B (90% MeOH, 10% $H_2O$, 0.1% TFA) and 90% solvent A (10% MeOH, 90% $H_2O$, 0.1% TFA) to 90% solvent B and 10% solvent A, flow rate 20 mL/min, λ=220 nM) to obtain the titled compound (25.2 mg, 68%) as a light tan solid.

EXAMPLES 11 THROUGH 22

General Procedure

Polymer-supported diisopropylethylamine (37.6 mg, 0.124 mmol) was dispensed into each well of a 48 well Mini-block reactor. A 0.087 M solution of the appropriate amines in THF-DMF mixture (1 mL, 9:1) was added to each well using the TECAN liquid handler. A solution of the carboxylic acid described in procedure 3E (10 mg, 0.029 mmol), ethyl-3-(3-dimethylamino)propylcarbodiimide hydrochloride (6.71 mg, 0.035 mmol), 1-hydroxy-7-azabenzotriazole (4.76 mg, 0.035 mmol) in THF-DMF mixture (1 mL, 4:1) was added to each well using the TECAN liquid handler. The Mini-block was sealed and mechanically shaken at 60° C. for 5 h and at room temperature for an additional 16 h. Polystyrene supported methylisocyanate resin (109.5 mg, Novabiochem) was added to each well and shaking was continued at room temperature for 16 h. Each reaction mixture was loaded onto cation-exchange cartridges (CUBCX1HL, size: 500 mg/3 mL, United Chemical Technologies) and eluted sequentially with THF (8 mL), MeOH (8 mL), and 0.2 N ammonia in MeOH (4 mL). Fractions containing products were concentrated using a speed-vac. Residues were dissolved in THF-DMF mixture (9:1) and passed through anion exchange cartridges (CHQAX1, size: 500 mg/3 mL, United Chemical Technologies) and eluted with MeOH (2 mL). Fractions containing the products were concentrated using the speed-vac to give Examples 11–22.

| Ex. No. | Name | Structure | MS $(M + H)^+$ |
|---|---|---|---|
| 11 | 4-(2-Pyrimidinyl)-1-[5-[[2-[N-(2-pyridinyl)amino]thiazol-5-yl]thio]-2-methylbenzoyl]piperazine | 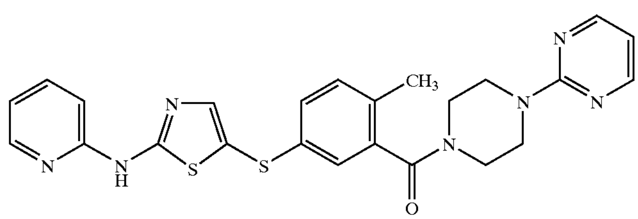 | 488.3 |
| 12 | 4-Hydroxy-1-[5-[[2-[N-(2-pyridinyl)amino]thiazol-5-yl]thio]-2-methylbenzoyl]piperidine | 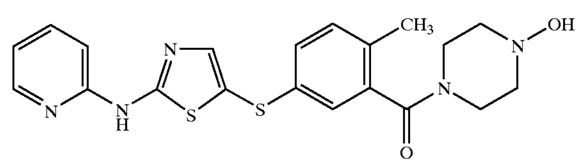 | 427.33 |
| 13 | 1,2,5,6-Tetrahydro-1-[5-[[2-[N-(2-pyridinyl)amino]thiazol-5-yl]thio]-2-methylbenzoyl]pyridine | 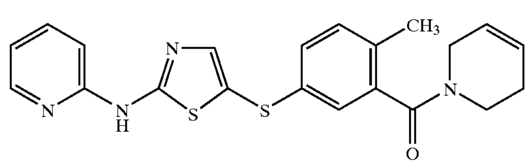 | 409.2 |
| 14 | 4-[2-(4-Morpholinyl)-2-oxoethyl]-1-[5-[[2-[-(2-pyridinyl)amino]thiazol-5-yl]thio]-2-methylbenzoyl]piperazine | 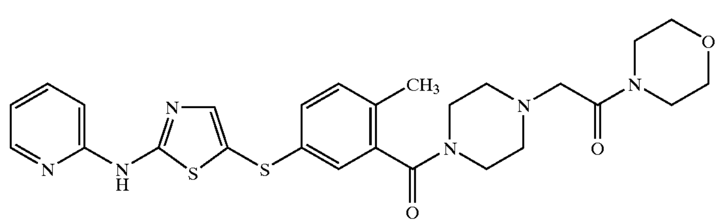 | 456.2 |

-continued

| Ex. No. | Name | Structure | MS (M + H)+ |
|---|---|---|---|
| 15 | 3-(Hydroxymethyl)-1-[5-[[2-[N-(2-pyridinyl)amino]thiazol-5-yl]thio]-2-ethylbenzoyl]piperidine | 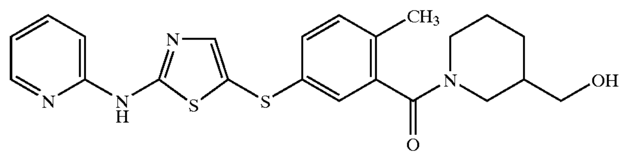 | 441.15 |
| 16 | 4-(1-Piperidinyl)-1-[5-[[2-[N-(2-pyridinyl)amino]thiazol-5-yl]thio]-2-methylbenzoyl]piperidine | 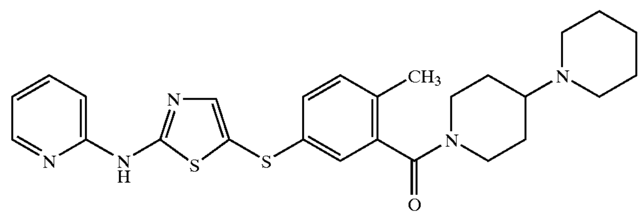 | 494.3 |
| 17 | 4-Formyl-1-[5-[ 2-[N-(2-pyridinyl)amino]thiazol-5-yl]thio]-2-methylbenzoyl]piperazine | 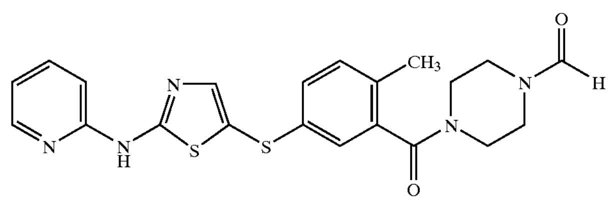 | 440.08 |
| 18 | 3-Methyl-1-[5-[[2-[N-(2-pyridinyl)amino]thiazol-5-yl]thio]-2-methylbenzoyl]piperidine | 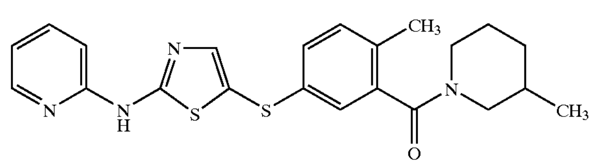 | 425.18 |
| 19 | N-Methyl-N-phenyl-4-[5-[[2-[N-(2-pyridinyl)amino]thiazol-5-yl]thio]-2-methylbenzoyl]-1-piperazineacetamide | 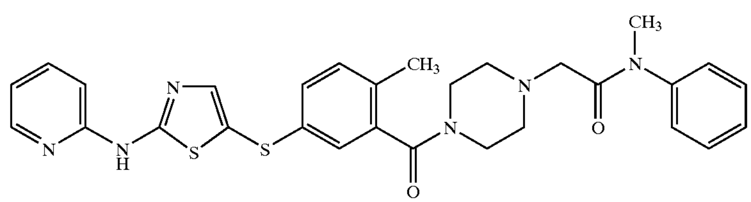 | 559.3 |
| 20 | 4-[5-[[2-[N-(2-Pyridinyl)amino]thiazol-5-yl]thio]-2-methylbenzoyl]-1-piperazineacetic acid ethyl ester | 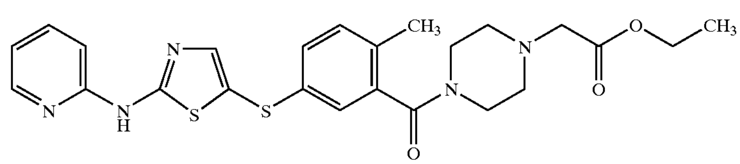 | 498.18 |
| 21 | N-(2-Cyanoethyl)-2-methyl-5-[[2-[N-(2-pyridinyl)amino]thiazol-5-yl]thio benzamide | 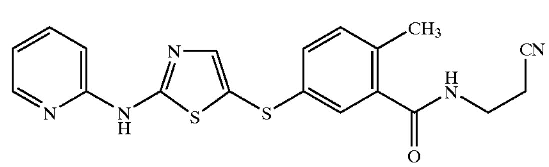 | 396.14 |
| 22 | N-(Cyanomethyl)-2-methyl-5-[[2-[N-(2-pyridinyl)amino]thiazol-5-yl]thio]benzamide | 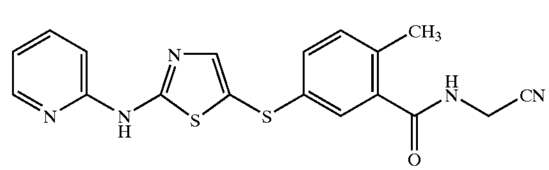 | 382.12 |

EXAMPLE 23

N-[5-[[5-[(4-Acetylpiperazin-1-yl)carbonyl]-2-methylphenyl]thio]thiazol-2-yl]-4-(N,N-dimethylamino)benzamide

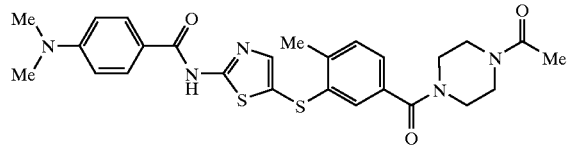

A. 3-[(2-Aminothiazol-5-yl)thio]-4-methylbenzoic acid methyl ester

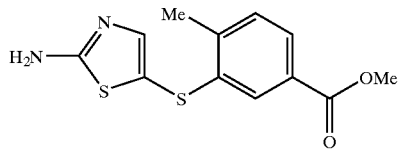

A 4.37 M solution of sodium methoxide in methanol (4.75 mL, 20.76 mmol) was added dropwise to a stirred suspension of 2-amino-5-bromothiazole hydrobromide (1.25 g, 4.8 mmol) and 3-carboxy-6-methyl-thiophenol (0.74 g, 4.4 mmol) in methanol (75 mL) at 0–5° C. The solution was stirred at 75° C. overnight. The mixture was concentrated in vacuo and the residue was dissolved in water and then acidified with aqueous HCl solution. The precipitated brown solid was filtered, washed with water and dried in vacuo to obtain the carboxylic acid (1.15 g). A solution of this acid in MeOH, 4 N hydrogen chloride in dioxane and conc. $H_2SO_4$ (20 drops) was heated under reflux for 3 days. The solution was concentrated and the residue was partitioned between EtOAc and satd. aqueous $NaHCO_3$ solution. The EtOAc extract was washed with satd. aqueous $NaHCO_3$ solution, dried ($Na_2SO_4$), filtered and concentrated in vacuo to obtain the title compound (1 g, 81%) as a yellowish-brown solid.

B. 3-[[2-[[4-(N,N-Dimethylamino)benzoyl]amino]thiazol-5-yl]thio]-4-methylbenzoic acid methyl ester

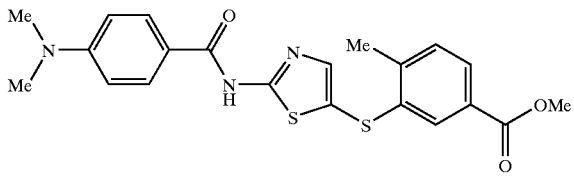

A suspension of compound A (1 g, 3.6 mmol), and 4-N,N-dimethylaminobenzoyl chloride (1.31 g, 7.1 mmol) in dichloromethane (25 mL) and pyridine (1 mL) was stirred at rt. for 2 days. Supplemental 4-N,N-dimethylaminobenzoyl chloride (500 mg, 2.72 mmol) was added and the mixture was stirred at rt. overnight. The solution was partitioned between dichloromethane and water. The dichloromethane extract was washed with 1 N aq. HCl solution, satd. aq. $NaHCO_3$ solution, dried ($Na_2SO_4$), filtered, and concentrated in vacuo to obtain the crude product, which was used without further purification.

C. 3-[[2-[[4-(N,N-Dimethylamino)benzoyl]amino]thiazol-5-yl]thio]-4-methylbenzoic acid

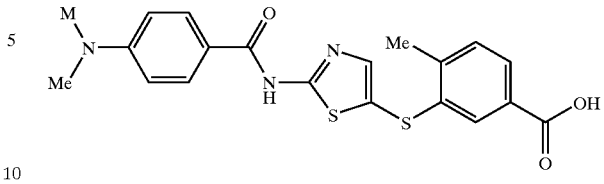

A 1 N aqueous sodium hydroxide solution (25 mL, 25 mmol) was added dropwise to a stirred solution of crude compound B in methanol. The solution was stirred at rt. for 72 h and concentrated. The residue was partitioned between dichloromethane and water. The aqueous extract was acidified with 1 N aqueous HCl solution and the precipitated solid was collected by filtration and dried in vacuo to obtain the title compound C (850 mg, 58%) as a tan solid.

D. N-[5-[[5-[(4-Acetylpiperazin-1-yl)carbonyl]-2-methylphenyl]thio]thiazol-2-yl]-4-(N,N-dimethylamino)benzamide

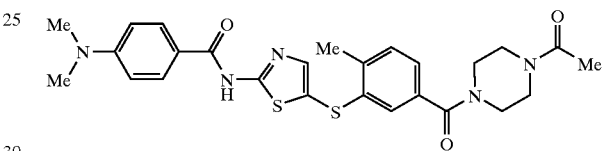

A suspension of compound C (380 mg, 0.92 mmol), N-acetylpiperazine (236 mg, 1.84 mmol), ethyl-3-(3-dimethylamino)propyl carbodiimide hydrochloride (350 mg, 1.8 mmol), 1-hydroxy-7-azabenzotriazole (250 mg, 1.8 mmol) and diisopropylethylamine (1 mL, 7.1 mmol) in THF (20 mL) was heated to 66° C. overnight. The mixture was cooled to rt. and concentrated. The residue was purified using reversed phase automated preparative HPLC (conditions: YMC S5 ODS A 20×100 mm column, 15 min gradient starting from 10% solvent B (90% MeOH, 10% $H_2O$, 0.1% TFA) and 90% solvent A (10% MeOH, 90% $H_2O$, 0.1% TFA) to 90% solvent B and 10% solvent A, flow rate 20 mL/min, λ=220 nM) to obtain the title compound (73 mg, 15% yield) as a yellow solid: mass spectrum $(M+H)^+$= 524.14.

EXAMPLE 24

N-[5-[[3-[(4-Acetylpiperazin-1-yl)carbonyl]-4-methylphenyl]thio]thiazol-2-yl]-4-(N,N-dimethylamino)benzamide

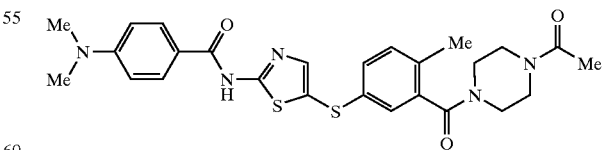

Compound 24 was prepared by an analogous method as that of 23, except substituting 3-carboxy-4-methylthiophenol in place of 3-carboxy-6-methylthiophenol in Example 23A to give the title compound 24 as an orange solid: mass spectrum $(M+H)^+$=524.11.

EXAMPLE 25

N-[5-[[3-[(4-Acetylpiperazin-1-yl)carbonyl]-4,5-dimethylphenyl]thio]thiazol-2-yl]-4-(N,N-dimethylamino)benzamide

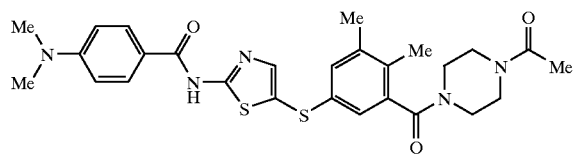

Example 25 was prepared by an analogous method as that of Example 23, except substituting 3-carboxy-4,5-dimethylthiophenol for 3-carboxy-6-methylthiophenol in Example 23A to give the title compound as a light salmon colored solid: mass spectrum (M+H)$^+$=538.33.

EXAMPLE 26

N-[5-[[3-[(4-Acetylpiperazin-1-yl)carbonyl]-4-aminophenyl]thio]thiazol-2-yl]-4-(N,N-dimethylamino)benzamide

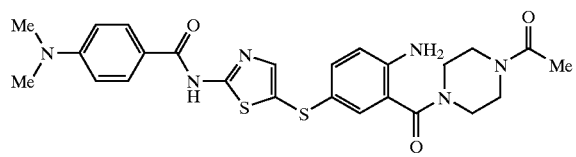

Example 26 was prepared by an analogous method as that of 23, except substituting 3-carboxy-4-acetamido-thiophenol for 3-carboxy-6-methylthiophenol in Example 23A to give the title compound as a yellow solid: mass spectrum (M+H)$^+$=525.21.

EXAMPLE 27

N-[5-[[5-[(4-Acetylpiperazin-1-yl)carbonyl]-2,4-dimethylphenyl]thio]thiazol-2-yl]-4-(N,N-dimethylamino)benzamide

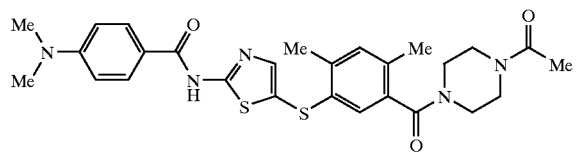

Example 27 was prepared by an analogous method as that of 23, except substituting 3-carboxy-4,6-dimethylthiophenol for 3-carboxy-6-methylthiophenol in Example 23A to give the title compound as a light amber solid: mass spectrum (M+H)$^+$=538.44.

EXAMPLE 28

N-[5-[[3-[(4-Acetylpiperazin-1-yl)carbonyl]-4-hydroxyphenyl]thio]thiazol-2-yl]-4-(N,N-dimethylamino)benzamide

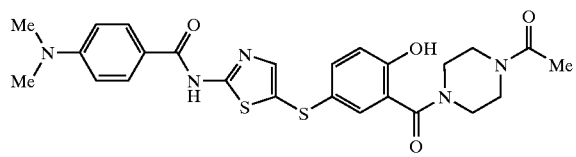

Example 28 was prepared by an analogous method as that of 23, except substituting 3-carboxy-4-hydroxy-thiophenol for 3-carboxy-6-methylthiophenol in Example 23A to give the title compound as a yellow solid: mass spectrum (M+H)$^+$=526.45.

EXAMPLE 29

N-[5-[[5-[(4-Acetylpiperazin-1-yl)carbonyl]-2,4-dimethylphenyl]thio]thiazol-2-yl]-4-(1,1-dimethylethyl)benzamide

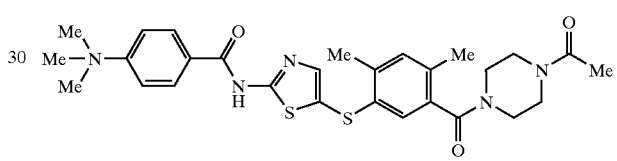

Example 29 was prepared by an analogous method as that of 23, except substituting 3-carboxy-4,6-dimethylthiophenol for 3-carboxy-6-methylthiophenol in Example 23A and substituting 4-tert-butylbenzoyl chloride for 4-N,N-dimethylaminobenzoyl chloride in Example 23B to give the title compound as an amber solid: mass spectrum (M+H)$^+$=551.12.

EXAMPLE 30

4-(1,1-Dimethylethyl)-N-[5-[[5-[(4-hydroxypiperidin-1-yl)carbonyl]-2,4-dimethylphenyl]thio]thiazol-2-yl]benzamide

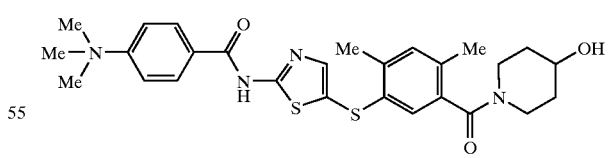

Example 30 was prepared by an analogous method as that of 23, except substituting 3-carboxy-4,6-dimethylthiophenol for 3-carboxy-6-methylthiophenol in Example 23A, substituting 4-t-butylbenzoyl chloride for 4-N,N-dimethylaminobenzoyl chloride in Example 23B and substituting 4-hydroxypiperidine for N-acetylpiperazine in Example 23D to give the title compound as an amber solid: mass spectrum (M+H)$^+$=524.32.

EXAMPLE 31

N-[5-[[[3-[(4-Acetylpiperazin-1-yl)carbonyl]phenyl]methoxy]methyl]thiazol-2-yl]-4-(1,1-dimethylethyl)benzamide

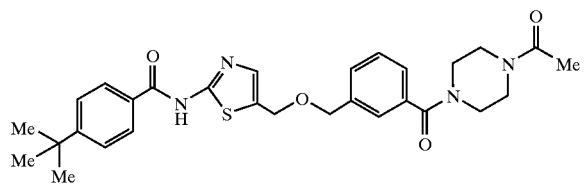

A. 2-[N-[4-(1,1-Dimethylethyl)benzoyl]amino]thiazole-5-carboxylic acid ethyl ester

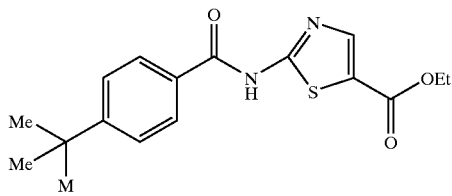

A solution of ethyl 2-aminothiazole-5-carboxylate (0.52 g, 3.0 mmol), 4-t-butylbenzoyl chloride (1.3 mL, 6.7 mmol) and pyridine (1.2 mL) in dichloromethane (10 mL) was stirred at 0° C. for 1.25 h. It was then diluted with dichloromethane and washed with aqueous HCl (1 N) twice, saturated aqueous sodium bicarbonate, and brine. After drying over sodium sulfate, filtration and concentration in vacuo gave a burgundy oil. Trituration with hexane afforded the desired amide as a light tan solid (0.88 g, 88% yield): LC/MS RT=3.85 min; mass spectrum (M+H)$^+$=333.16.

B. 4-(1,1-Dimethylethyl)-N-[(5-hydroxymethyl)thiazol-2-yl]benzamide

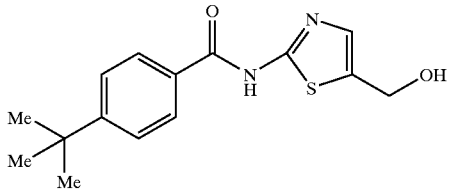

To a light tan suspension of ethyl 2-[[4-(1,1-dimethylethyl)phenyl)carbonyl]amino]-thiazole-5-carboxylate (0.88 g, 2.6 mmol) in tetrahydrofuran (7.0 mL) under nitrogen at 0° C. was added dropwise lithium aluminum hydride (1 M in THF, 10.6 mL). After 1.75 h, ice was added, followed by 1 N aqueous HCl. The mixture was extracted using ethyl acetate, and the combined organic layers were dried over sodium sulfate, filtered, and concentrated in vacuo to give the desired product as a light yellow solid (0.73 g, 95% yield): LC/MS RT=3.11 min; mass spectrum (M+H)$^+$=291.13.

C. 4-Acetyl-1-(3-chloromethyl)benzoylpiperazine

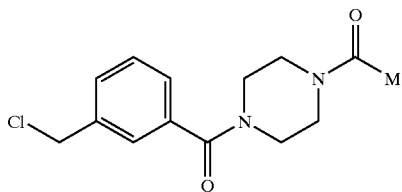

To a solution of 3-chloromethylbenzoyl chloride (5.34 g, 28.2 mmol) in dichloromethane (25 mL) was added a solution of 1-acetylpiperazine (7.30 g, 57.0 mmol) in dichloromethane (25 mL) at 0° C. over 10 min. The resulting mixture was stirred at 0° C. for 1 hour and then at room temperature for another hour. During the reaction period, the mixture became cloudy. It was diluted with dichloromethane, washed with water, 1 N HCl, water, brine, and dried over anhydrous MgSO$_4$. Evaporation of solvent gave the desired product (7.92 g, 100%) as a pale yellow viscous oil: LC/MS RT=0.92 min; mass spectrum (M+H)$^+$=281.19.

D. N-[5-[[[3-[(4-Acetylpiperazin-1-yl)carbonyl]phenyl]methoxy]methyl]thia-zol-2-yl]-4-(1,1-dimethylethyl)benzamide

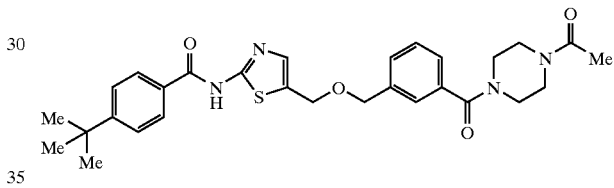

To a solution of 2-[[4-(1,1-dimethylethyl)phenyl)carbonyl]amino]-5-hydroxymethylthiazole (0.285 g, 0.983 mmol) and N-acetylpiperazinyl-(3-chloromethyl)benzamide (0.276 g, 0.983 mmol) in DMF (30 mL) at 0° C. was added NaH (60% dispersion in mineral oil, 0.197 g, 4.92 mmol). The mixture was heated at 60° C. overnight and was quenched by adding MeOH. The solution was neutralized to pH 8 using 1 N HCl and diluted with ethyl acetate The solution was then washed with water, brine, dried over anhydrous MgSO$_4$, and concentrated under vacuum. The residue was purified using flash column chromatography (5% MeOH/CHCl$_3$) to afford 30 mg of the desired material as a white solid: LC/MS RT=3.49 min; mass spectrum (M+H)$^+$=535.20.

EXAMPLE 32

4-(1,1-Dimethylethyl)-N-[5-[[[3-[[4-(2-pyrimidinyl)piperazin-1-yl]carbonyl]-4-methylphenyl]thiol]methyl]thiazol-2-yl]benzamide

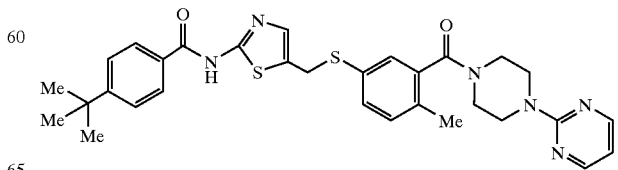

A. N-[(5-Chloromethyl)thiazol-2-yl]-4-(1,1-dimethylethyl)benzamide

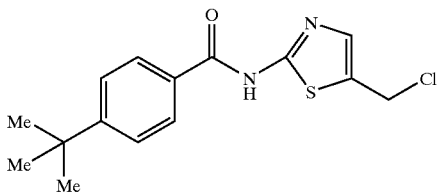

To a solution of 2-[[4-(1,1-dimethylethyl)phenyl)carbonyl]amino]-5-hydroxymethylthiazole (1.50 g, 5.16 mmol) in dichloromethane (40 mL) was added thionyl chloride (1.50 mL, 20.6 mmol) at 0° C. The mixture was stirred for 2 h, after which the reaction was complete, as indicated by HPLC. Evaporation of solvent and excess thionyl chloride provided the desired material (1.58 g, 99%) as a pale yellow solid.

B. 5-[[[2-[[4-(1,1-Dimethylethyl)benzoyl]amino]thiazol-5-yl]methyl]thio]-2-methylbenzoic acid

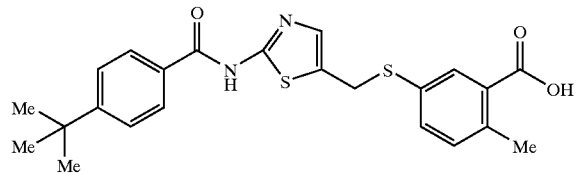

To a solution of 3-mercapto-2-methylbenzoic acid (0.270 g, 1.60 mmol) in DMF (5 mL) was added KOBu$^r$(0.378 g, 3.20 mmol) at 0° C. The mixture was stirred at 0° C. for 20 min before 5-chloromethyl-2-[[4-(1,1-dimethylethyl)phenyl)carbonyl]-amino]thiazole (0.445 g, 1.44 mmol) was added. The mixture was stirred at 0° C. for 1 h and then poured into water (20 mL). The solution was acidified to pH 2 using 1 N HCl. The precipitate was collected by filtration and dried over drierite under vacuum. The product (0.489 g, 77%) was obtained as a white solid: LC/MS RT=3.96 min; mass spectrum (M+H)$^+$=441.14.

C. 4-(1,1-Dimethylethyl)-N-[5-[[[3-[[4-(2-pyrimidinyl)piperazin-1-yl]carbonyl]-4-methylphenyl]thio]methyl]thiazol-2-yl]benzamide

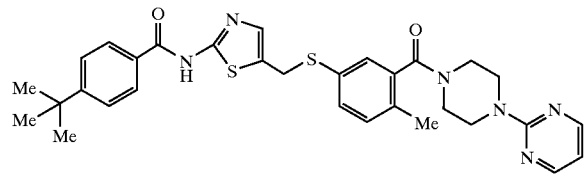

A mixture of the product of Example 32, part B (0.250 g, 0.567 mmol), 1-(2-pyrimidyl)piperazine (0.121 g, 0.737 mmol), benzotriazol-1-yloxytris(dimethylamino)phosphoniumhexafluorophosphate (0.476 g, 1.08 mmol), 4-methylmorpholine (0.31 mL, 2.82 mmol) in DMF (6 mL) was heated at 65° C. for 5 h. The mixture was then diluted with ethyl acetate, washed with water, 1 N NaOH solution, water, and brine. The solution was dried over anhydrous MgSO$_4$ and concentrated under vacuum. The residue was purified using flash column chromatography (ethyl acetate) to provide the desired product (0.210 g, 63%) as a white solid: LC/MS RT=3.94 min; mass spectrum (M+H)$^+$=587.42.

EXAMPLE 33

N-[5-[[N-[3-[(4-Acetylpiperazin-1-yl)carbonyl]phenylmethyl]-N-methylamino]methyl]thiazol-2-yl]-4-(1,1-dimethylethyl)benzamide

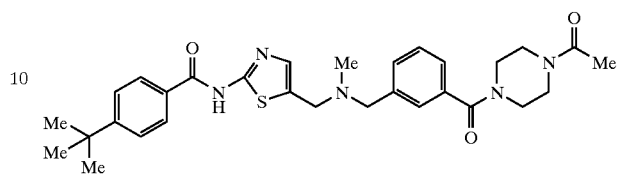

A. 4-Acetyl-1-[3-[(N-methylamino)methyl]benzoyl]piperazine

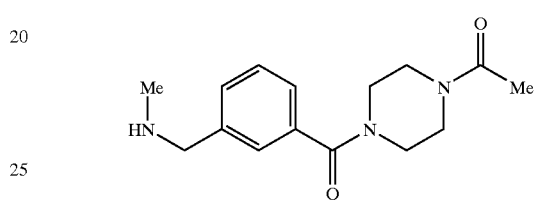

To N-Acetylpiperazinyl-(3-chloromethyl)benzamide (32C, 0.884 g, 3.15 mmol) was added methylamine (2.0 M in MeOH, 4.7 mL). The mixture was stirred at room temperature overnight. It was then diluted with water (20 mL), adjusted to pH 11 using 10% NaCO$_3$ solution, and extracted with ethyl acetate (5×30 mL). The combined organic extract was dried over anhydrous MgSO$_4$ and concentrated under vacuum. The residue was purified using flash column chromatography (30% MeOH/CHCl$_3$-80% MeOH/CHCl$_3$) to afford the desired amine (0.142 g, 16%) as a pale yellow viscous oil; LC/MS RT=1.42 min, mass spectrum (M+H)$^+$=276.23.

B. N-[5-[[N-[3-[(4-Acetylpiperazin-1-yl)carbonyl]phenylmethyl]-N-methylamino]methyl]thiazol-2-yl]-4-(1,1-dimethylethyl)benzamide

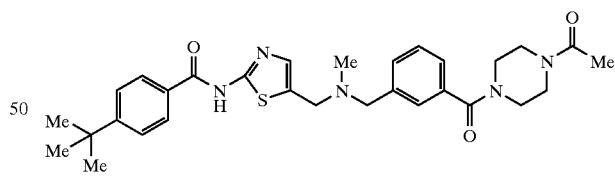

To a solution of 33A (72.0 mg, 0.261 mmol) in THF (3 mL) was added 5-chloromethyl-2-[[4-(1,1-dimethylethyl)phenyl)carbonyl]amino]thiazole (32A, 80.0 mg, 0.259 mmol) in one portion at 0° C. The mixture was stirred room temperature for 3h and then at 45° C. for 2 h. It was then diluted with water (20 mL), adjusted to pH 11 using 10% NaCO$_3$ solution, and extracted with ethyl acetate (5×30 mL). The combined extract was dried over anhydrous MgSO$_4$ and concentrated in vacuo. The residue was purified using preparative HPLC to afford 13.3 mg of the desired material as a TFA salt; LC/MS RT=2.60 min, mass spectrum (M+H)$^+$=548.28.

EXAMPLE 34

N-[5-[[3-[(4-Acetylpiperazin-1-yl)carbonyl]-4-methyl-6-methoxy-phenyl]thio]thiazol-2-yl]-4-(N-1,2-dimethylpropylaminomethyl)benzamide

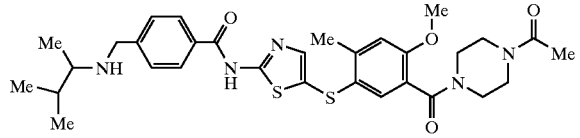

A. [3-[(2-Aminothiazol-5-yl)thiol]-4-methyl-6-methoxy]benzoic acid

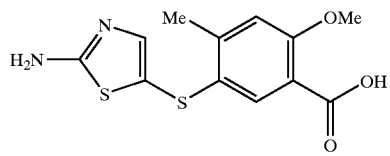

A 4.37 M solution of sodium methoxide in methanol (33.7 mL, 147.3 mmol) was added dropwise to a stirred suspension of 2-amino-5-bromothiazole hydrobromide (9.96 g, 38.3 mmol) and 3-carboxy-4-methoxy-6-methyl-thiophenol (5.84 g, 27.5 mmol) in methanol (95 mL) at 0–5° C. under argon. The cooing bath was removed and the solution was stirred at rt. for 1 hr. The mixture was cooled to 0° C. and acidified with a 4 M solution of hydrogen chloride in dioxane (37 mL, 148 mmol). Supplemental hydrogen chloride in dioxane was added slowly to adjust the pH to 2. Precipitated salts were filtered and washed with methanol. The filtrate was concentrated under reduced pressure and the residual solid was washed with water (2×15 mL). The solid was dried in vacuo, and triturated with ether to obtain the titled compound (8.52 g, 87%) as a tan solid.

B. 5-[[[3-[(4-Acetylpiperazin-1-yl)carbonyl]-4-methyl-6-methoxy]phenyl]thio]-2-amino-thiazole

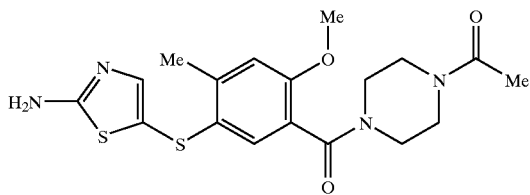

A suspension of [3-[(2-aminothiazol-5-yl)thio]-4-methyl-6-methoxy]benzoic acid (2 g, 6 mmol), N-acetylpiperazine (3.1 g, 24 mmol), ethyl-3-(3-dimethylamino)propyl carbodiimide hydrochloride (2.3 g, 12 mmol), 1-hydroxy-7-azabenzotriazole (980 mg, 7.2 mmol) and diisopropylethylamine (4.2 mL, 24 mmol) in THF (50 mL) and DMF (6 mL) was heated to 64° C. for 2.25 hr. The mixture was cooled to rt. and concentrated in vacuo. The residue was dissolved in dichloromethane and washed with water (50 mL) and 1 N aq. HCl solution (4×100 mL). The aqeous layers were combined, brought to slightly alkaline pH using 1 N aq. NaOH solution and extracted with dichloromethane (6×70 mL). The dichloromethane extracts were combined, dried (Na$_2$SO$_4$), filtered, and concentrated. The residue was triturated with ether (90 mL) to obtain the tided product (1.99 g, 82%) as a light tan solid.

C. N-[5-[[[3-[(4-Acetylpiperazin-1-yl)carbonyl]-4-methoxy-6-methyl]phenyl]thio]thiazol-2-yl]-4-(chloromethyl)benzamide

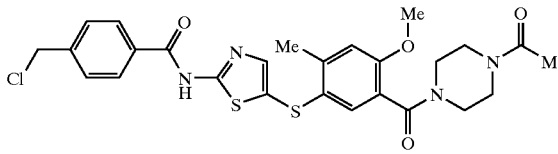

A solution of 5-[[[3-[(4-acetylpiperazin-1-yl)carbonyl]methyl-6-methoxylpheny]thio]-2-aminothiazole (102 mg, 0.28 mmol), 4-chloromethyl-benzoyl chloride (53 mg, 0.28 mmol) and diisopropylethyl amine (140 µL, 1 mmol) in dichloromethane (8 mL) was stirred at rt. for 3 hr. Supplemental 4-chloromethylbenzoyl chloride (26 mg, 0.14 mmol) was added and the solution was stirred for an additional 4 hr. The mixture was diluted with dichloromethane (40 mL) and washed with 1 N aq. HCl solution (2×10 mL) and aq. NaHCO$_3$ solution (2×15 mL). The dichloromethane extract was dried (MgSO$_4$), filtered, and concentrated in vacuo to obtain the crude tided product (205 mg) as a yellow foam.

D. N-[5-[[3-[(4-Acetylpiperazin-1-yl)carbonyl]-4-methyl-6-methoxy-phenyl]thio]thiazol-2-yl]-4-(N-1,2-dimethylpropylaminomethyl)benzamide

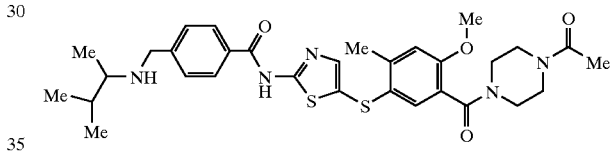

A solution of crude N-[5-[[[3-[(4-acetylpiperazin-1-yl)carbonyl]-4-methoxy-6-methyl]phenyl]thio]thiazol-2-yl]-4-(chloromethyl)benzamide (205 mg, 0.25 mmol) and 1,2-dimethylpropyl amine (87 mg, 1 mmol) in methanol (10 mL) was heated to 60° C. in a sealed tube for 24 hr. The mixture was cooled to rt. and concentrated in vacuo. The residue was purified using reverse phase automated preparative HPLC (conditions: YMC S5 ODS 30×250 mm column, 30 min gradient starting from solvent A (10% MeOH, 90% H$_2$O, 0,1% TFA) to solvent B (90% MeOH, 10% H$_2$O, 0,1% TFA), flow rate 25 mL/min, λ=220 nM) to obtain the titled compound as a TFA salt (100 mg, 55% yield over two steps, white foam); LC/MS RT=2.79 min; mass spectrum (M+H)$^+$=610.32.

EXAMPLE 35

4-Acetyl-1-[5-[[2-[N-(6-bromopyridin-2-yl)amino]thiazol-5-yl]oxo]-2-methylbenzoyl]piperazine

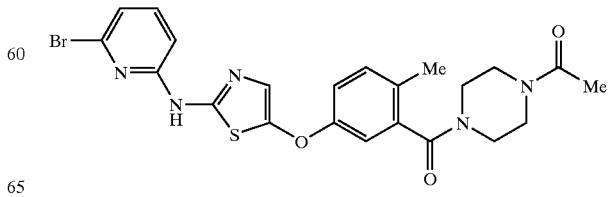

A. 5-[[2-[N-(6-Bromopyridin-2-yl)amino]thiazol-5-yl]oxo]-2-methylbenzoic acid ethyl ester

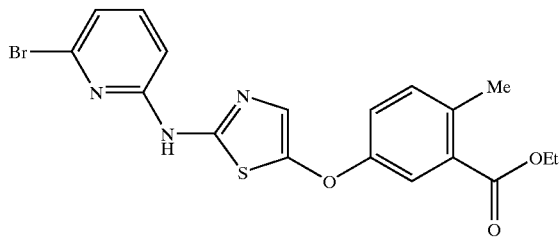

A suspension of 2-[(6-bromo-2-pyridinyl)amino]-5-bromothiazole (Example 2, part D: 400 mg, 1.19 mmol), ethyl 3-hydroxy-6-methylbenzoate (330 mg, 1.79 mmol) and cesium carbonate (1.6 g, 4.76 mmol) in acetone (16 mL) was heated under reflux for 16 hr. The mixture was cooled to rt. and cesium carbonate was filtered through a Whatman Autovial PTFE filter. The filtrate was concentrated, diluted with dichloromethane and filtered. The filtrate was concentrated and the residual brown oil was purified using silica gel column chromatography. Elution with 5% EtOAc in hexanes followed by 10%, 20%, 30%, and 50% EtOAc in hexanes afforded the title product (90 mg, 21%) as a light tan solid.

B. 5-[[2-[N-(6-Bromopyridin-2-yl)amino]thiazol-5-yl]oxo]-2-methylbenzoic acid

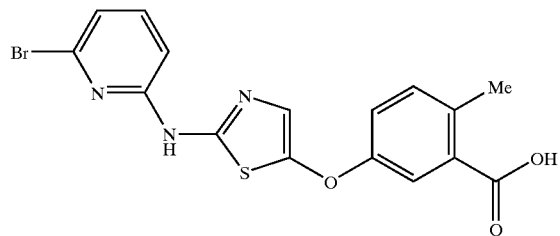

A solution of 5-[[2-[N-(6-bromopyridin-2-yl)amino]thiazol-5-yl]oxo]-2-methylbenzoic acid ethyl ester (90 mg, 0.21 mmol) and 1 N aq. NaOH solution (1.3 mL, 1.3 mmol) in THF (2 mL) and ethanol (2 mL) was stirred at rt. for 24 hr. The mixture was cooled to 0° C. and acidified with 6 N aq. HCl solution. After eveporation of the solvents in vacuo, the residue was diluted with water and the precipitate was filtered, washed with water, and dried in vacuo to obtain the titled compound (57 mg, 67%) as a yellow solid.

C. 4-Acetyl-1-[5-[[2-[N-(6-bromopyridin-2-yl)amino]thiazol-5-yl]oxo]-2-methylbenzoyl]piperazine

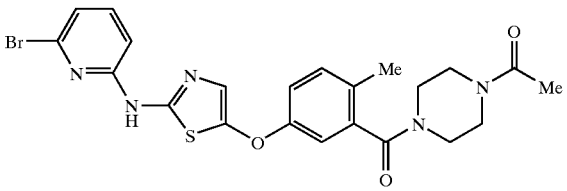

A suspension of 5-[[2-[N-(6-bromopyridin-2-yl)amino]thiazol-5-yl]oxo]-2-methylbenzoic acid (27.9 mg, 0.07 mmol), N-acetylpiperazine (17.9 mg, 0.14 mmol), ethyl-3-(3-dimethylamino)propyl carbodiimide hydrochloride (26.8 mg, 0.14 mmol), 1-hydroxy-7-azabenzotriazole (11.3 mg, 0.08 mmol) and diisopropylethylamine (37 μL, 0.21 mmol) in THF (2.3 mL) and DMF (0.4 mL) was heated to 60° C. for 3.25 hr. The mixture was cooled to rt. and concentrated in vacuo on a speed vac. The residue was purified using silica gel column chromatography (5% acetone in dichloromethane followed by 1% and 2% methanol in dichloromethane) to afford the titled product (34 mg, 75%) as a light tan solid: LC/MS RT=1.90 min; mass spectrum (M+H)⁺=516.45.

EXAMPLE 36

4-Acetyl-1-[5-[[2-[N-(6-chloro-2-methyl-pyrimidin-4-yl)amino]thiazol-5-yl]thiol-2-methoxy-4-methylbenzoyl]piperazine

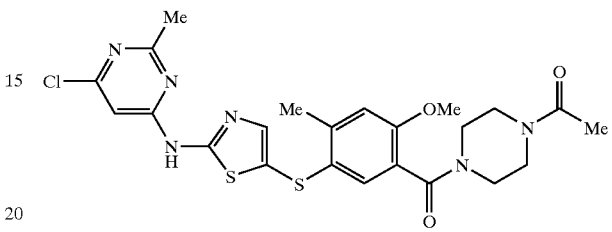

Sodium hydride (43.9 mg, 1.83 mmol) was added to a solution of 5-[[[3-[(4-acetylpiperazin-1-yl)carbonyl]-4-methyl-6-methoxy]phenyl]thio]-2-aminothiazole (Example 34, part B: 250 mg, 0.61 mmol) and 2-methyl-4,6-dichloropyrimidine (200 mg, 1.23 mmol). The mixture was heated to 50° C. for 16 hr, cooled to rt, and supplemental sodium hydride (43.9 mg, 1.83 mmol) was added. The mixture was heated to 50° C. for an additional 3 hr, cooled to rt, and excess hydride was quenched by the addition of glacial acetic acid. The mixture was concentrated in vacuo, diluted with satd. aq. NaHCO₃ solution, and extracted with THF-EtOAc mixture (4×). The organic extracts were combined, washed with satd. aq. NaHCO₃ solution, brine, dried (NaSO₄), filtered, and concentrated in vacuo to obtain a tan solid which was triturated with ether-EtOAc (4:1) to obtain the titled compound (260 mg, 80%) as a light tan solid.

EXAMPLE 37

4-Acetyl-1-[5-[[2-(6-N,N-dimethylaminoethylamino-2-methyl-pyrimidin-4-yl)amino]thiazol-5-yl]thio]-2-methoxy-4-methylbenzoyl]piperazine

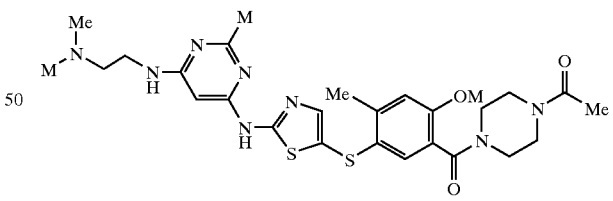

A solution of 4-acetyl-1-[5-[[2-[N-(6-chloro-2-methyl-pyrimidin-4-yl)amino]thiazol-5-yl]thio]-2-methoxy-4-methylbenzoyl]piperazine (Example 36: 10 mg, 0.019 mmol), N,N-dimethylethylenediamine (10 μL; 0.094 mmol), and 4-dimethylaminopyridine (2.32 mg, 0.019 mmol) in dioxane (1 mL) was heated to 100° C. in a sealed vial for 16 hr. The mixture was purified using reversed phase automated preparative HPLC (conditions: YMC 20×100 mm column, 10 min gradient starting from 90% solvent A (10% MeOH, 90% H₂O, 0.1% TFA) and 10% solvent B (90% MeOH, 10% H₂O, 0,1% TFA) and final solvent:90% solvent B and 10% solvent A, flow rate 20 mL/min, λ=220 nM) to obtain the titled compound as a TFA salt (14 mg, 36% yield, tan solid): LC/MS RT=1.34 min; mass spectrum (M+H)$^+$=585.16.

EXAMPLE 38

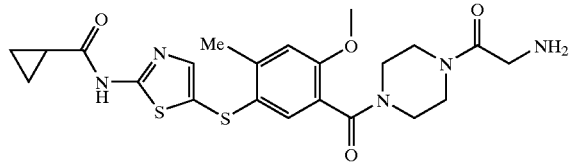

A. 2-Amino-5-[(5-carbomethoxy-4-methoxy-2-methylphenyl)thio]thiazole

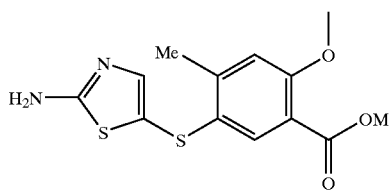

To a suspension of the compound described in Example 34, part A (2.00 g, 6.75 mmol) in MeOH (100 mL) was added HCl in diethyl ether (2.0 M, 10 mL) at rt. The mixture was heated at reflux overnight before MeOH was removed under vacuum. To the residue was added water (50 mL). The resulting mixture was adjusted to pH 12 with 1 N NaOH solution and then extracted with EtOAc (4×40 mL). The combined extract was washed with water and brine, and dried over anhydrous MgSO$_4$. Evaporation of solvent under vacuum provided the titled compound (1.73 g, 82% yield) as a tan solid.

B. 2-[[(Cyclopropyl)carbonyl]amino]-5-[(5-carbomethoxy-4-methoxy-2-methylphenyl)thio]thiazole

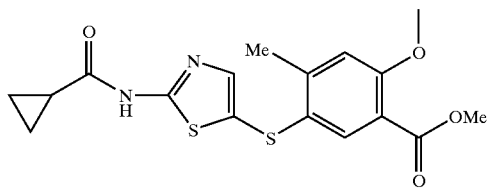

A mixture of the compound from part A (1.73 g, 5.57 mmol), cyclopropylcarboxylic acid (95%,0.69 mL, 8.28 mmol), 1-[(3-dimethylamino)propyl]-3-ethylcarbodiimide hydrochloride (1.90 g, 9.91 mmol), and 4-dimethylaminopyridine (0.070 g, 0.57 mmol) in CH$_2$Cl$_2$ (120 mL) was heated at reflux overnight. The mixture was cooled to rt, diluted with CH$_2$Cl$_2$ (50 mL), and washed with water, 1 N HCl solution, 1 N NaOH solution, water, and brine. The organic fraction was then dried over anhydrous MgSO$_4$. Evaporation of solvent under vacuum provided the titled compound (1.91 g, 90% yield) as a beige solid.

C. 2-[[(Cyclopropyl)carbonyl]amino]-5-[(5-carboxy-4-methoxy-2-methylphenyl)thio]thiazole

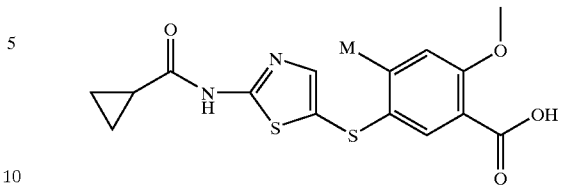

A mixture of the compound from part B (0.550 g, 1.45 mmol) and 1 N NaOH (4.4 mL, 4.4 mmol) in THF (20 mL) was heated at reflux for 5 hr. Solvent was removed under vacuum, and the residue was acidified to pH 2 with 1 N HCl. The resulting precipitate was collected by suction filtration, washed with water, and dried over drierite under vacuum to afford the titled compound (0.484 g, 92% yield) as a beige solid.

D. 2-[[(Cyclopropyl)carbonyl]amino]-5-[(4-methoxy-2-methyl-5-piperazinylcarboamidophenyl)thio]thiazole

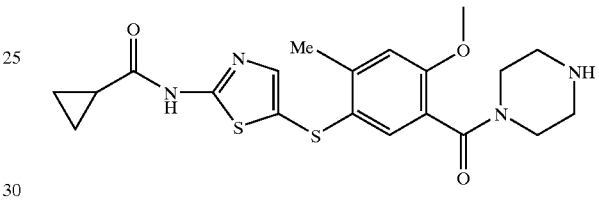

A solution of the compound from part C (0.252 g, 0.690 mmol.), piperazine (0.300 g, 3.60 mmol), (benzotriazol-1-yloxy)tris(dimethylamino)phosphonium hexafluorophosphate (BOP, 0.622 g, 1.40 mmol) and N-methylmorpholine (0.38 mL, 3.5 mmol) in DMF (7.0 mL) was heated in an oil bath at 65° C. for 2 hr. After cooling to room temperature, the reaction mixture was diluted with EtOAc and washed with water (2×). The organic layer was dried over sodium sulfate, filtered, and concentrated in vacuo to give the first crop of product (0.0805 g, 27% yield). The aqueous layers were combined and extracted with dichloromethane (5×). The organic layers were combined, dried over sodium sulfate, filtered and concentrated in vacuo. Silica gel chromatography using dichloromethane:methanol:acetic acid (10:0.4:0.2) as eluent afforded the second crop of product (0.1860 g, 62% yield) as a white solid: LC/MS (M+H)$^+$= 433.56.

E. 2-[[(Cyclopropyl)carbonyl]amino]-5-[[(4-methoxy-2-methyl-5-[[(4-tert-butoxycarbonylamino)aceto]piperazinylcarboxamido]phenyl]thio]thiazole

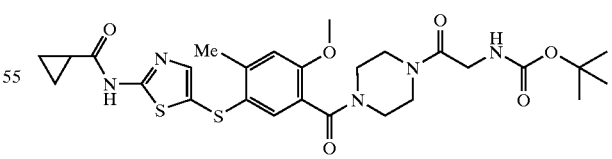

A mixture of the compound from part D (46.5 mg, 0.107 mmol), N-Boc-glycine (38.5 mg, 0.22 mmol), BOP (92.9 mg, 0.21 mmol), and N-methylmorpholine (0.060 mL, 0.55 mmol) in DMF (0.5 mL) was mechanically shaken at 65° C. overnight. The reaction mixture was diluted with MeOH (0.5 mL), purified using preparative HPLC and lyophilized to give the titled compound (51.6 mg, 82% yield) as a white powder.

F. Title Compound

To a solution of the compound from part E (40.1 g, 0.068 mmol) in dichloromethane (1.0 mL) under nitrogen at 0° C. was added trifluoroacetic acid (1.0 mL). After 3 hr, the reaction mixture was concentrated in vacuo and triturated with diethyl ether to give the desired product (30.8 mg, 75% yield) as a white solid: LC/MS (M+H)$^+$=490.21.

EXAMPLE 39

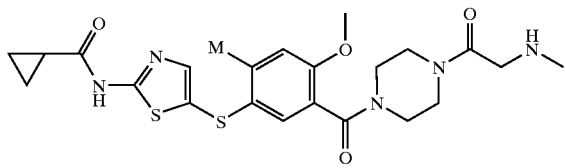

A mixture of 2-[[(cyclopropyl)carbonyl]amino]-5-[(4-methoxy-2-methyl-5-piperazinylcarboamidophenyl)thio] thiazole (Example 38, part D: 46.5 mg, 0.107 mmol), N-methylglycine (19.6 mg, 0.22 mmol), BOP (92.9 mg, 0.21 mmol), and N-methylmorpholine (0.060 ml, 0.55 mmol) in DMF (0.5 mL) was mechanically shaken at 65° C. overnight. The reaction mixture was diluted with MeOH (0.5 mL), purified using preparative HPLC, and lyophilized to give the title compound as a white powder TFA salt (27.3 mg, 41% yield): LC/MS (M+H)$^+$=504.14.

EXAMPLE 40

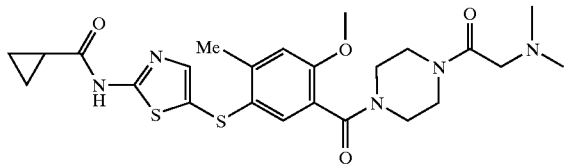

This material was prepared in the same manner as Example 39: LC/MS (M+H)$^+$=518.22.

EXAMPLE 41

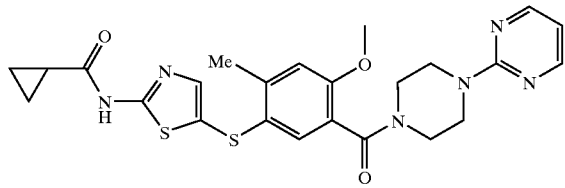

A mixture of 2-[[(cyclopropyl)carbonyl]amino]-5-[(4-methoxy-2-methyl-5-piperazinylcarboamidophenyl)thio] thiazole (Example 38, part D: 20.0 mg, 0.0549 mmol), 1-(2-pyrimidyl)piperazine (18.0 mg, 0.10 mmol), BOP (36.4 mg, 0.0823 mmol), and N-methylmorpholine (0.027 mL, 0.246 mmol) in DMF (0.5 mL) was stirred at 55° C. overnight. The reaction mixture was diluted with MeOH (0.5 mL) and purified using preparative HPLC. The appropriate fractions were combined and concentrated, and the pH adjusted to 12 with 1 N NaOH followed by extraction with $CH_2Cl_2$ (3×20 mL). The combined extract was dried over anhydrous $MgSO_4$. Evaporation of solvent under vacuum provided the desired product (20 mg, 71% yield) as a white solid: LC/MS (M+H)$^+$=511.17.

EXAMPLE 42

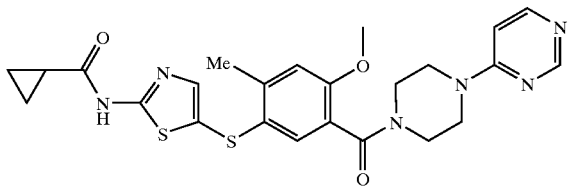

This material was prepared in the same manner as Example 41: LC/MS (M+H)$^+$=511.15.

EXAMPLE 43

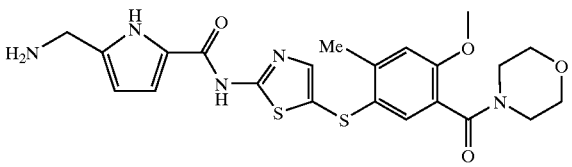

A. 2-Amino-5-[(4-methoxy-2-methyl-5-[[(morpholinyl) carboxamido]phenyl]thio]thiazole

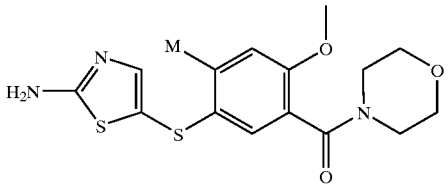

A mixture of 2-Amino-5-[(5-carboxy-4-methoxy-2-methylphenyl)thio]thiazole (Example 34, part A: 1.00 g, 3.37 mmol), morpholine (0.59 mL, 6.74 mmol), BOP (2.24 g, 5.06 mmol), and N-methylmorpholine (1.60 mL, 14.6 mmol) in DMF (10 mL) was heated at 60° C. for 2.5 hr. The solution was diluted with EtOAc (150 mL), then washed with water (3×40 mL) and brine (40 mL). The aqueous layer was extracted with EtOAc (2×50 mL) and the combined organic layer was dried over anhydrous $MgSO_4$. The solution was concentrated under vacuum, and the residue purified using flash chromatography (silica gel, 6% MeOH/ $CHCl_3$) to give the titled compound (0.935 g, 76% yield) as a tan solid.

B. 2-[[(5-Formyl-2-pyrolyl)carbonyl]amino]-5-[[(morpholinyl)carboxamido]phenyl]thio]thiazole

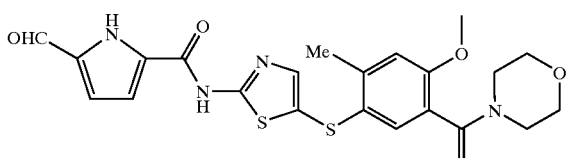

To a suspension of 5-formyl-2-pyrrole carboxylic acid (0.320 g, 2.30 mmol) in $CH_2Cl_2$ (25 mL) at ° C. was added thionyl chloride, and the resulting mixture heated at reflux for 1.5 hr. The solvent and excess thionyl chloride was evaporated under vacuum. Residual thionyl chloride was removed by adding toluene (1 mL) and concentrating the mixture to dryness under vacuum. The residue was dissolved in $CH_2Cl_2$ (25 mL), and to the resulting solution was added a solution of the compound of part A (0.927 g, 2.54 mmol) and pyridine (1.1 mL, 13.6 mmol) in CH$_2$Cl$_2$ (30 mL). The mixture was heated at reflux for 2.5 hr before it was concentrated to dryness under vacuum. To the solid residue was added 0.5 N HCl (40 mL) and the mixture was well stirred for 10 min. The precipitate was collected by suction filtration, washed with water, and dried over drierite under vacuum to give the title compound (0.880 g, 71% yield) as a tan solid.

C. 2-[[(5-Hydroxymethyl-2-pyrrolyl)carbonyl]amino]-5-[[[(morpholinyl)carboxamido]phenyl]thio]thiazole

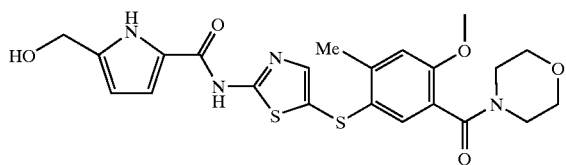

To a suspension of the compound from part B (0.400 g, 0.822 mmol) in DMF (40 mL) and MeOH (20 mL) was added NaBH$_4$ (0.622 g, 16.4 mmol) at 0° C. in one portion. The mixture was stirred at rt. overnight, after which period the heterogeneous mixture became a clear solution. The reaction was quenched with water (5 mL), and the resulting solution was concentrated to approximately 20 mL. The residue was diluted with water (40 mL), extracted with EtOAc (3×40 mL) and CH$_2$Cl$_2$ (3×40 mL). The combined organic layer was concentrated under vacuum. To the residue was added Et$_2$O (20 mL). The resulting precipitate was collected by filtration, washed with water, and dried over drierite under vacuum to provide the title product (0.226 g, 56% yield) as a beige solid.

D. Title Compound

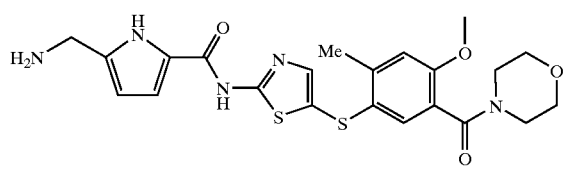

A mixture of the compound from part C (80 mg, 0.164 mmol) and thionyl chloride (2 mL) was heated at 60° C. for 1.5 hr. The excess thionyl chloride was evaporated under vacuum. Residual thionyl chloride was removed by adding toluene (1 mL) and concentrating the mixture to dryness under vacuum. The residue was dissolved in anhydrous DMF (2 mL), and to the resulting solution was added NH$_3$/MeOH (7 M solution, 7 mL, 7 mmol). The mixture was heated in a sealed tube at 55° C. for 16 hr. After cooling to rt, the reaction mixture was poured into 1 N HCl solution (15 mL). The resulting mixture was extracted with EtOAc (3×20 mL). The aqueous solution was adjusted to pH 12 with 10% NaOH solution, and extracted with EtOAc (4×30 mL). The combined extract was dried over anhydrous MgSO$_4$, and concentrated under vacuum. The residue was purified using preparative HPLC and lyophilized to provide the titled product (3.0 mg, 3% yield) as a white powder, TFA salt: LC/MS (M+H)$^+$=488.14.

EXAMPLE 44

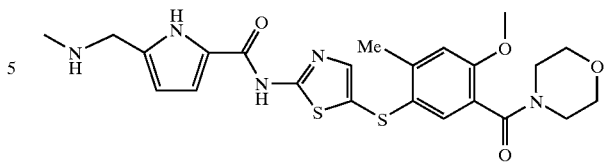

To a mixture of the compound of Example 43, part B (40 mg, 0.082 mmol) and MeNH$_2$/THF (2.0 M solution, 0.16 mL, 0.32 mmol) in anhydrous DMF (8 mL) at rt. was added NaBH(OAc)$_3$ (71 mg, 0.32 mmol) in one portion. The mixture was stirred at rt. for 6 hr before supplementary NaBH(OAc)$_3$ (35 mg, 0.16 mmol) was added. The mixture was allowed to stir at rt. overnight before it was quenched with saturated NaHCO$_3$ solution (10 mL). The mixture was then diluted with EtOAc (100 mL) and washed with water (3×25 mL). The aqueous solution was extracted with EtOAc (50 mL). The combined organic phase was washed with 10% LiCl solution (35 mL), and concentrated under vacuum. The residue was purified using preparative HPLC and lyophilized to provide the title product (22.7 mg, 45% yield) as a white powder, TFA salt: LC/MS (M+H)$^+$=502.17.

EXAMPLE 45

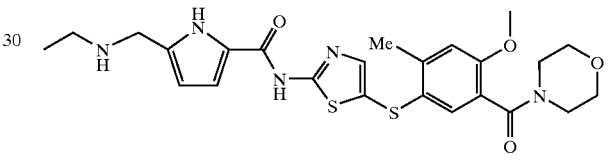

This material was prepared in a similar manner as Example 44: LC/MS (M+H)$^+$=516.2.

EXAMPLE 46

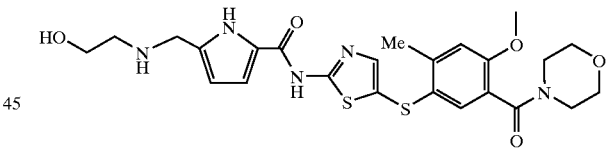

This material was prepared in the same manner as Example 44: LC/MS (M+H)$^+$=532.19.

EXAMPLE 47

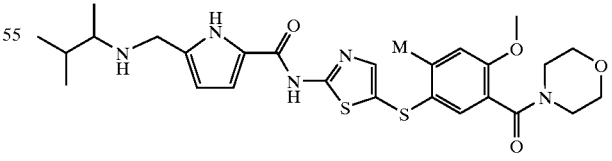

To a mixture of the compound from Example 43, part B (20 mg, 0.041 mmol) and 1,2-dimethylpropylamine (7.2 mg, 0.082 mmol) in anhydrous DMF (4 mL) at rt. was added NaBH(OAc)$_3$ (17 mg, 0.082 mmol) in one portion. The mixture was stirred at rt. for 20 hr before supplementary NaBH(OAc)$_3$ (26 mg, 0.12 mmol) was added. The mixture was allowed to stir at rt. for an additional 24 hr before it was quenched with saturated NaHCO₃ solution (10 mL). The resulting mixture was diluted with EtOAc, washed with water (2×) and brine, and concentrated under vacuum. The residue was dissolved in MeOH (5 mL), and to the resulting solution was added 1 N HCl (2 mL). The mixture was then heated at reflux for 1.5 hr. After cooling to rt, the solution was adjusted to pH 12 with 1N NaOH solution, diluted with water (5 mL), and extracted with EtOAc (3×). The combined extract was washed with brine and concentrated under vacuum. The residue was purified using preparative HPLC and lyophilized to provide the desired product (4.6 mg, 17% yield) as a white powder, TFA salt: LC/MS (M+H)⁺=558.34.

EXAMPLE 48

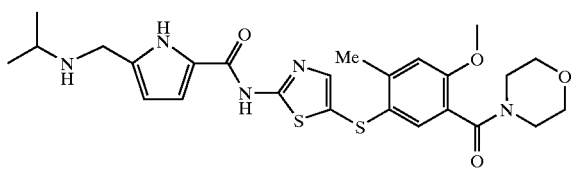

This material was prepared in the same manner as Example 44: LC/MS (M+H)⁺=530.37.

EXAMPLE 49

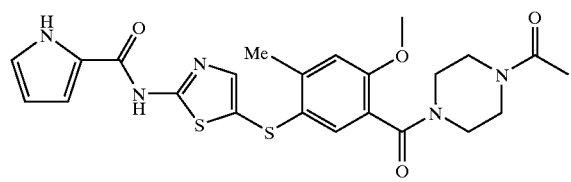

A mixture of 2-pyrrolecarboxylic acid (6.5 mg, 0.058 mmol) and thionyl chloride (0.8 mL, 11.0 mmol) was heated at 60° C. for 1.5 hr. The excess thionyl chloride was evaporated under vacuum. Residual thionyl chloride was removed by adding toluene (1 mL) and concentrating the mixture to dryness under vacuum. The residue was dissolved in CH₂Cl₂ (1.5 mL), and to the resulting solution was added the compound of Example 34, part B (20 mg, 0.049 mmol) in CH₂Cl₂ (1.5 mL), followed by the addition of pyridine (0.080 mL, 0.99 mmol). The mixture was heated at reflux for 2 hr before it was concentrated under vacuum. The residue was purified using preparative HPLC to give the desired product (20.5 mg, 84% yield) as a pale yellow solid: LC/MS (M+H)⁺=500.33.

EXAMPLE 50

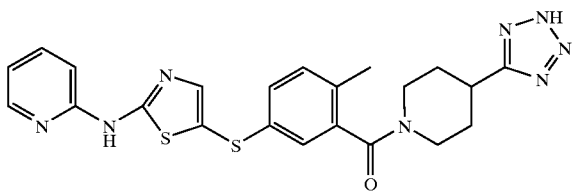

A.

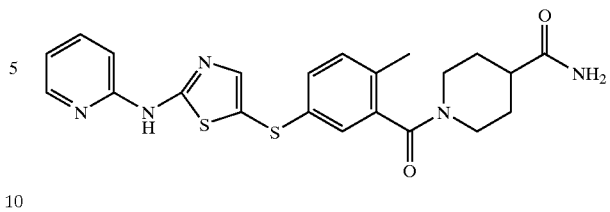

This compound was prepared from the compound described in Example 3, part E using previously described coupling conditions: LC/MS (M+H)⁺=452.3.

B.

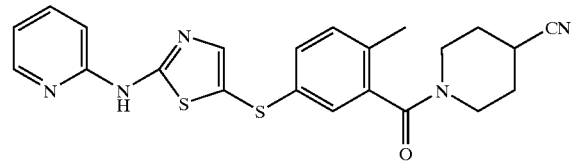

A mixture of the compound from part A (112 mg, 0.25 mmol), (methoxycarbonylsulfamoyl) triethylammoniumhydroxide, inner salt (150 mg, 0.63 mmol) and triethylamine (0.09 mL, 0.63 mmol) in THF (3 mL) was stirred for 2 hr at rt. After partitioning the reaction mixture between EtOAc (25 mL) and water (25 mL), the organic layer was washed with water (25 mL) and brine (25 mL). The organic layer was dried over MgSO₄ and concentrated to afford 88 mg (82%) of the titled compound as a white solid: LC/MS (M+H)⁺=436.37.

C.

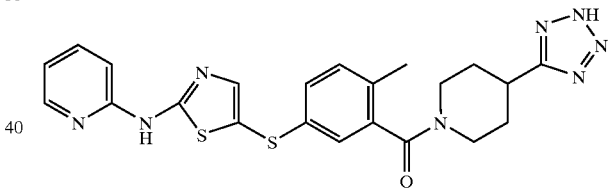

A mixture of the compound of part B (80 mg, 0.18 mmol) and tributyltin azide (150 mg, 0.45 mmol) in toluene (3 mL) was heated to 100° C. for 24 hr. A supplemental amount of tributyltin azide (150 mg, 0.45 mmol) was added and the mixture was heated at 100° C. for 24 hr. The reaction mixture was loaded onto a 1×5 cm silica gel column, which was eluted with 50 mL hexane, 50 mL of methylene chloride and 50 mL of 10% methanol/methylene chloride. Concentration of product containing fractions and trituration with ethyl ether afforded 12 mg (14%) of the titled compound as a tan solid: LC/MS (M+H)⁺=479.37.

EXAMPLE 51

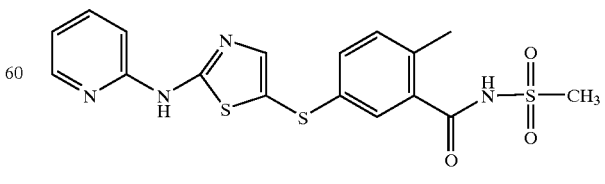

A mixture of the compound described in Example 3, part E (15 mg, 0.044 mmol), methanesulfonamide (5 mg, 0.05 mmol), EDCI (10 mg, 0.05 mmol) and 4-dimethylaminopyridine (7 mg, 0.055 mmol) in methylene chloride (0.5 mL) was stirred 48 hr at rt. The reaction mixture was partitioned between EtOAc (5 mL) and saturated potassium bisulfate solution (5 mL). After washing with water (5 mL) and brine (5 mL), the organic layer was dried over magnesium sulfate and concentrated to afford 11 mg (61%) of the titled compound as a white powder: MS $(M+H)^+=421.22$.

EXAMPLES 52–455

Using methods similar to those previously described, the following compounds 52 through 455 were synthesized.

| Ex. No. | Structure | MS (M + H)$^+$ |
|---|---|---|
| 52 | 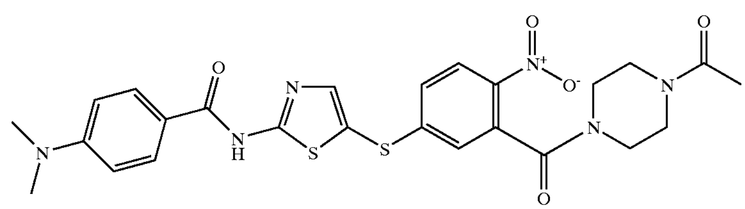 | 555.08 |
| 53 | 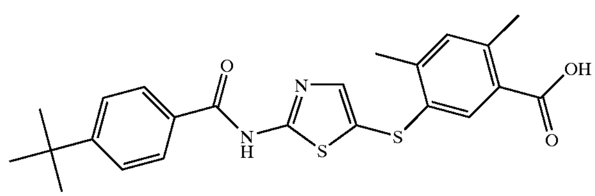 | 441.4 |
| 54 | 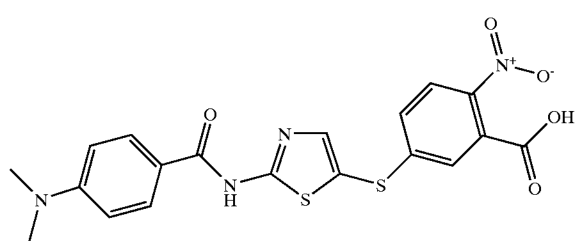 | 445.04 |
| 55 | 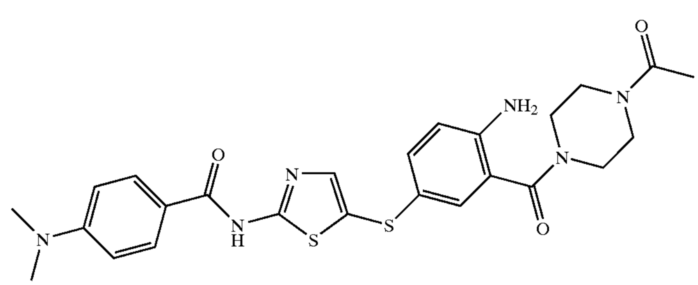 | 525.21 |
| 56 | 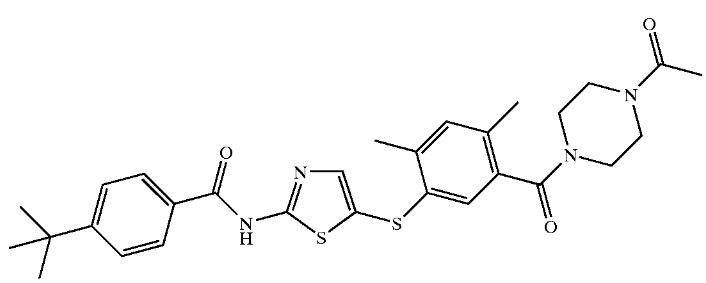 | 551.12 |

-continued

| Ex. No. | Structure | MS (M + H)+ |
|---|---|---|
| 57 | 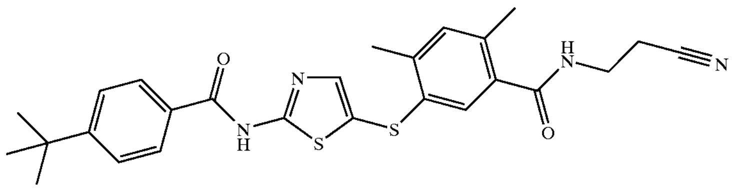 | 493.43 |
| 58 | 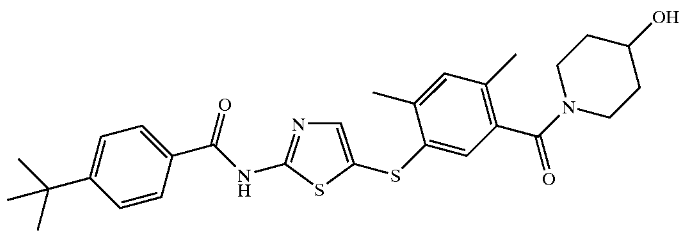 | 524.32 |
| 59 | 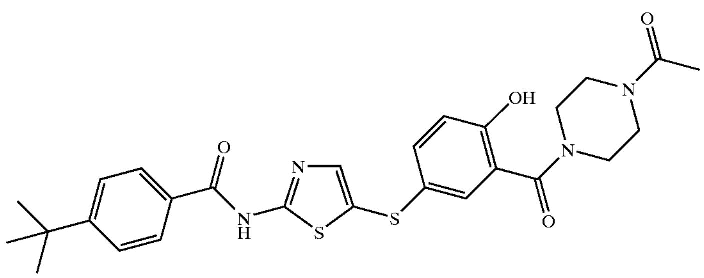 | 539.28 |
| 60 | 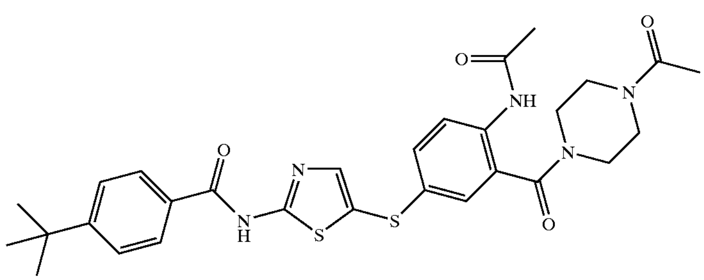 | 580.38 |
| 61 | 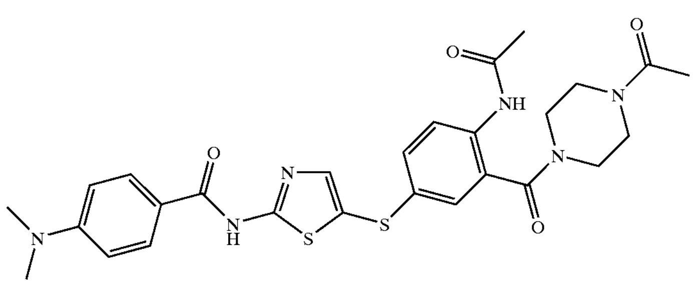 | 567.16 |
| 62 | 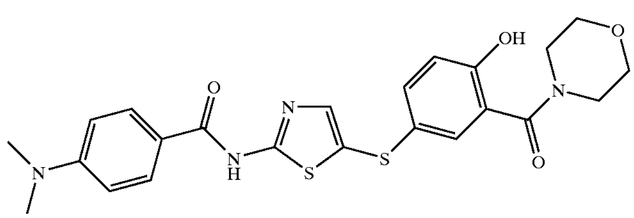 | 485.34 |

| Ex. No. | Structure | MS (M + H)+ |
|---|---|---|
| 63 | 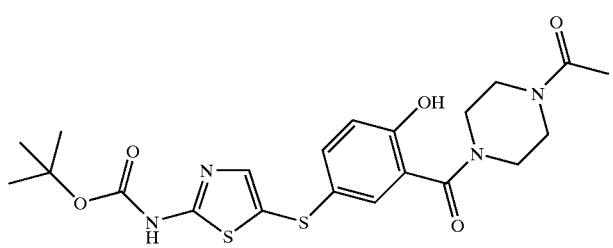 | 479.37 |
| 64 | 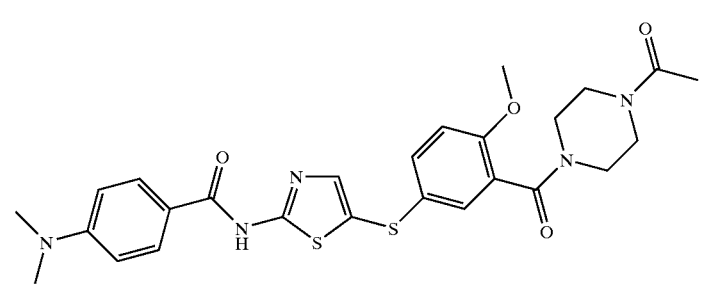 | 540.14 |
| 65 | 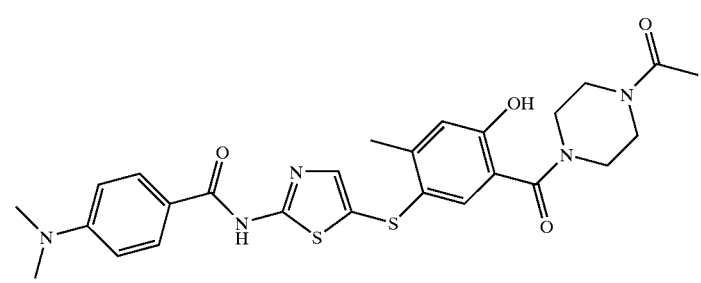 | 540.53 |
| 66 | 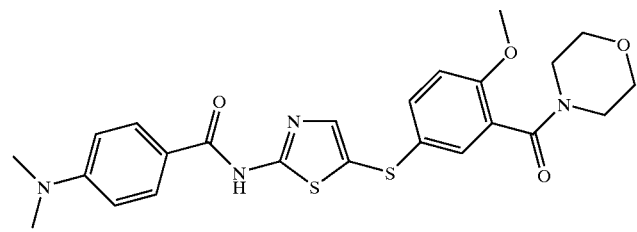 | 499.45 |
| 67 | 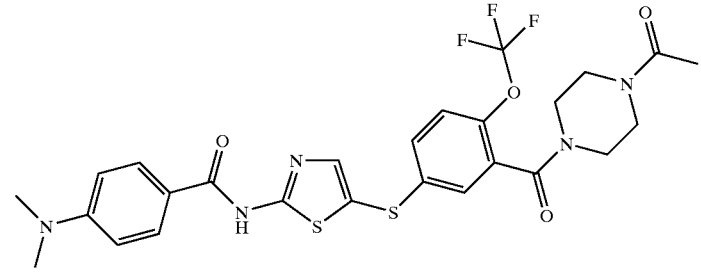 | 594.36 |

-continued
| Ex. No. | Structure | MS (M + H)+ |
|---|---|---|
| 68 | 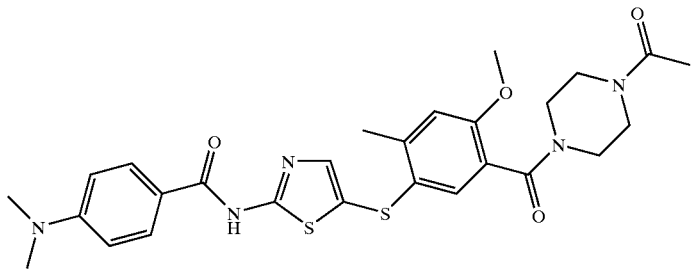 | 554.31 |
| 69 | 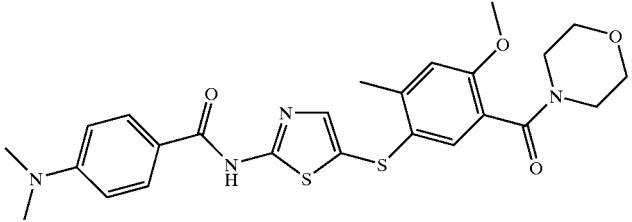 | 513.27 |
| 70 | 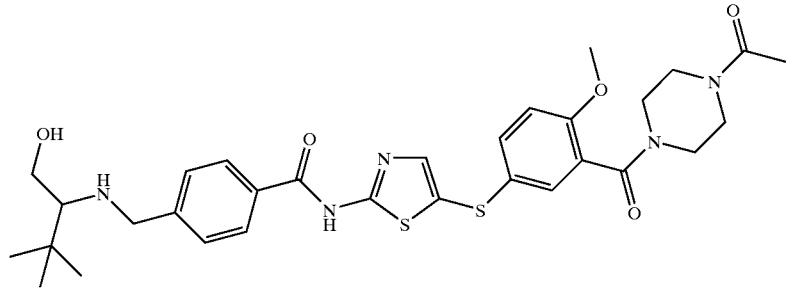 | 626.45 |
| 71 | 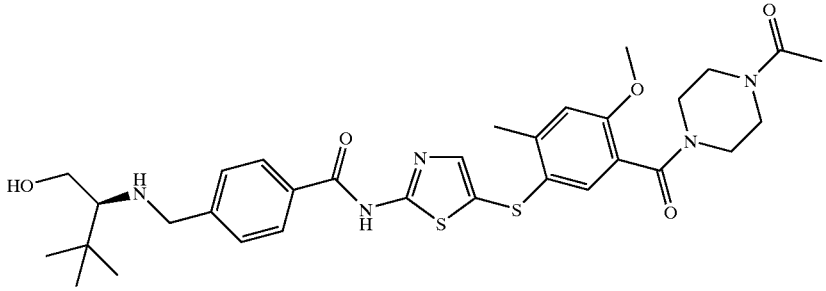 | 640.32 |
| 72 | 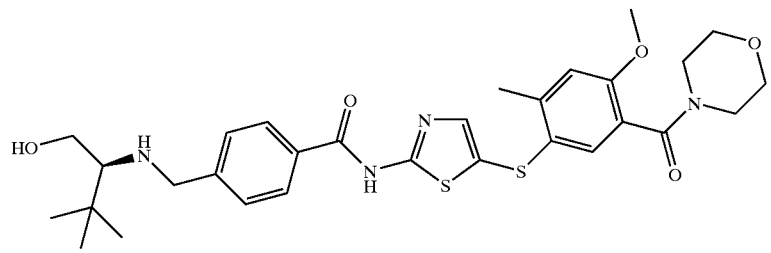 | 599.29 |

-continued

| Ex. No. | Structure | MS (M + H)+ |
|---|---|---|
| 73 | 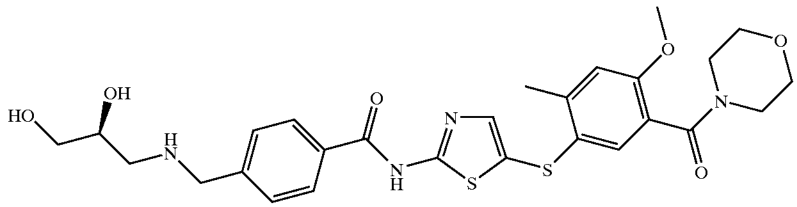 | 573.28 |
| 74 | 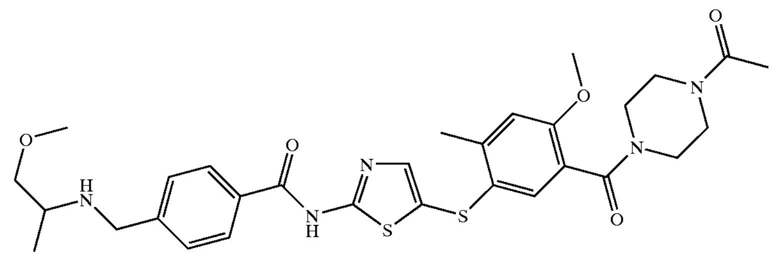 | 612.46 |
| 75 | 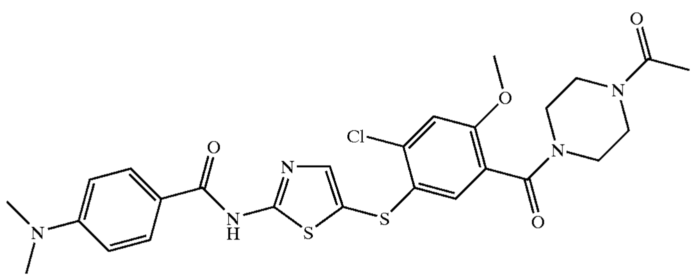 | 574.38 |
| 76 | 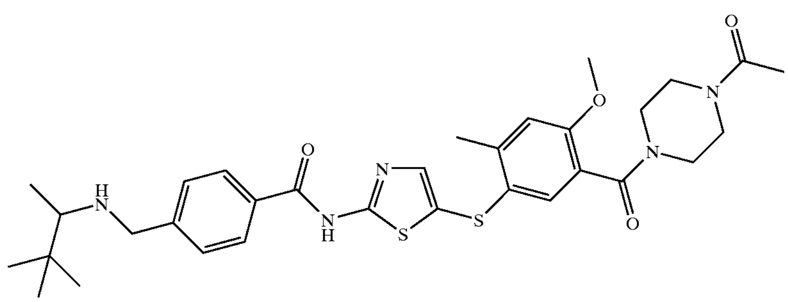 | 624.39 |
| 77 | 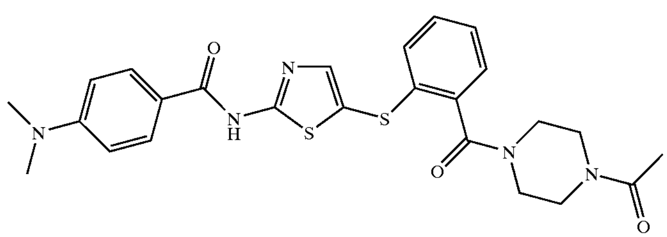 | 510.43 |
| 78 | 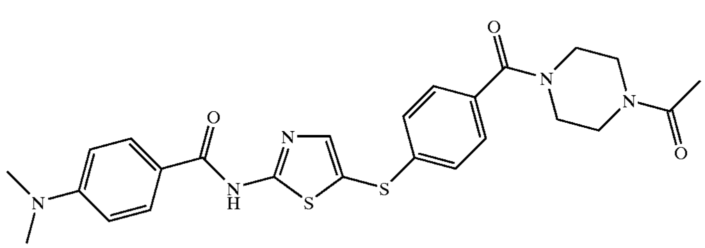 | 510.34 |

-continued

| Ex. No. | Structure | MS (M + H)+ |
|---|---|---|
| 79 | 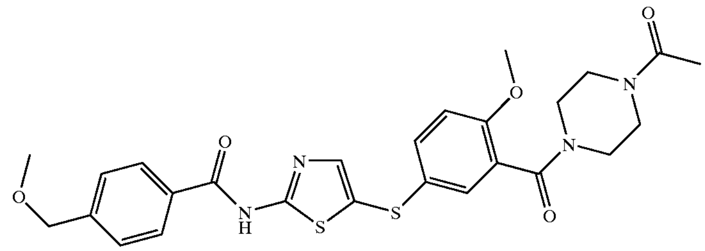 | 541.35 |
| 80 | 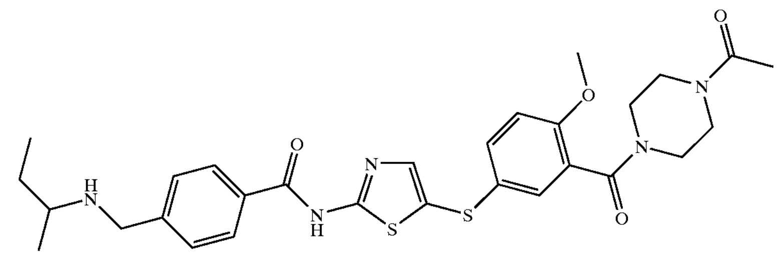 | 582.42 |
| 81 | 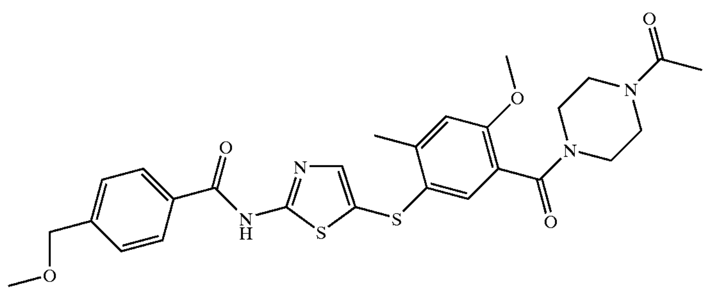 | 554.98 |
| 82 | 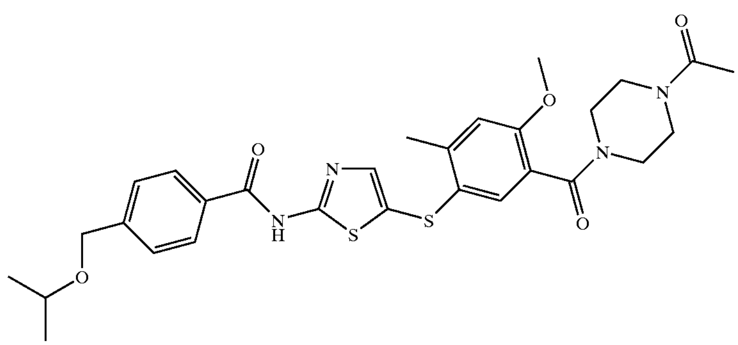 | 583.37 |
| 83 | 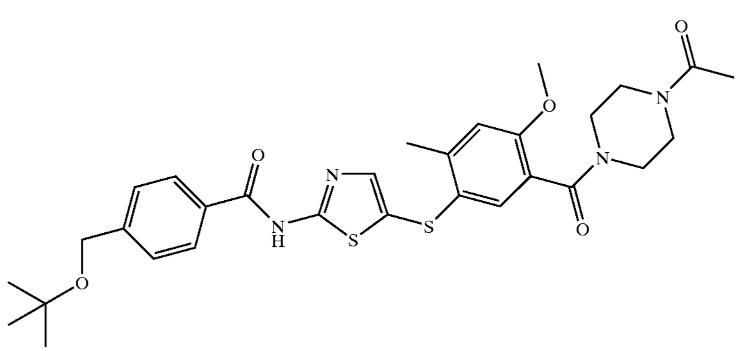 | 597.36 |

-continued

| Ex. No. | Structure | MS (M + H)+ |
|---|---|---|
| 84 | 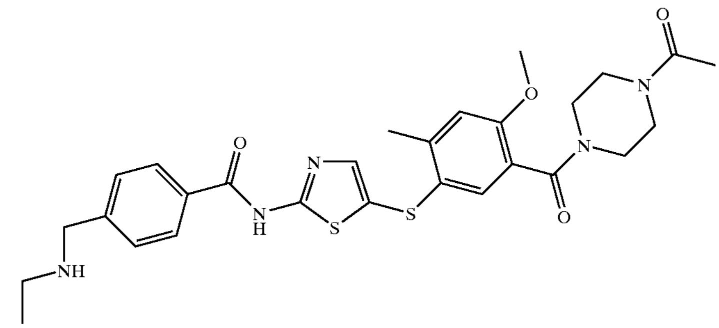 | 568.47 |
| 85 | 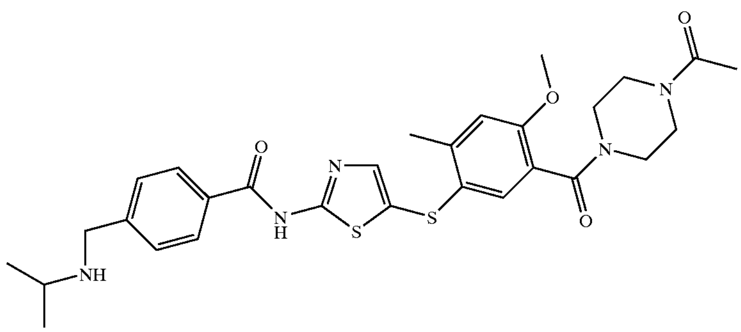 | 582.32 |
| 86 | 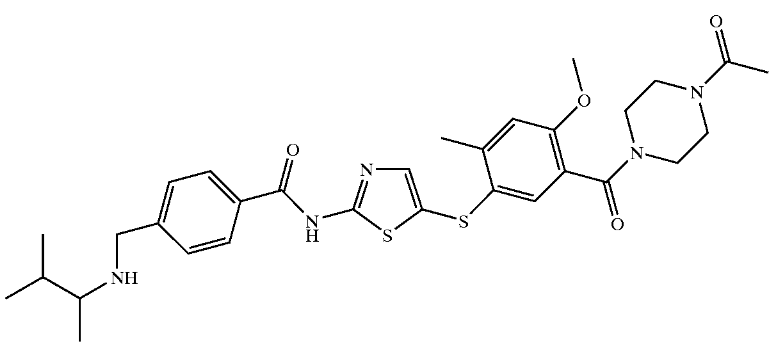 | 610.35 |
| 87 | 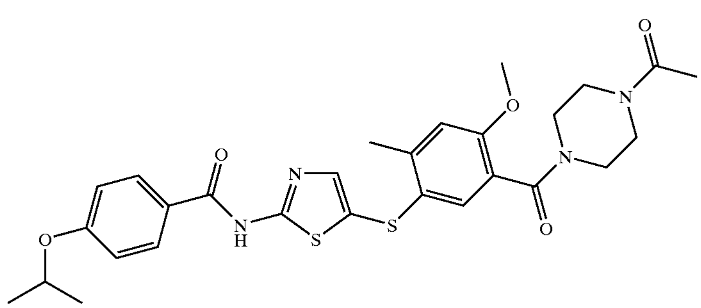 | 569.18 |

-continued

| Ex. No. | Structure | MS (M + H)+ |
|---|---|---|
| 88 | 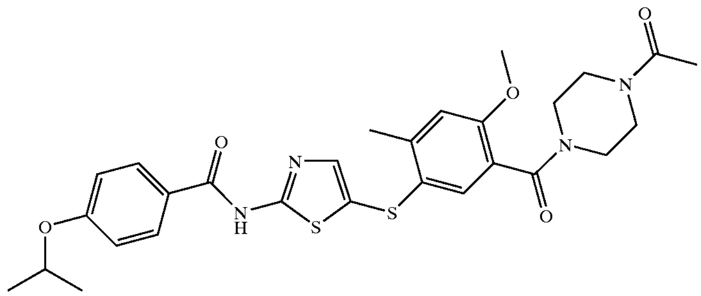 | 583.29 |
| 89 | 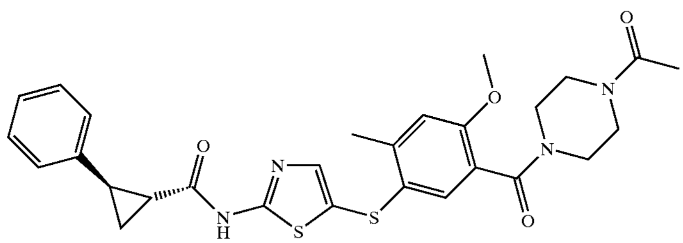 | 551.11 |
| 90 | 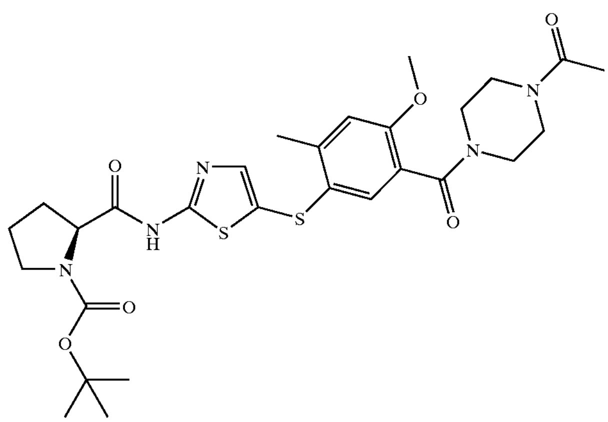 | 603.97 |
| 91 | 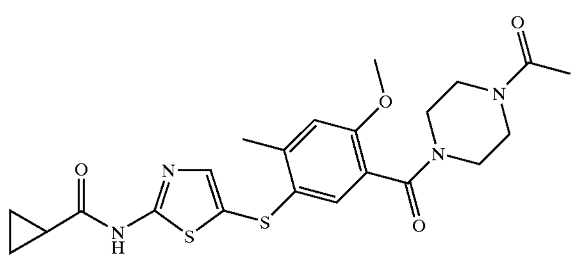 | 475.4 |
| 92 | 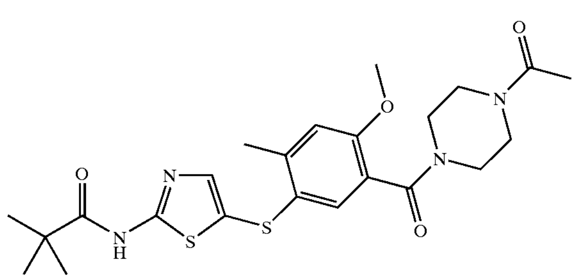 | 491.57 |

-continued

| Ex. No. | Structure | MS (M + H)+ |
|---|---|---|
| 93 | 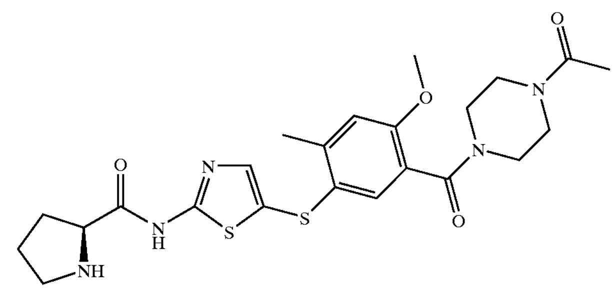 | 504.58 |
| 94 | 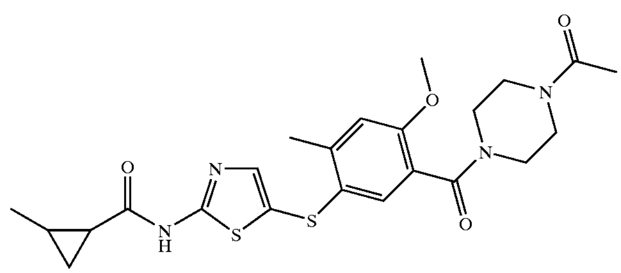 | 489.6 |
| 95 | 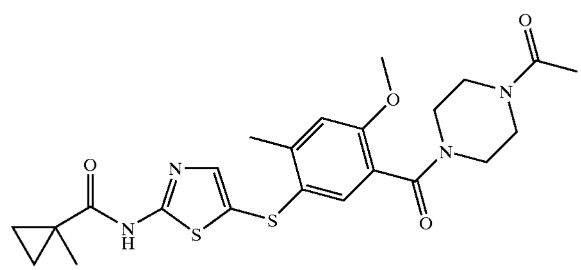 | 489.58 |
| 96 | 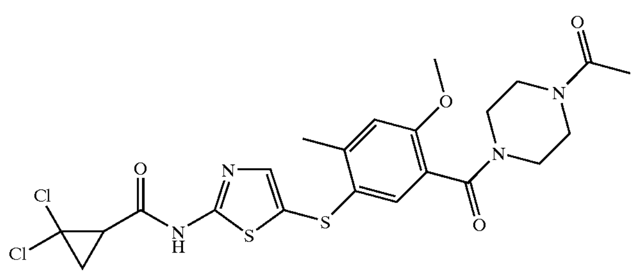 | 543.52 |
| 97 | 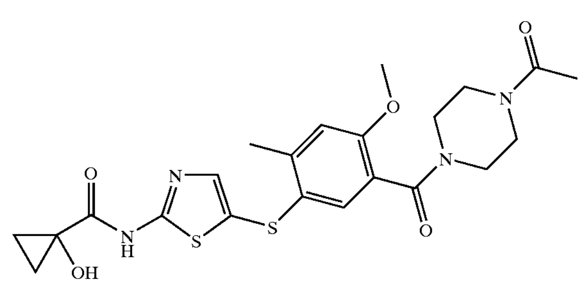 | 491.28 |

-continued
| Ex. No. | Structure | MS (M + H)+ |
|---|---|---|
| 98 | 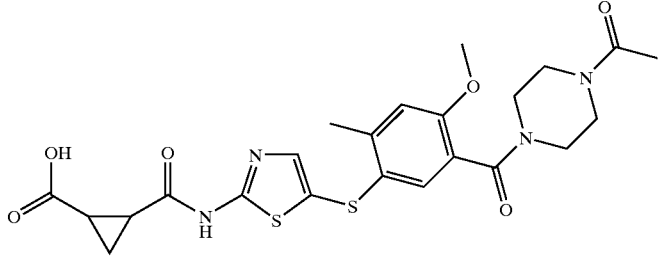 | 519.5 |
| 99 | 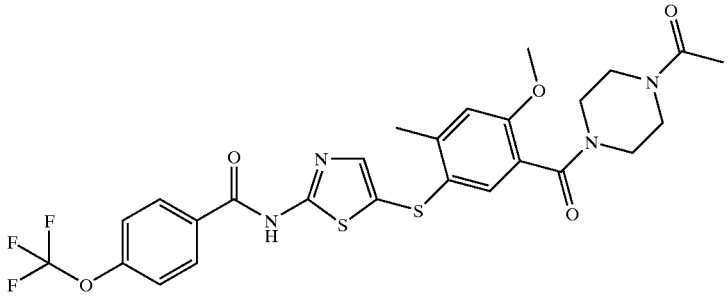 | 595.19 |
| 100 | 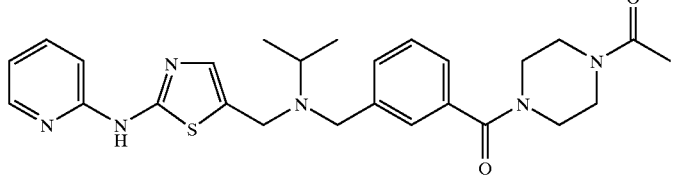 | 493.38 |
| 101 | 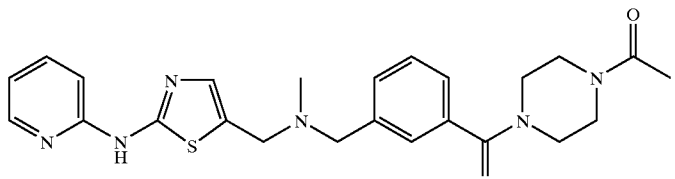 | 465.29 |
| 102 | 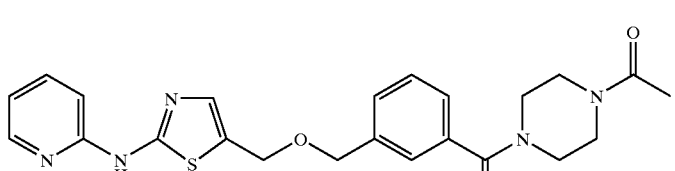 | 452.12 |
| 103 | 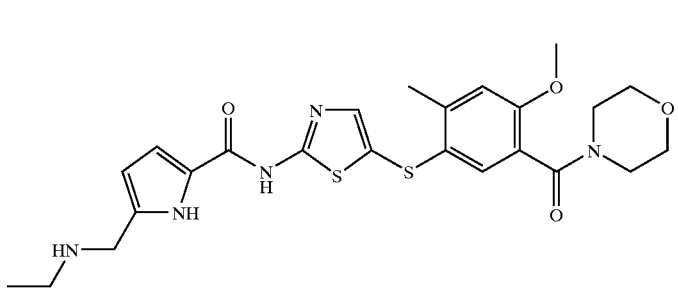 | 516.2 |

-continued
| Ex. No. | Structure | MS (M + H)+ |
|---|---|---|
| 104 | 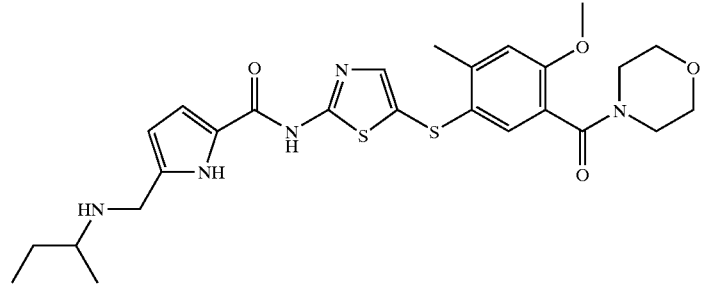 | 544.32 |
| 105 | 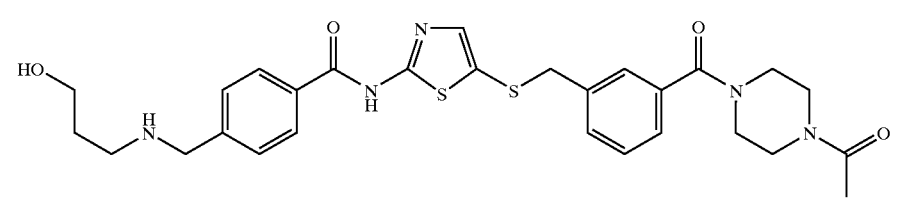 | 568.28 |
| 106 | 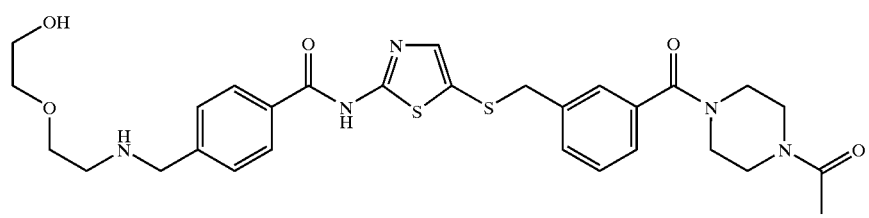 | 598.18 |
| 107 | 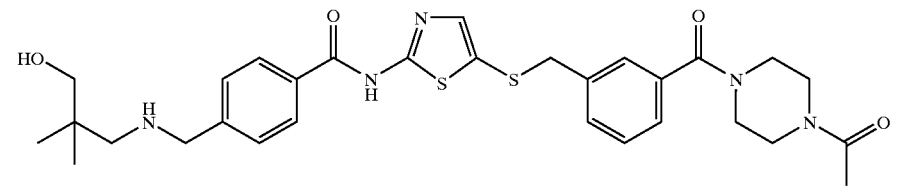 | 596.35 |
| 108 | 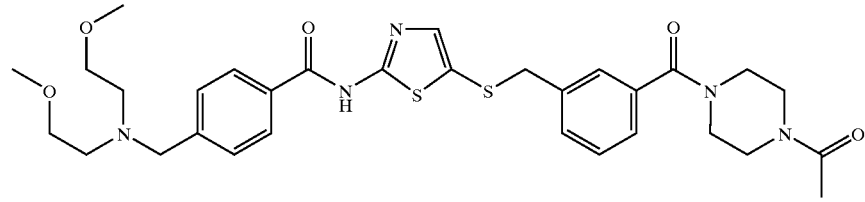 | 626.54 |
| 109 | 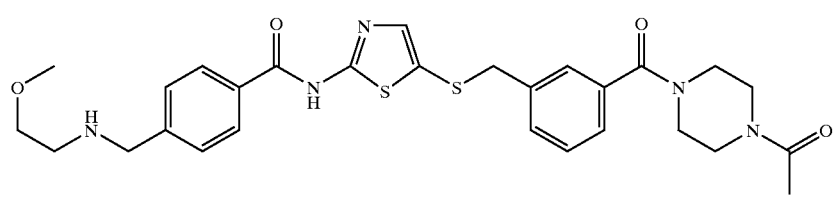 | 568.26 |
| 110 | 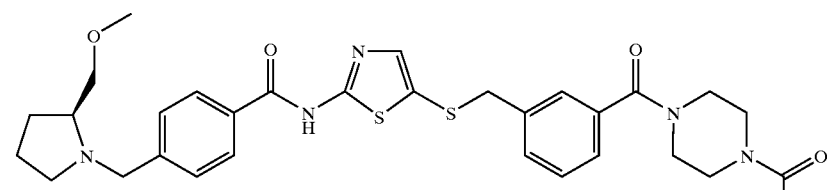 | 608.5 |

-continued
| Ex. No. | Structure | MS (M + H)+ |
|---|---|---|
| 111 | 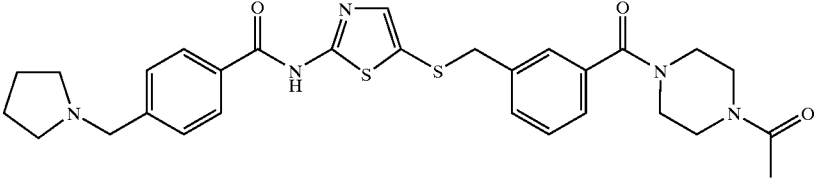 | 564.43 |
| 112 | 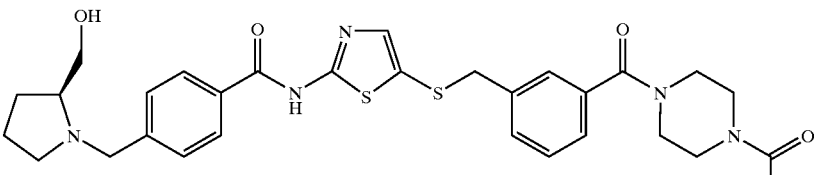 | 594.51 |
| 113 | 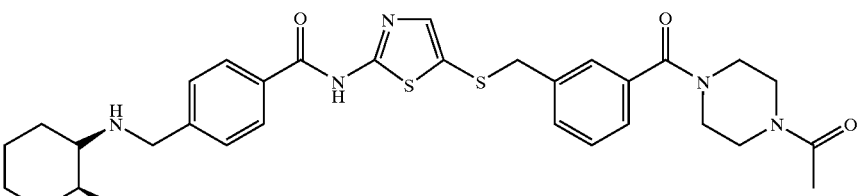 | 608.46 |
| 114 | 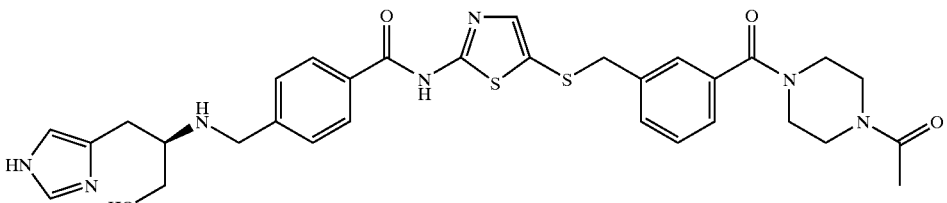 | 634.26 |
| 115 | 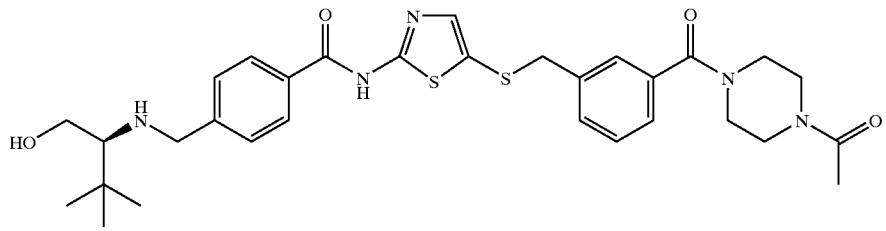 | 610.58 |
| 116 | 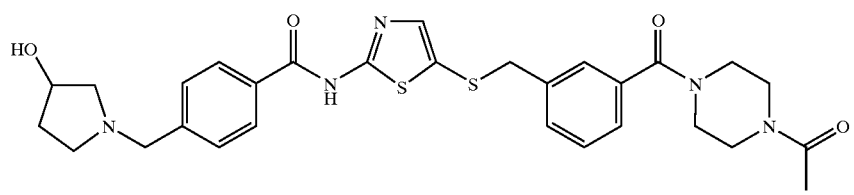 | 580.26 |
| 117 | 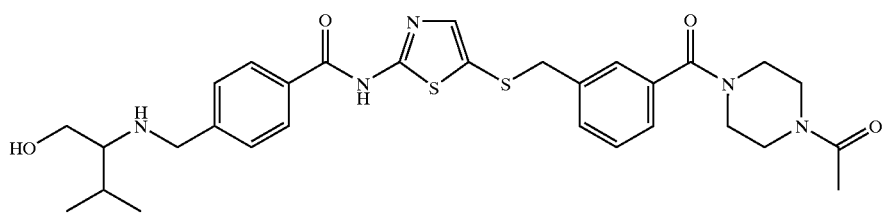 | 596.58 |

-continued

| Ex. No. | Structure | MS (M + H)+ |
|---|---|---|
| 118 | 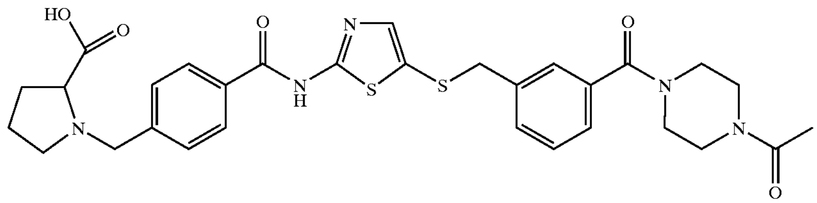 | 608.19 |
| 119 | 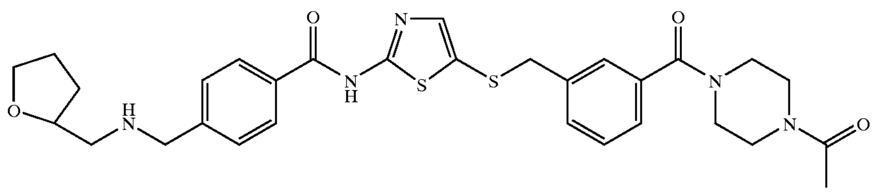 | 594.34 |
| 120 | 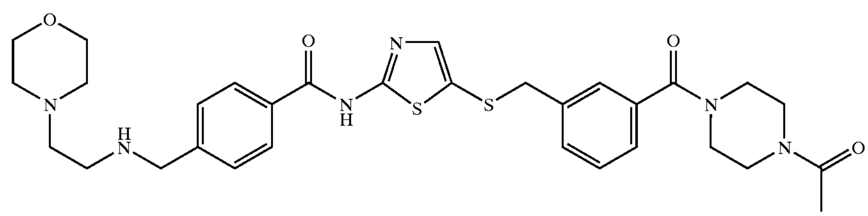 | 623.47 |
| 121 | 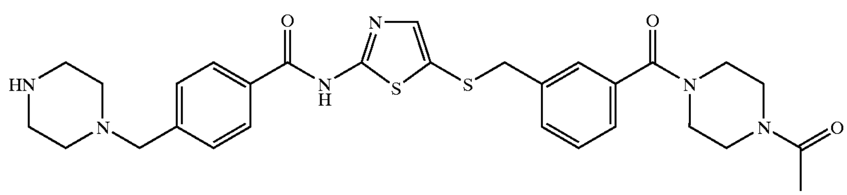 | 579.35 |
| 122 | 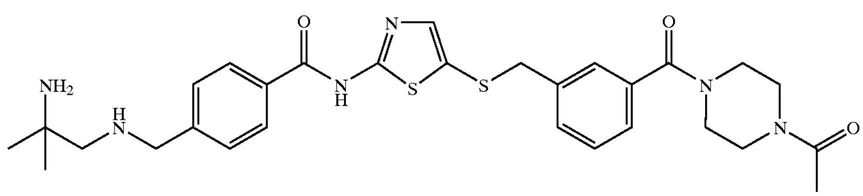 | 581.36 |
| 123 | 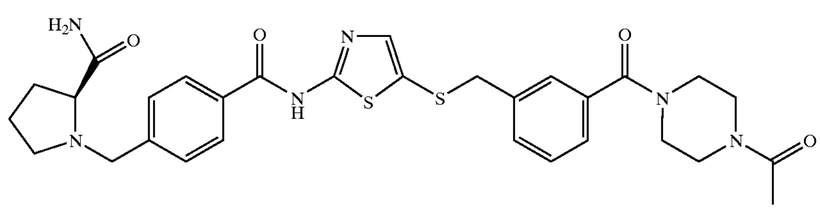 | 607.51 |
| 124 | 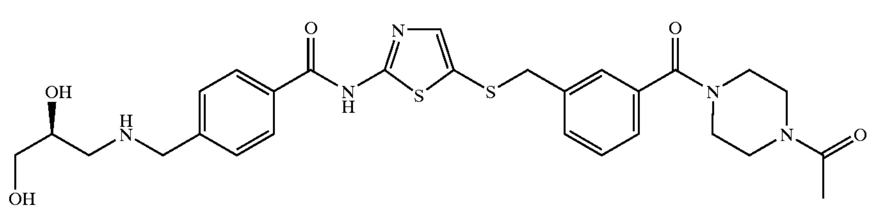 | 584.18 |

| Ex. No. | Structure | MS (M + H)+ |
|---|---|---|
| 125 | 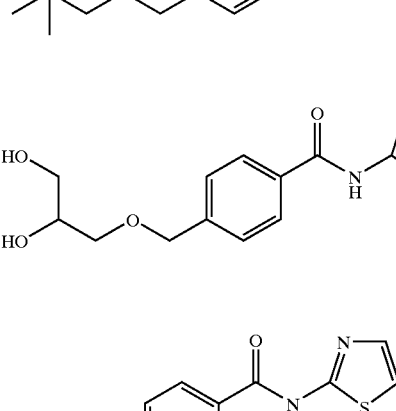 | 582.4 |
| 126 | 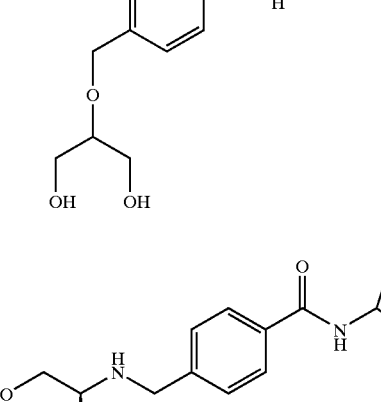 | 566.39 |
| 127 | 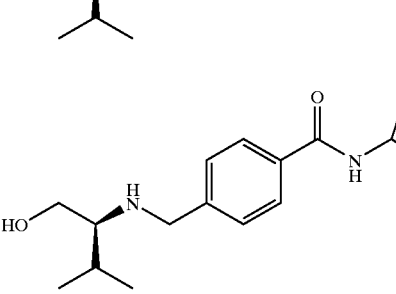 | 585.22 |
| 128 | 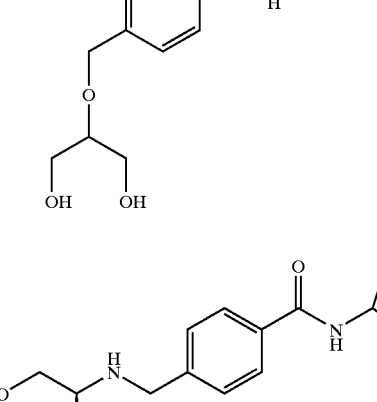 | 585.17 |
| 129 | 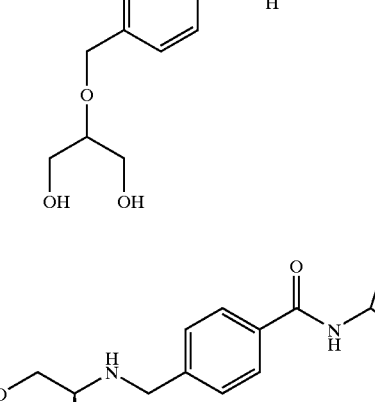 | 596.65 |
| 130 | 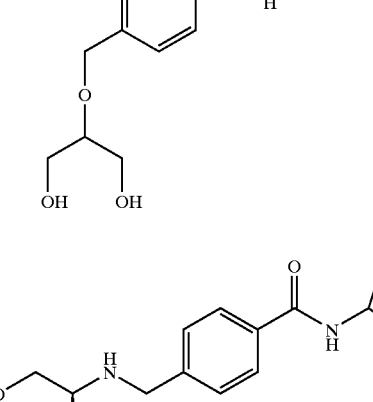 | 596.59 |

-continued
| Ex. No. | Structure | MS (M + H)+ |
|---|---|---|
| 131 | 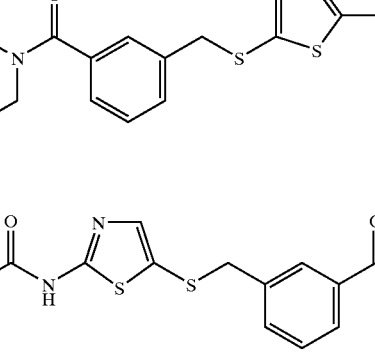 | 470.4 |
| 132 | 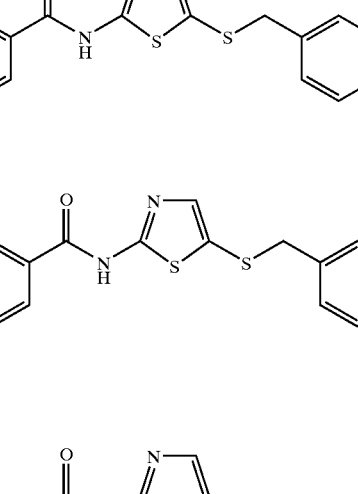 | 580.26 |
| 133 | 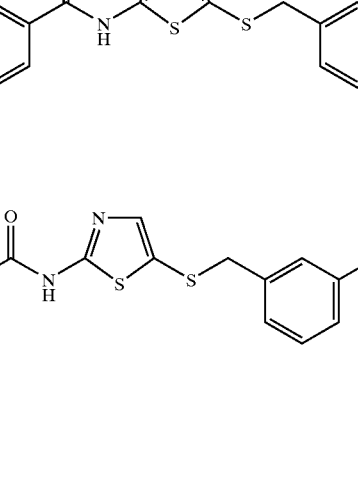 | 594.4 |
| 134 | 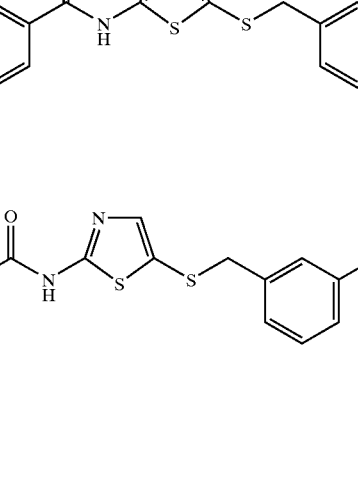 | 644.4 |
| 135 | 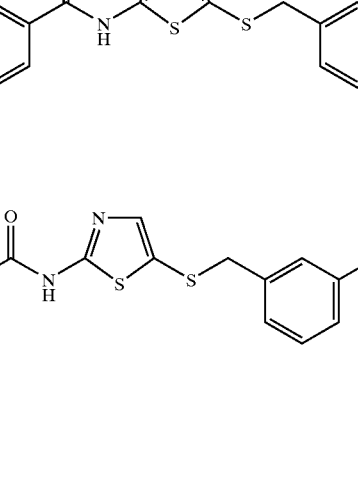 | 644.35 |
| 136 | 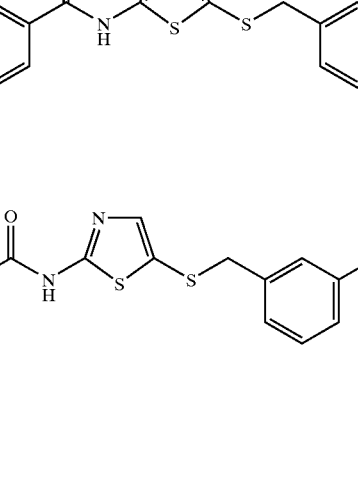 | 568.24 |

| Ex. No. | Structure | MS (M + H)+ |
|---|---|---|
| 137 | 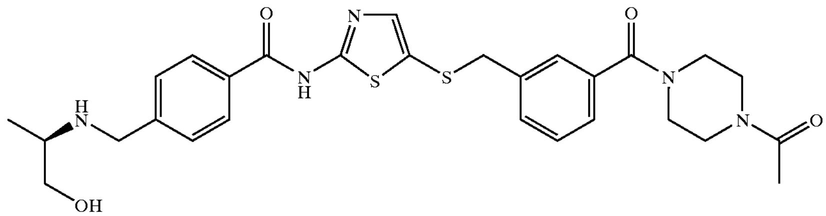 | 568.43 |
| 138 | 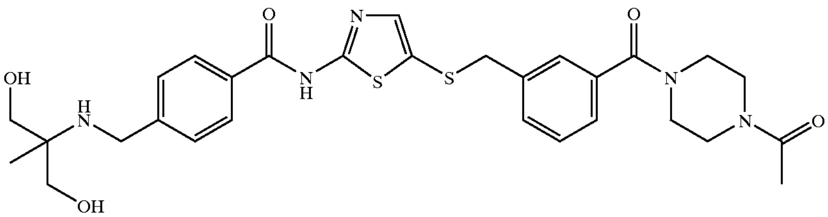 | 598.18 |
| 139 | 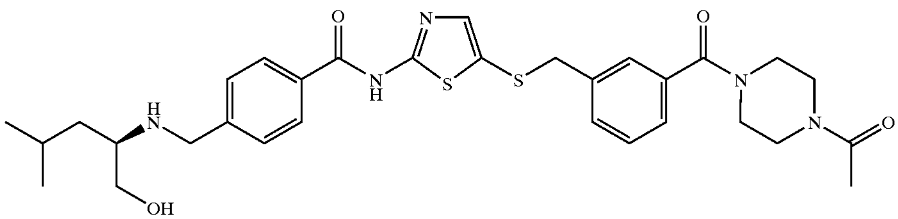 | 610.26 |
| 140 | 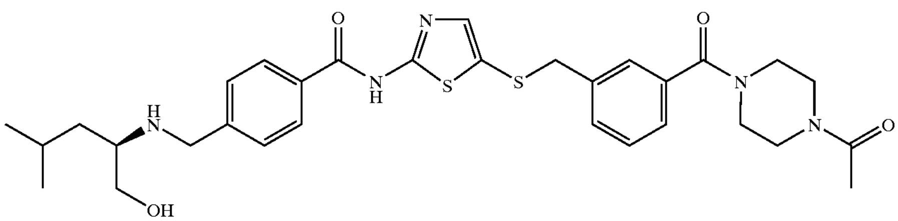 | 610.24 |
| 141 | 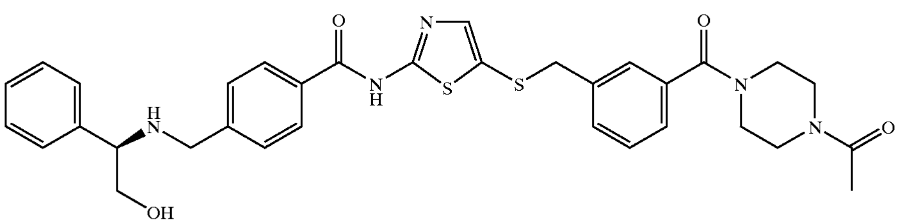 | 630.35 |
| 142 | 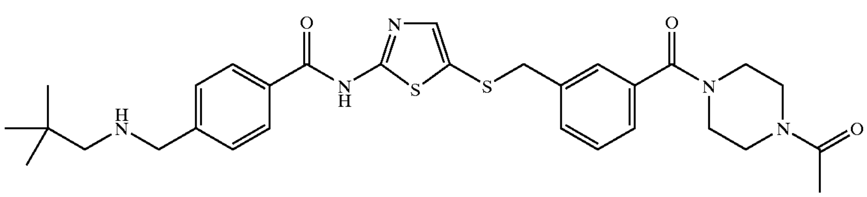 | 580.4 |
| 143 | 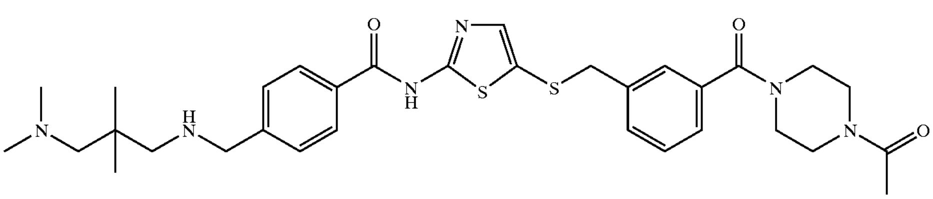 | 623.26 |

| Ex. No. | Structure | MS (M + H)+ |
|---|---|---|
| 144 | 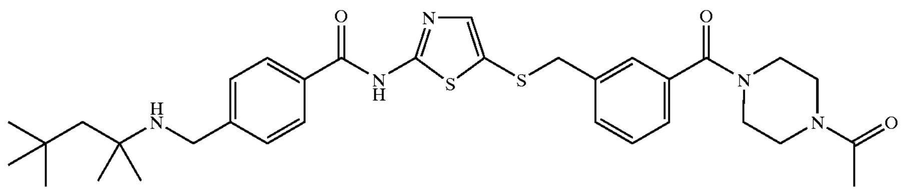 | 622.43 |
| 145 | 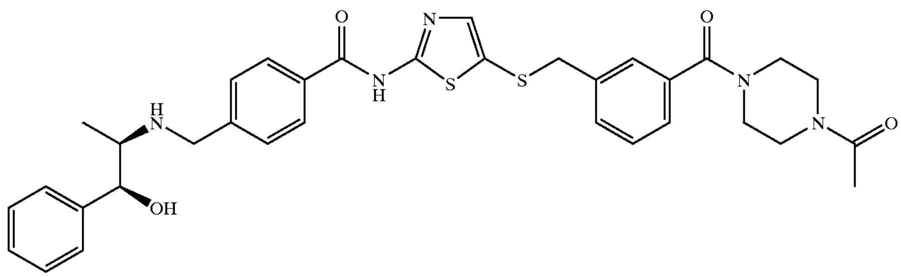 | 644.28 |
| 146 | 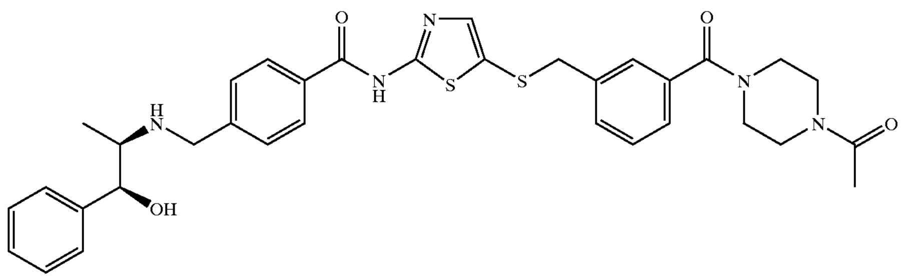 | 644.2 |
| 147 | 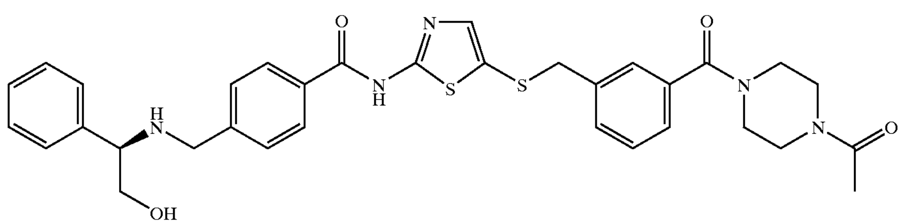 | 630.19 |
| 148 | 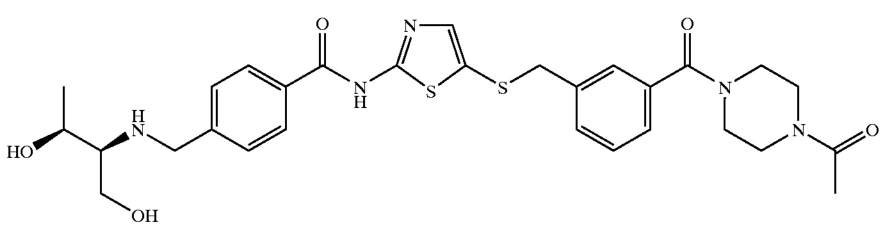 | 598.19 |
| 149 | 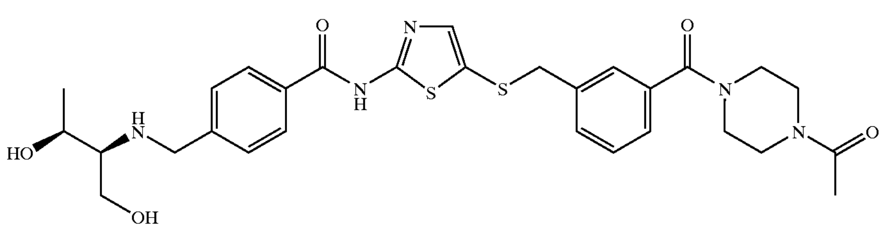 | 598.2 |

| Ex. No. | Structure | MS (M + H)+ |
|---|---|---|
| 150 | 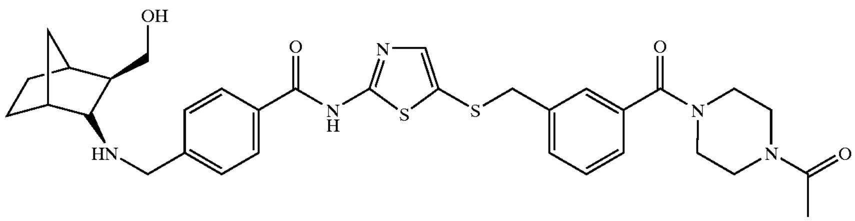 | 634.3 |
| 151 | 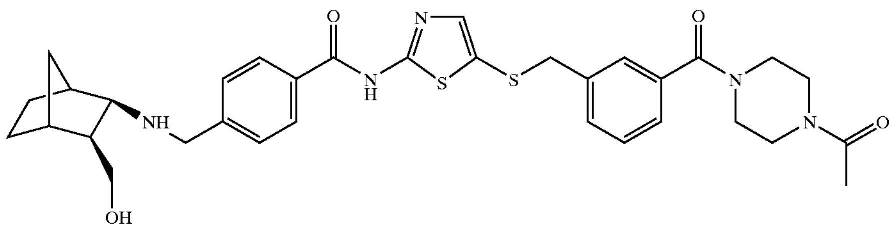 | 634.32 |
| 152 | 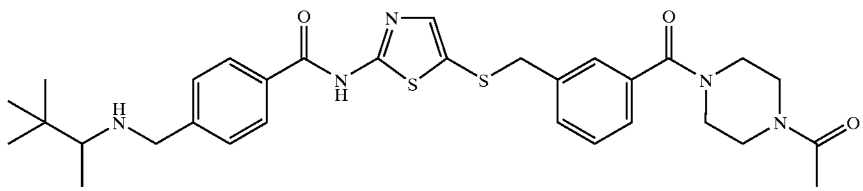 | 594.34 |
| 153 | 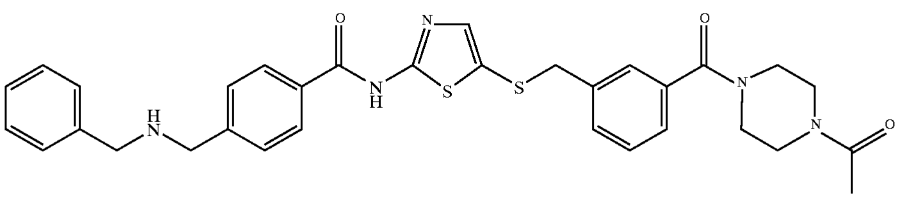 | 600.22 |
| 154 | 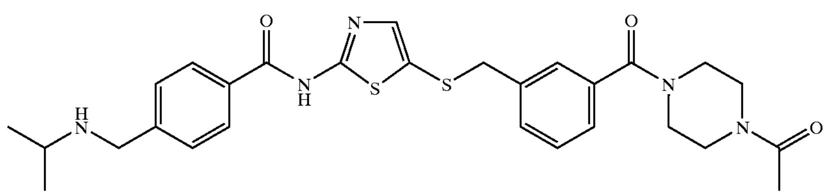 | 552.3 |
| 155 | 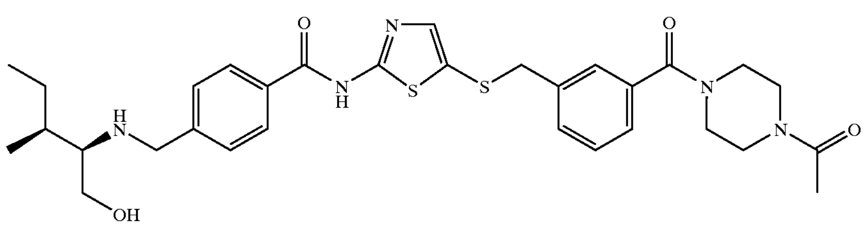 | 610.31 |
| 156 | 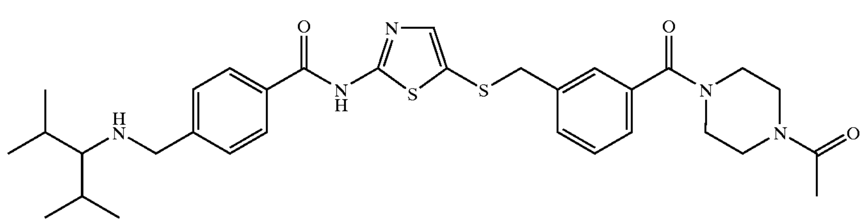 | 608.3 |

-continued

| Ex. No. | Structure | MS (M + H)+ |
|---|---|---|
| 157 | 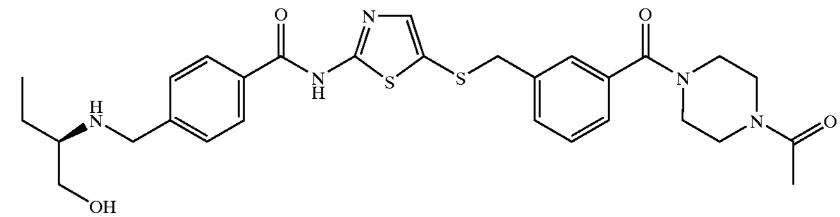 | 582.26 |
| 158 | 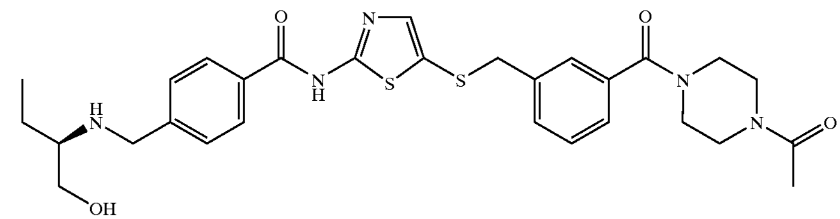 | 582.24 |
| 159 | 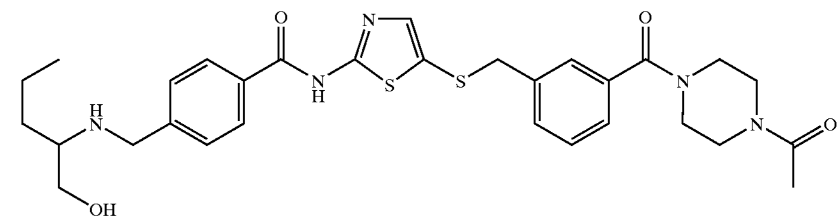 | 596.35 |
| 160 | 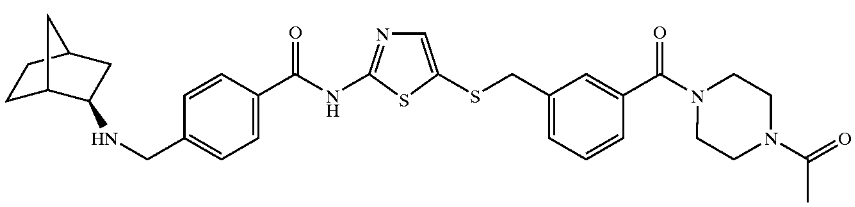 | 604.38 |
| 161 | 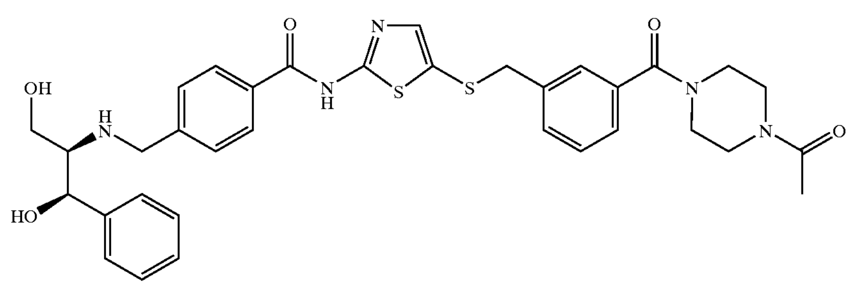 | 660.12 |
| 162 | 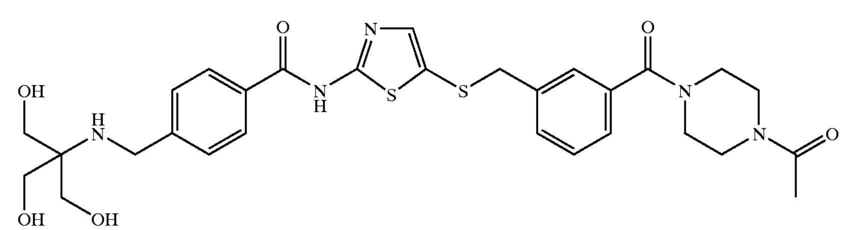 | 614.11 |

| Ex. No. | Structure | MS (M + H)+ |
|---|---|---|
| 163 | 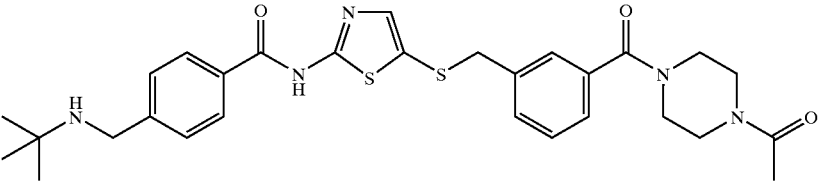 | 566.27 |
| 164 | 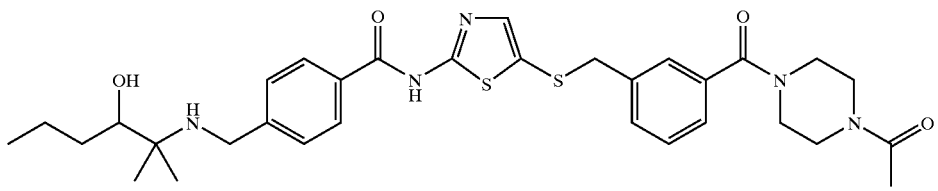 | 624.27 |
| 165 | 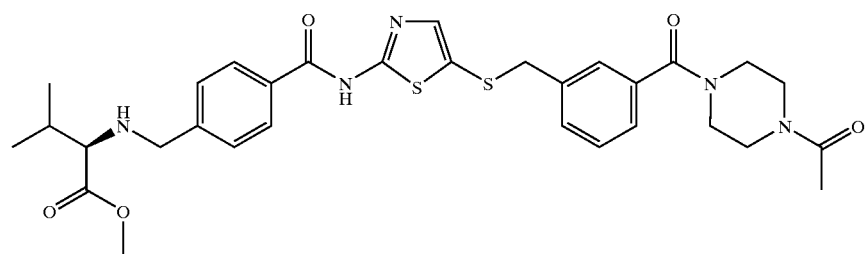 | 624.18 |
| 166 | 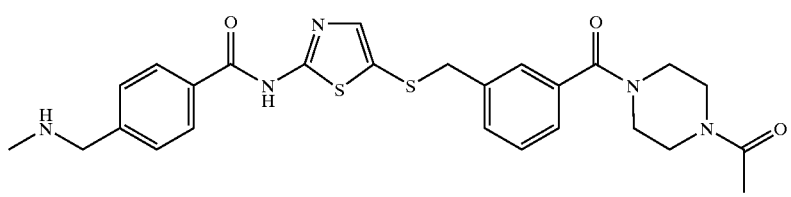 | 524.14 |
| 167 | 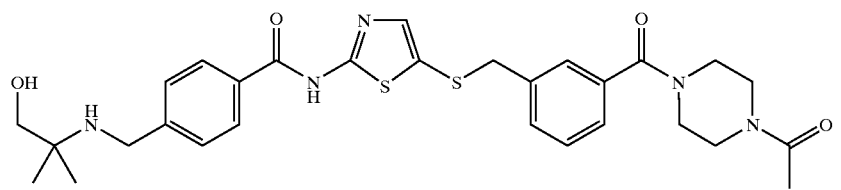 | 582.17 |
| 168 | 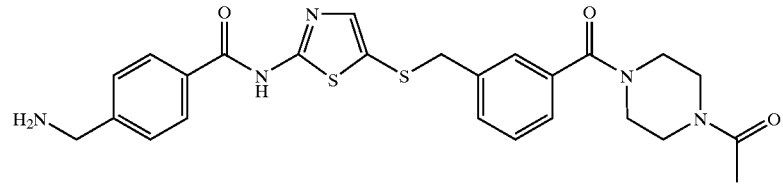 | 510.09 |
| 169 | 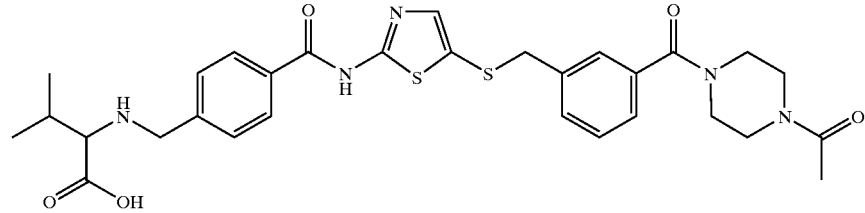 | 610.49 |

-continued

| Ex. No. | Structure | MS (M + H)+ |
|---|---|---|
| 170 | 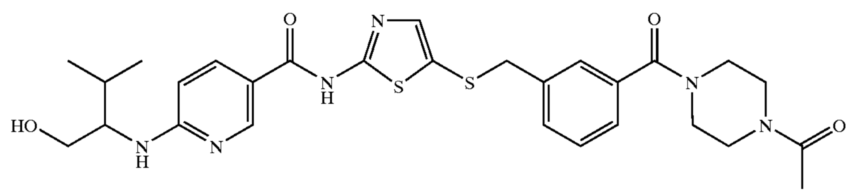 | 583.21 |
| 171 | 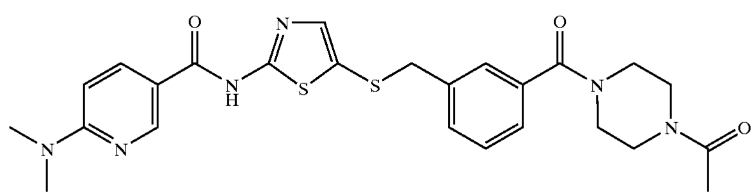 | 525.14 |
| 172 | 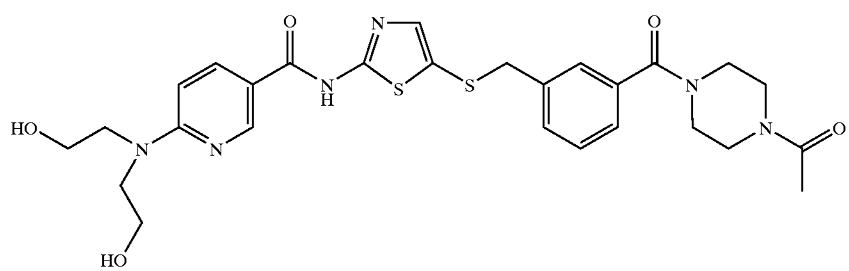 | 585.18 |
| 173 | 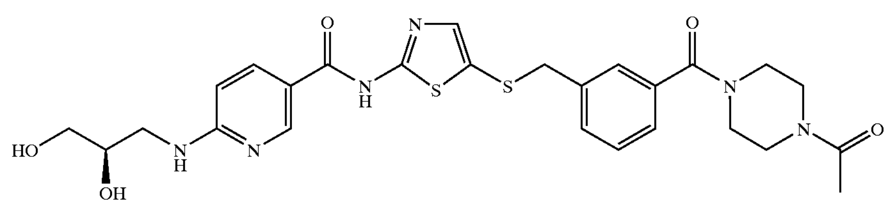 | 571.19 |
| 174 | 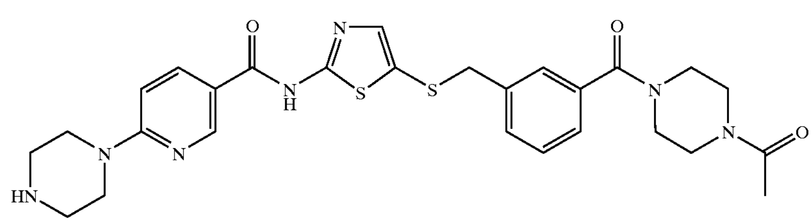 | 566.22 |
| 175 | 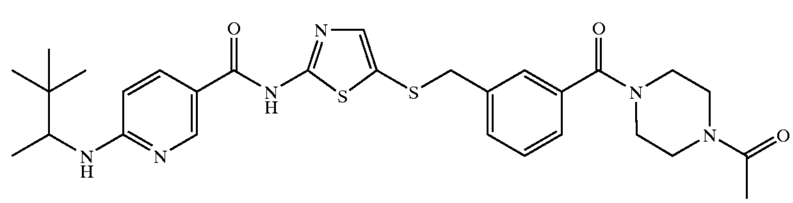 | 581.24 |
| 176 | 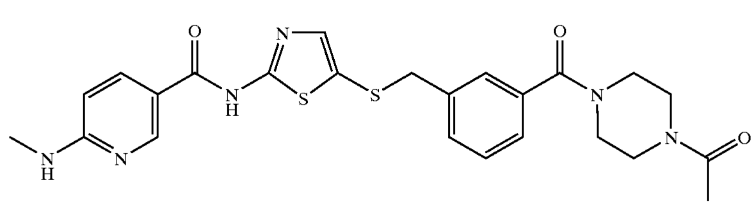 | 511.12 |

-continued

| Ex. No. | Structure | MS (M + H)+ |
|---|---|---|
| 177 | 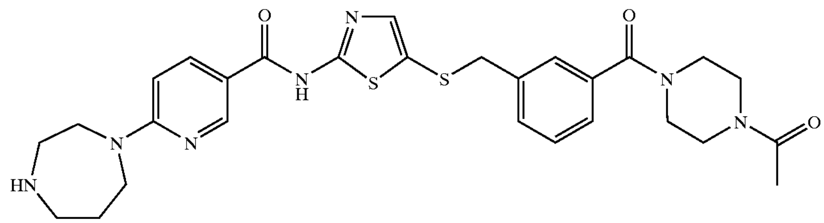 | 580.29 |
| 178 | 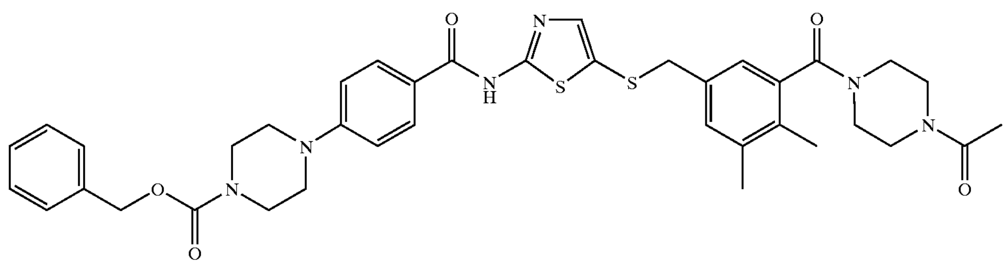 | 727.23 |
| 179 | 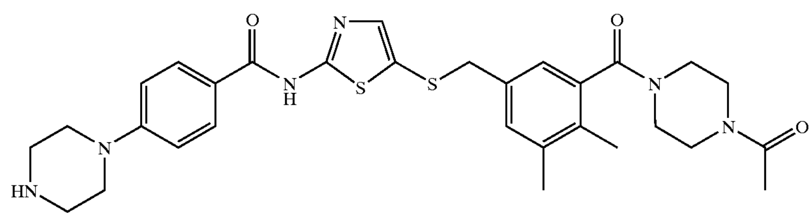 | 593.28 |
| 180 | 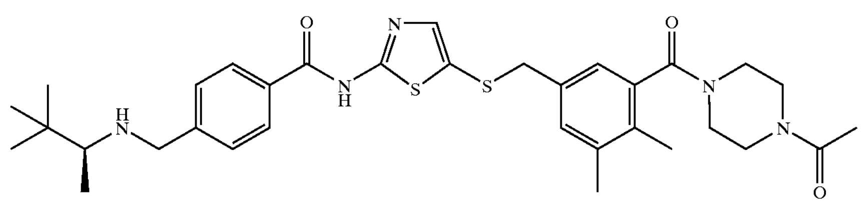 | 622.36 |
| 181 | 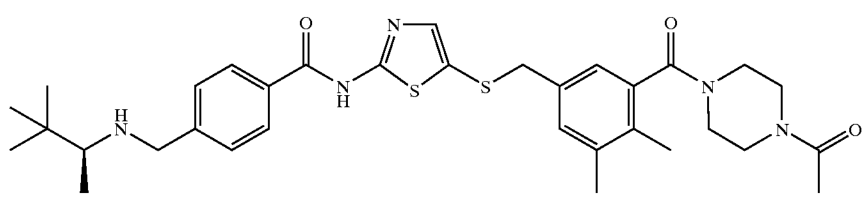 | 622.32 |
| 182 | 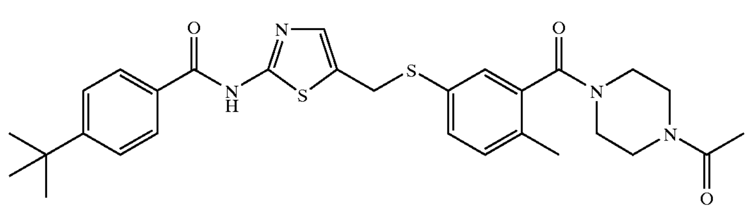 | 551.25 |
| 183 | 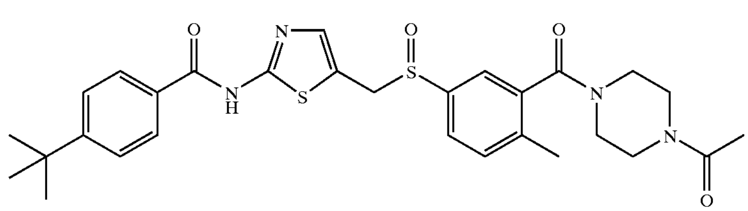 | 567.23 |

-continued

| Ex. No. | Structure | MS (M + H)+ |
|---|---|---|
| 184 | 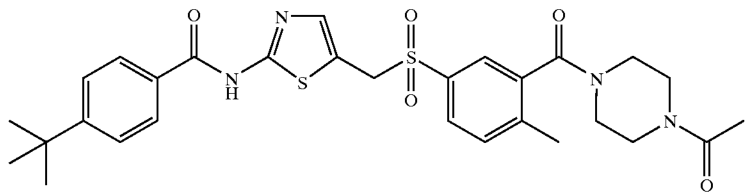 | 583.26 |
| 185 | 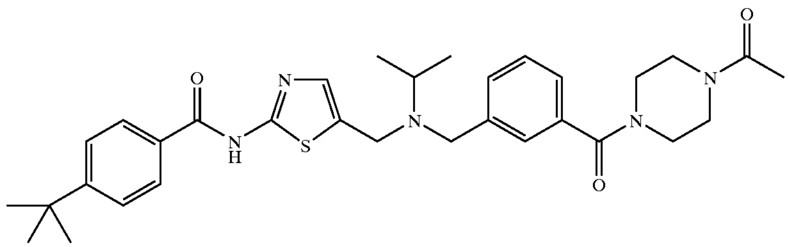 | 576.42 |
| 186 | 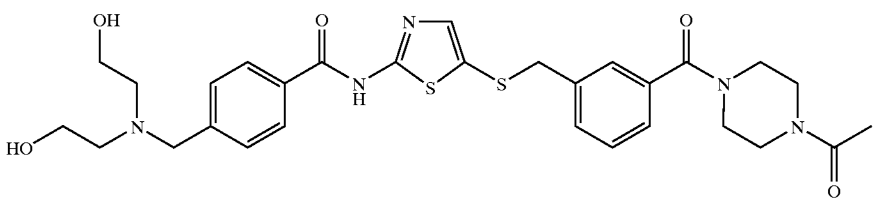 | 598.24 |
| 187 | 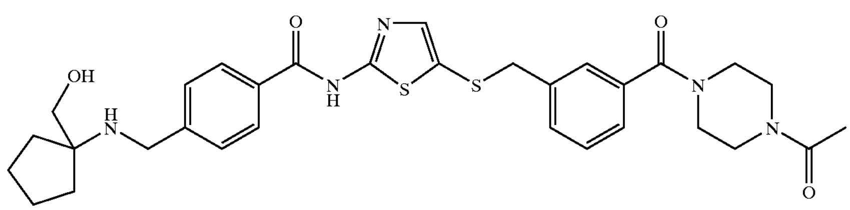 | 608.31 |
| 188 | 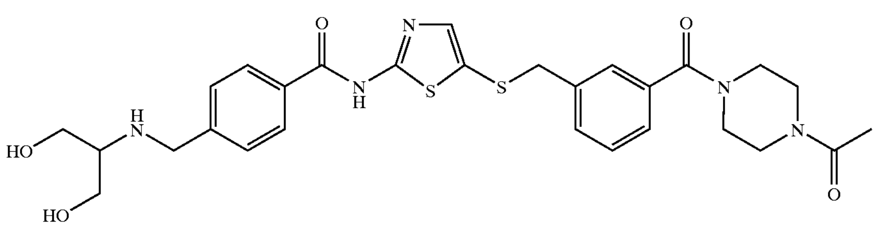 | 584.16 |
| 189 | 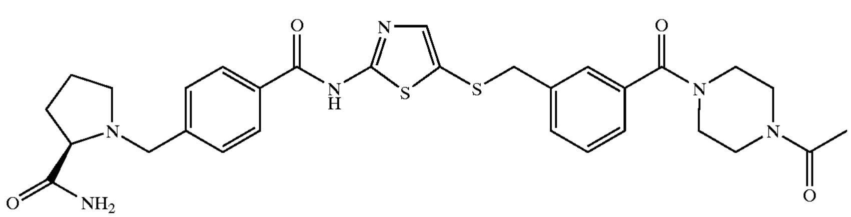 | 607.33 |
| 190 | 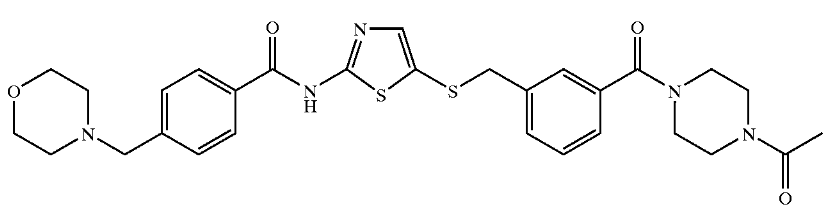 | 580.35 |

| Ex. No. | Structure | MS (M + H)+ |
|---|---|---|
| 191 | 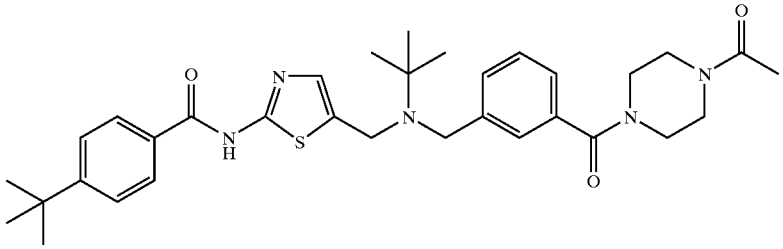 | 590.23 |
| 192 | 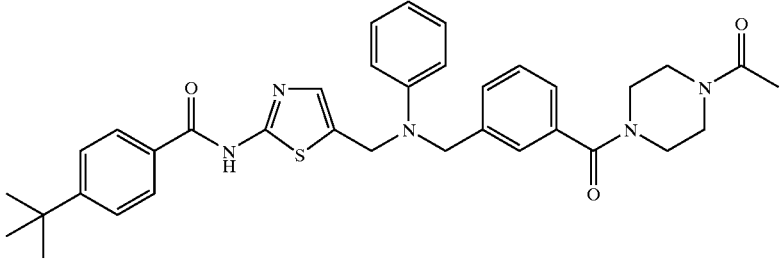 | 610.27 |
| 193 | 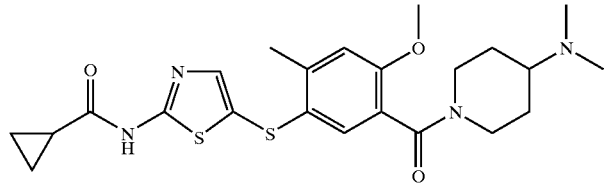 | 475.3 |
| 194 | 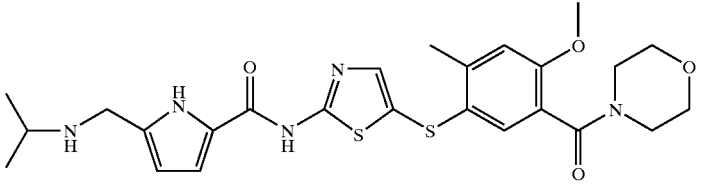 | 530.37 |
| 195 | 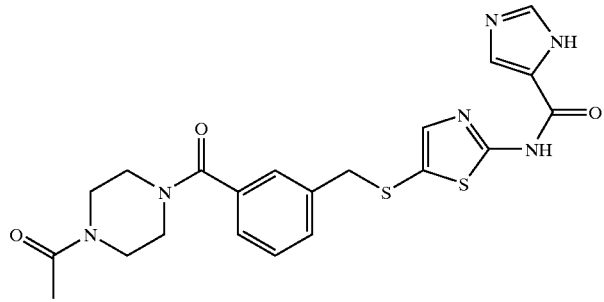 | 471.12 |
| 196 | 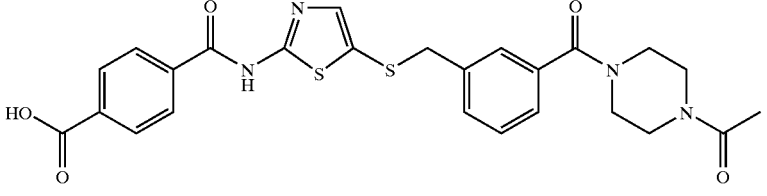 | 525.19 |

-continued

| Ex. No. | Structure | MS (M + H)+ |
|---|---|---|
| 197 | 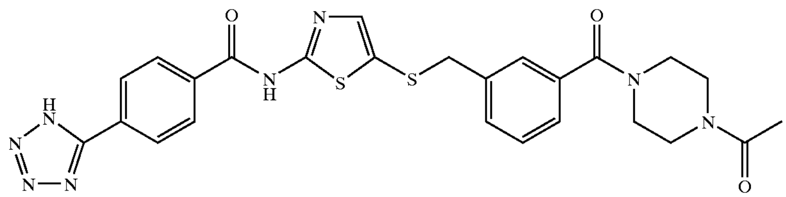 | 549.19 |
| 198 | 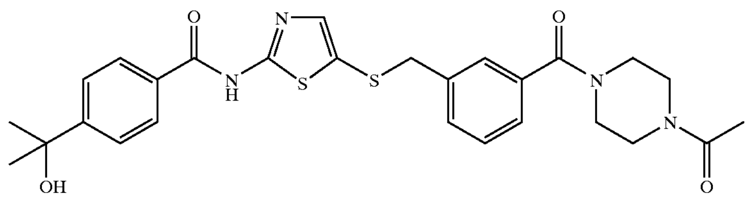 | 539.53 |
| 199 | 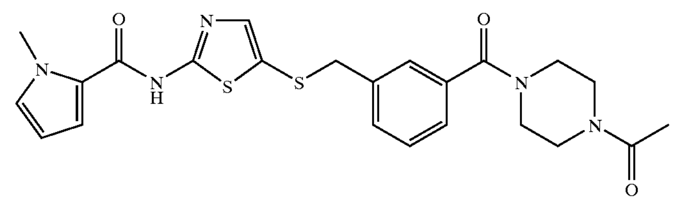 | 484.25 |
| 200 | 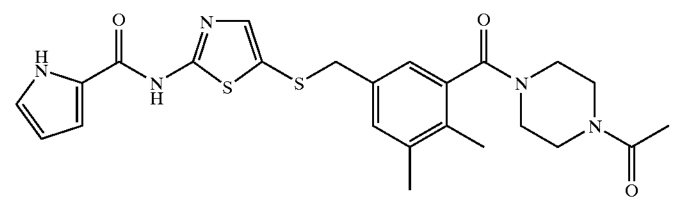 | 498.19 |
| 201 | 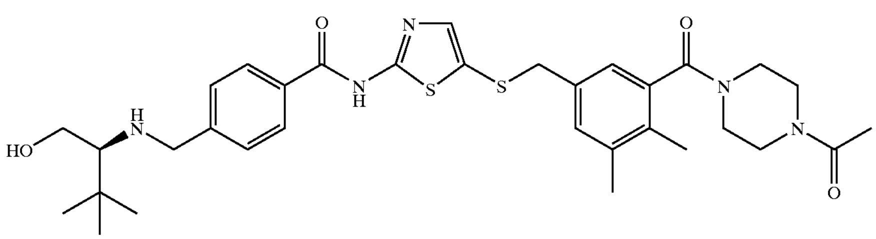 | 638.39 |
| 202 | 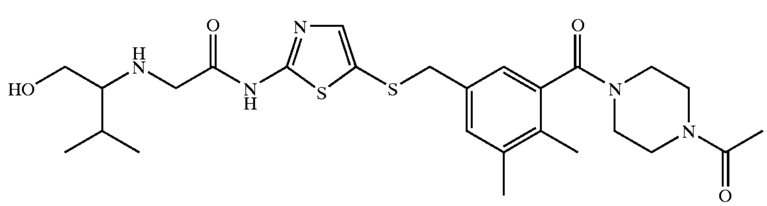 | 624.54 |
| 203 | 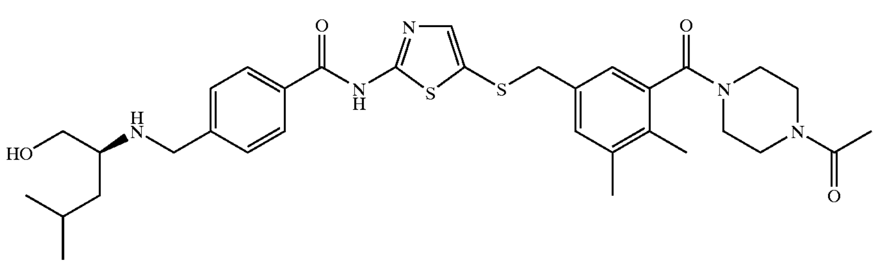 | 638.48 |

-continued

| Ex. No. | Structure | MS (M + H)+ |
|---|---|---|
| 204 | 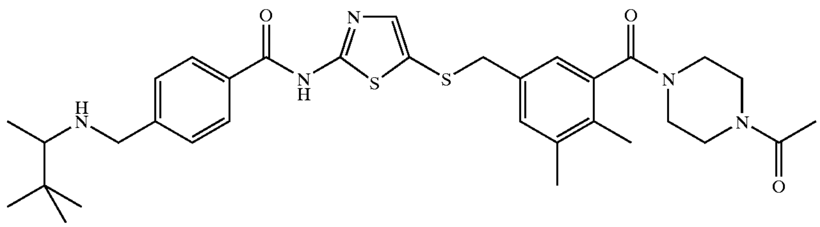 | 622.33 |
| 205 | 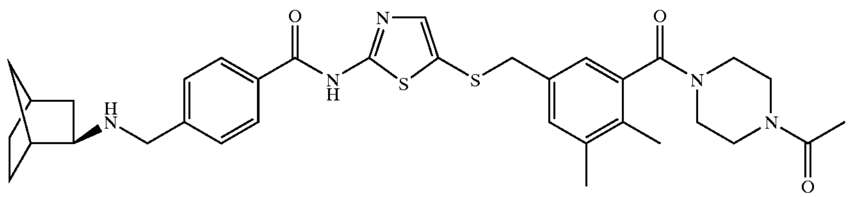 | 632.34 |
| 206 | 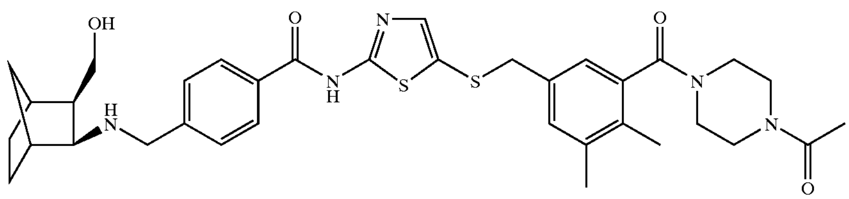 | 662.22 |
| 207 | 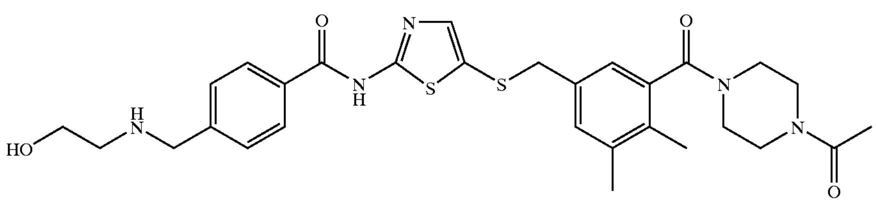 | 582.19 |
| 208 | 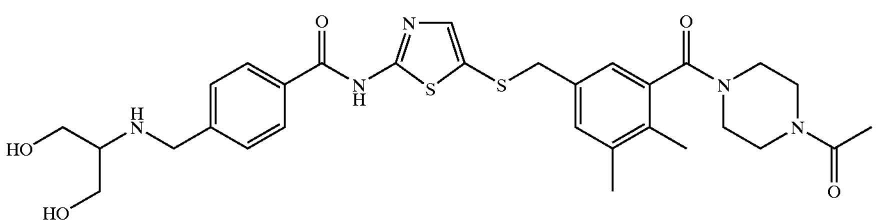 | 612.35 |
| 209 | 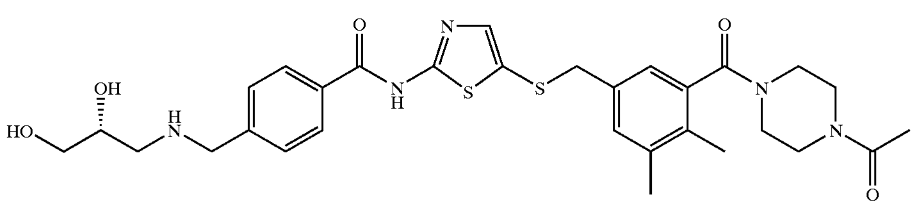 | 612.34 |
| 210 | 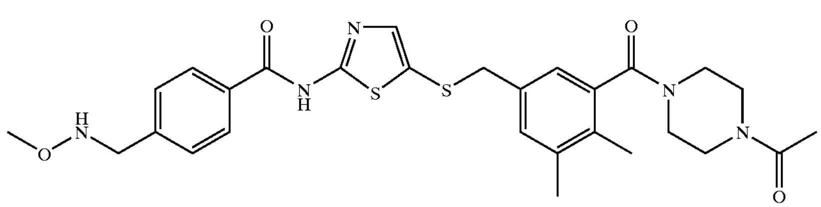 | 568.19 |

-continued

| Ex. No. | Structure | MS (M + H)+ |
|---|---|---|
| 211 | 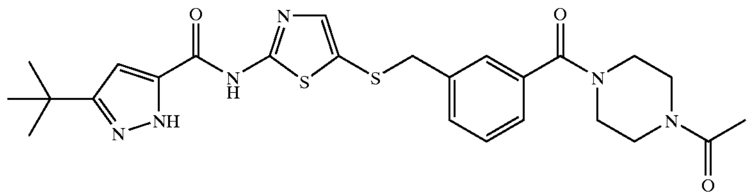 | 527.19 |
| 212 | 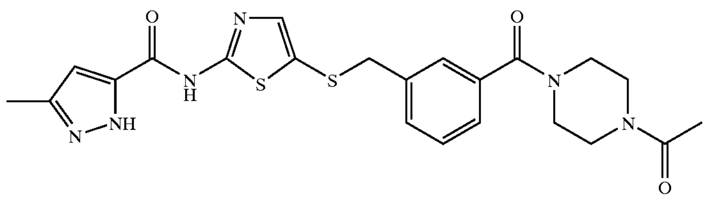 | 485.1 |
| 213 | 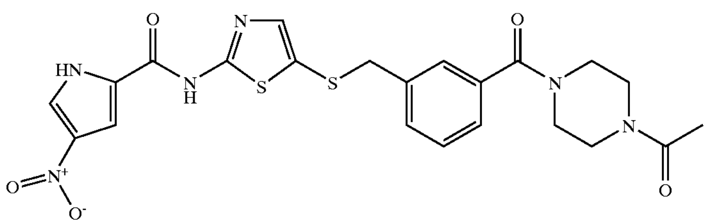 | 514.97 |
| 214 | 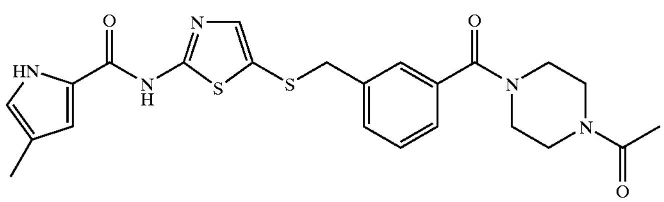 | 484.06 |
| 215 | 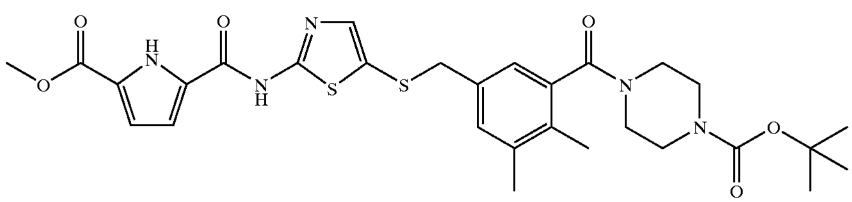 | 614.32 |
| 216 | 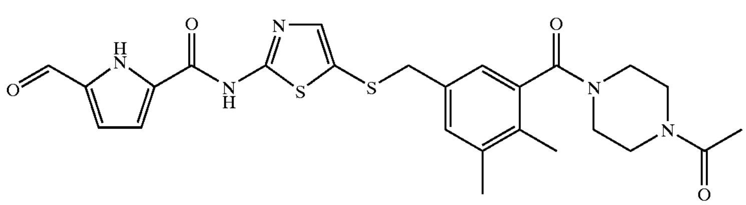 | 526.23 |
| 217 | 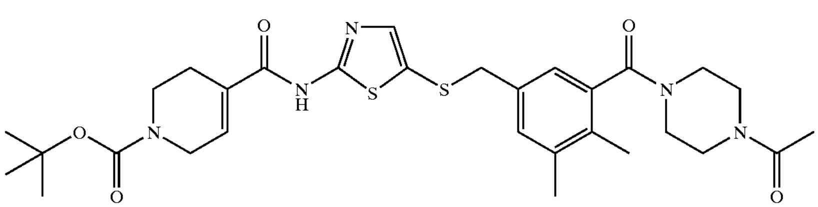 | 614.2 |

-continued

| Ex. No. | Structure | MS (M + H)+ |
|---|---|---|
| 218 | 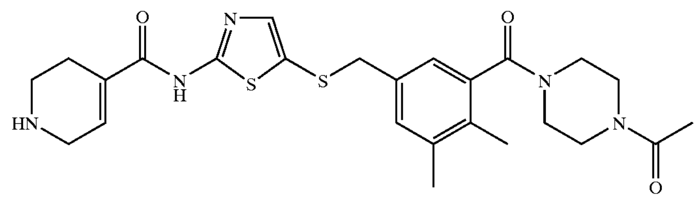 | 514.25 |
| 219 | 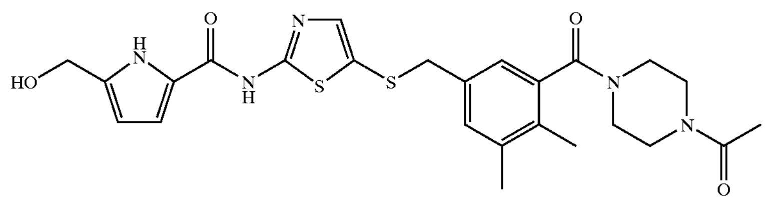 | 528.25 |
| 220 | 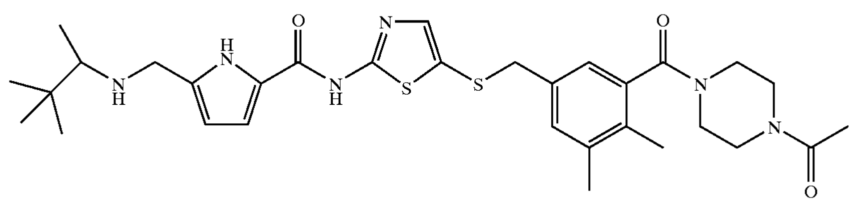 | 611.31 |
| 221 | 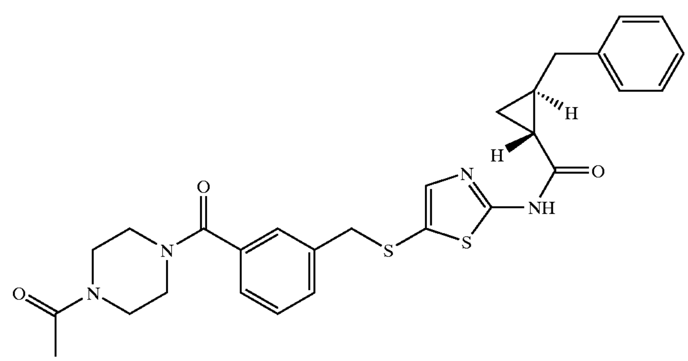 | 535.31 |
| 222 | 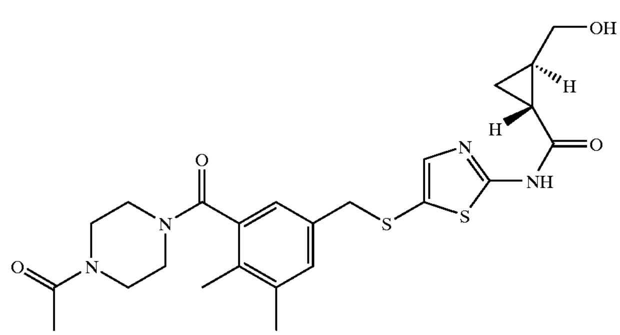 | 503.25 |

-continued

| Ex. No. | Structure | MS (M + H)+ |
|---|---|---|
| 223 | 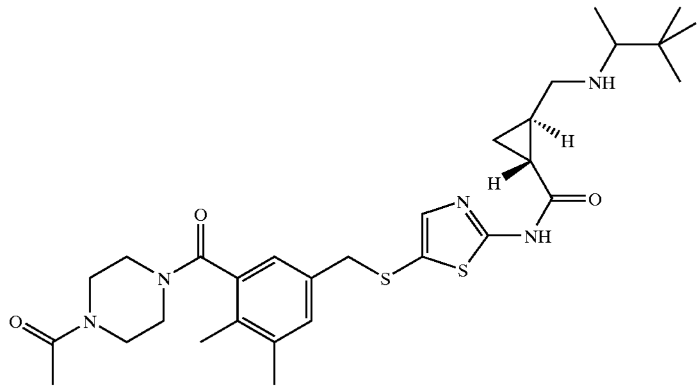 | 586.37 |
| 224 | 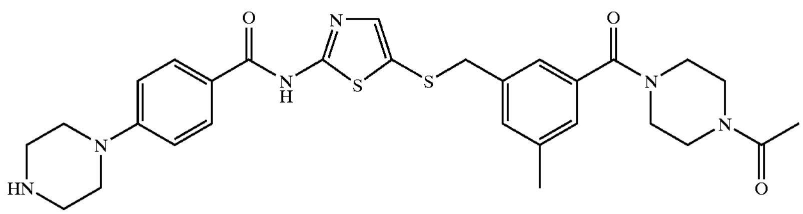 | 579.26 |
| 225 | 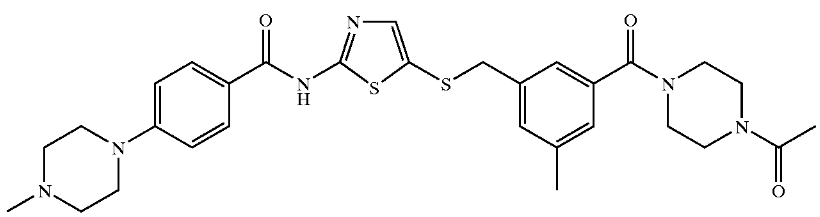 | 593.35 |
| 226 | 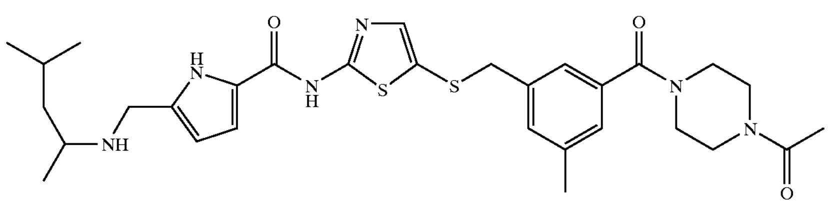 | 597.43 |
| 227 | 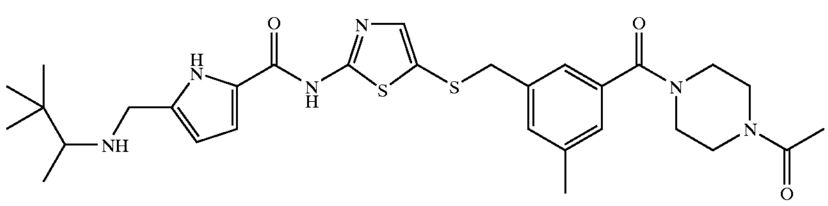 | 597.33 |
| 228 | 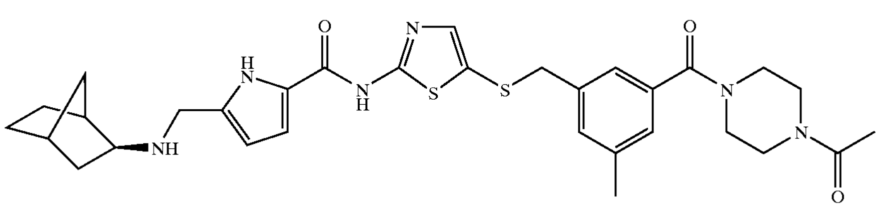 | 607.21 |

| Ex. No. | Structure | MS (M + H)+ |
|---|---|---|
| 229 | 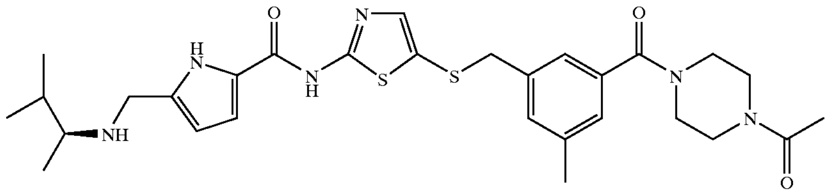 | 583.57 |
| 230 | 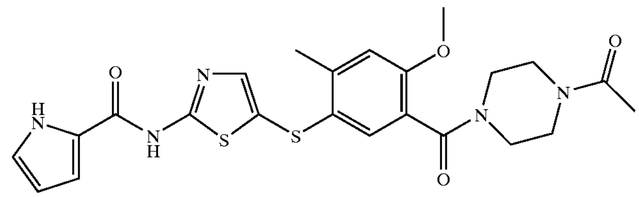 | 500.33 |
| 231 | 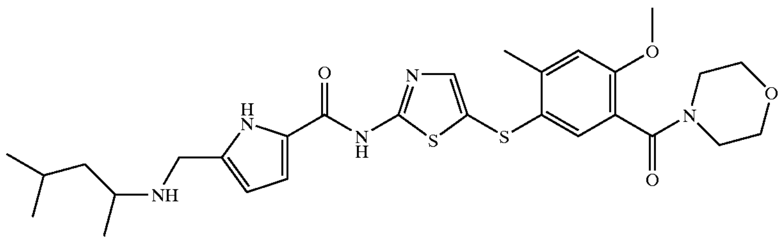 | 572.33 |
| 232 | 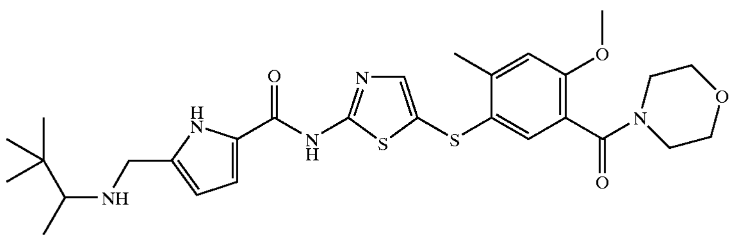 | 572.34 |
| 233 | 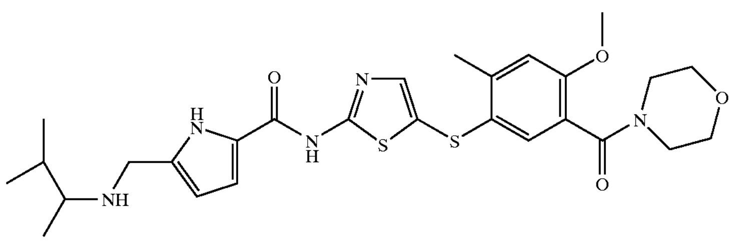 | 558.34 |
| 234 | 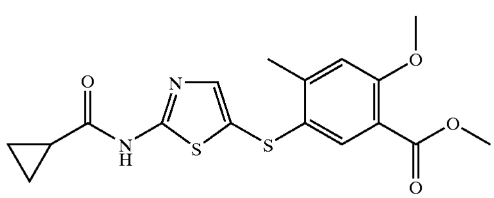 | 379.39 |
| 235 | 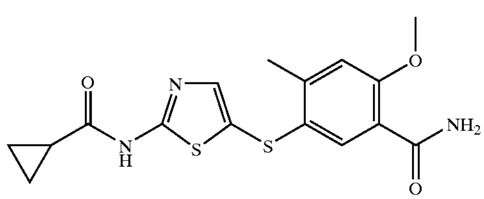 | 364.1 |

-continued

| Ex. No. | Structure | MS (M + H)+ |
|---|---|---|
| 236 | 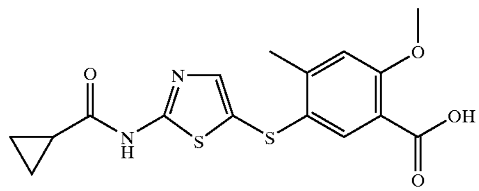 | 365.06 |
| 237 | 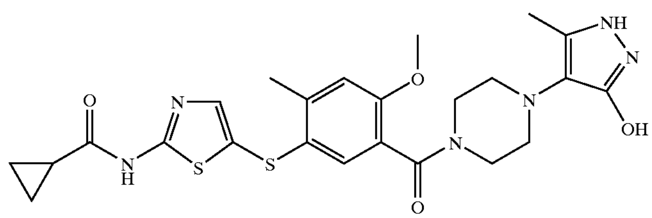 | 529.19 |
| 238 | 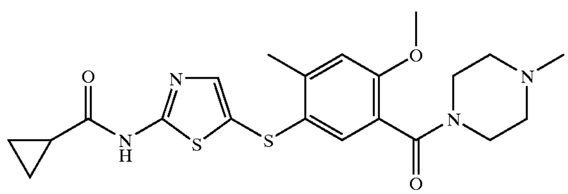 | 447.21 |
| 239 | 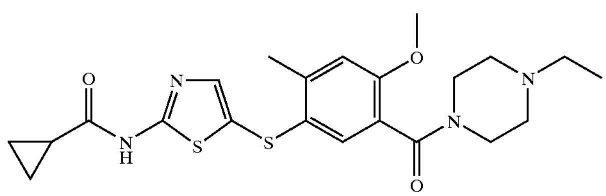 | 461.33 |
| 240 | 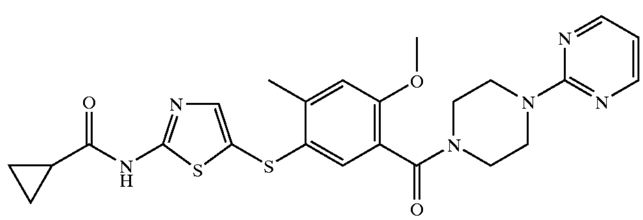 | 511.10 |
| 241 | 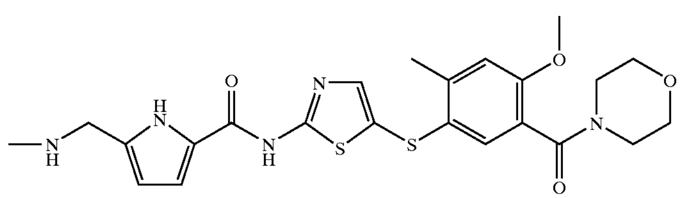 | 502.17 |
| 242 | 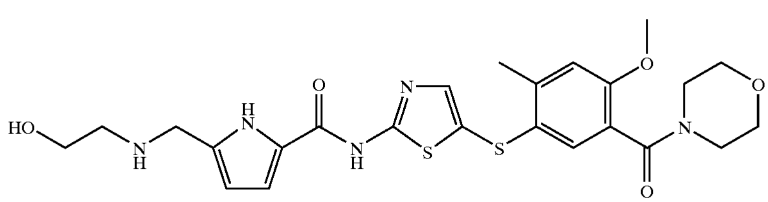 | 532.19 |

-continued

| Ex. No. | Structure | MS (M + H)+ |
|---|---|---|
| 243 | 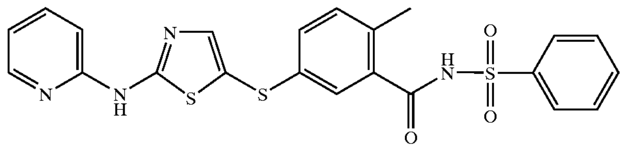 | 483.24 |
| 244 | 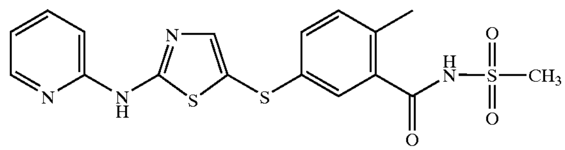 | 421.22 |
| 245 | 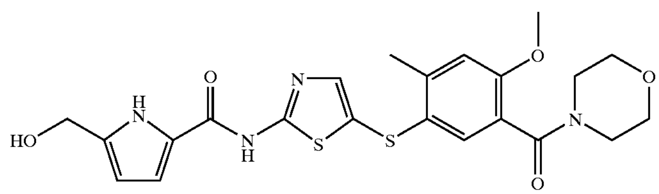 | 489.20 |
| 246 | 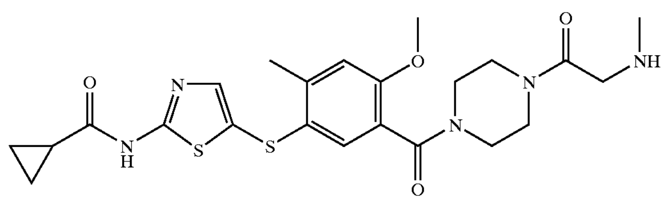 | 504.14 |
| 247 | 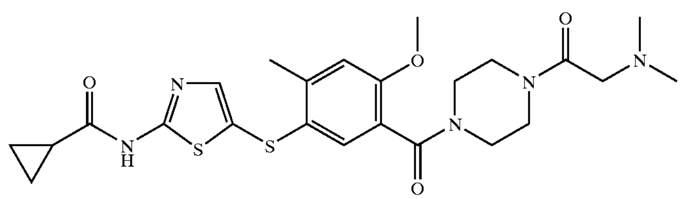 | 518.22 |
| 248 | 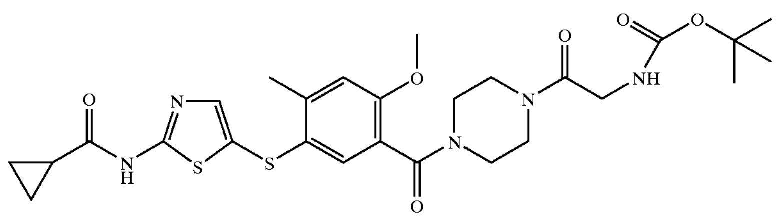 | 590.21 |
| 249 | 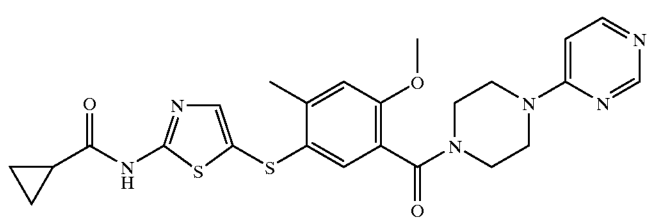 | 511.15 |
| 250 | 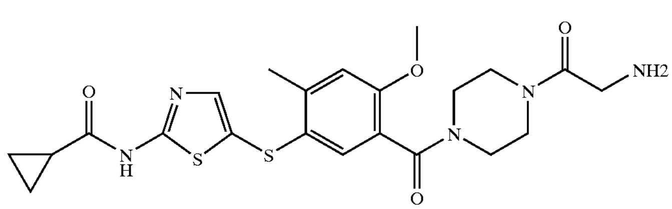 | 490.21 |

| Ex. No. | Structure | MS (M + H)+ |
|---|---|---|
| 251 | 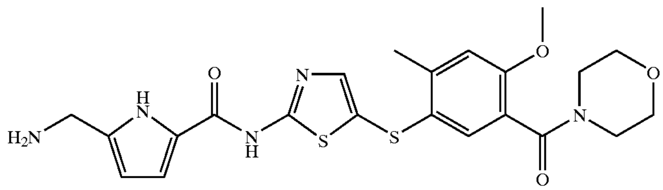 | 488.14 |
| 252 | 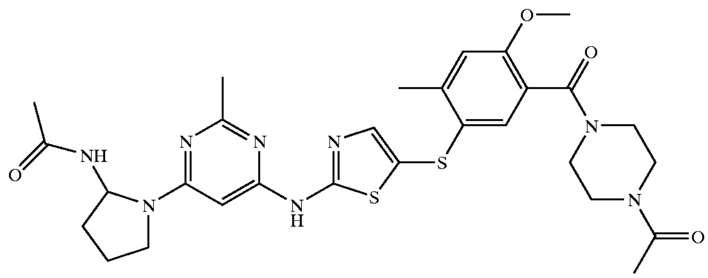 | 625.28 |
| 253 | 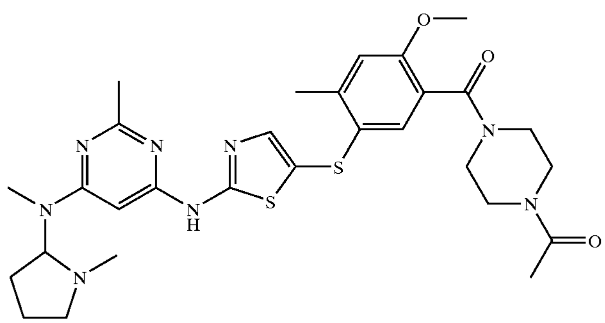 | 611.30 |
| 254 | 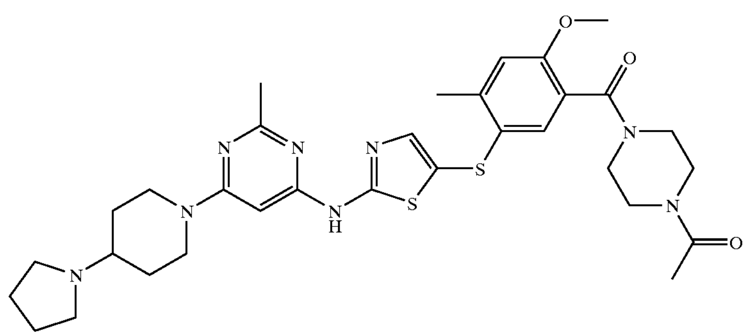 | 651.19 |
| 255 | 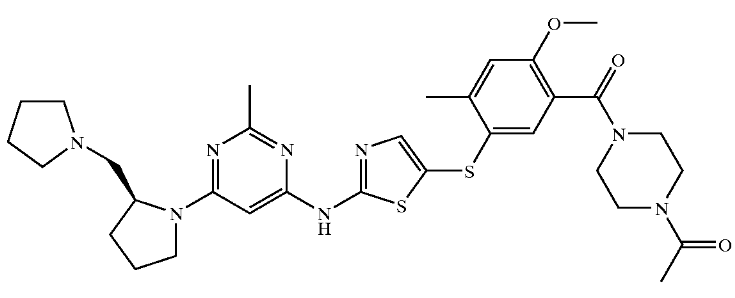 | 651.17 |

-continued

| Ex. No. | Structure | MS (M + H)+ |
|---|---|---|
| 256 | 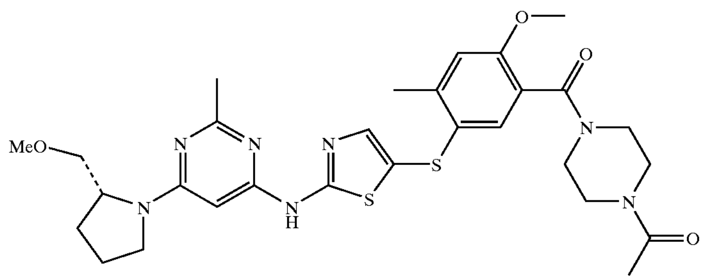 | 612.14 |
| 257 | 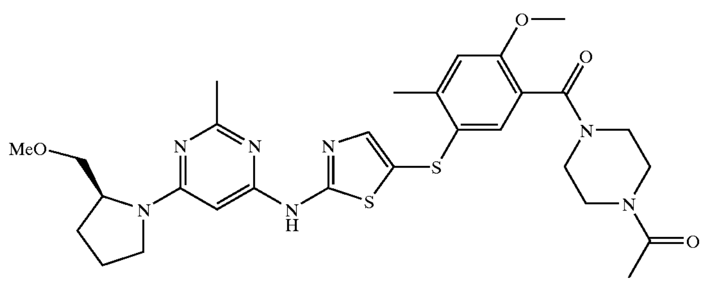 | 612.14 |
| 258 | 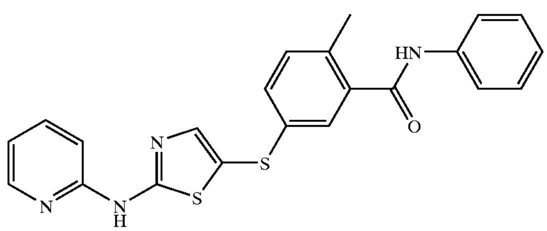 | 419.2 |
| 259 | 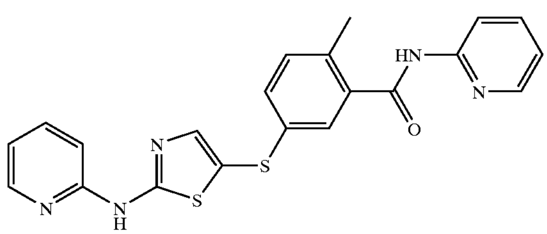 | 420.22 |
| 260 | 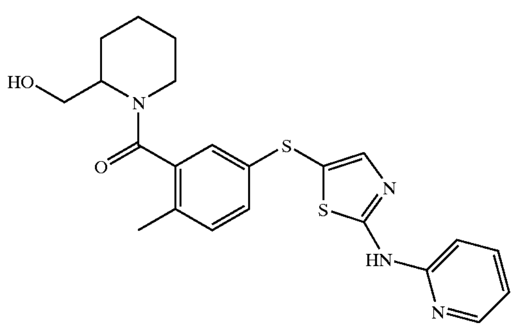 | 441.3 |

-continued

| Ex. No. | Structure | MS (M + H)+ |
|---|---|---|
| 261 | 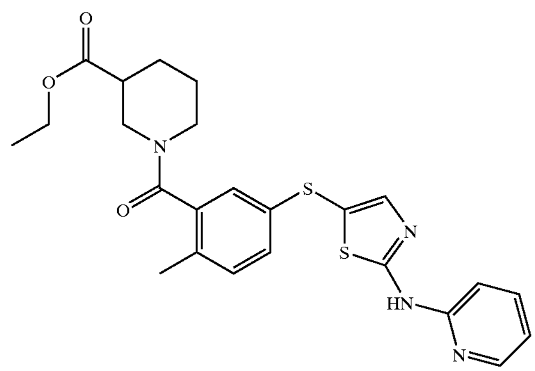 | 483.4 |
| 262 | 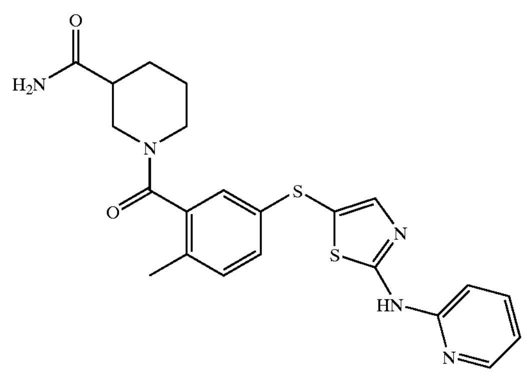 | 454.3 |
| 263 | 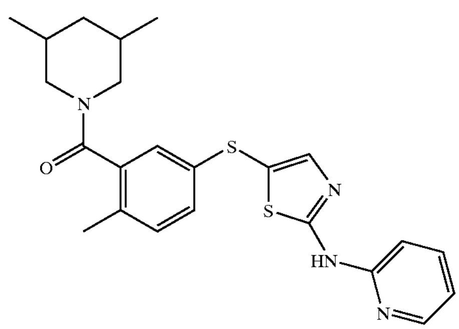 | 439.4 |
| 264 | 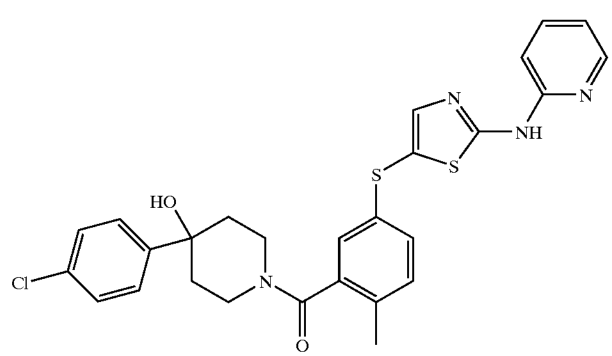 | 535.3 |

-continued

| Ex. No. | Structure | MS (M + H)+ |
|---|---|---|
| 265 | 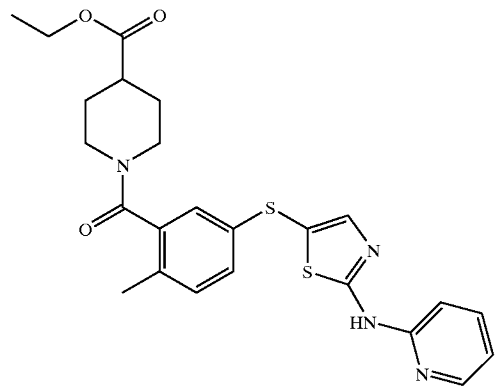 | 483.4 |
| 266 | 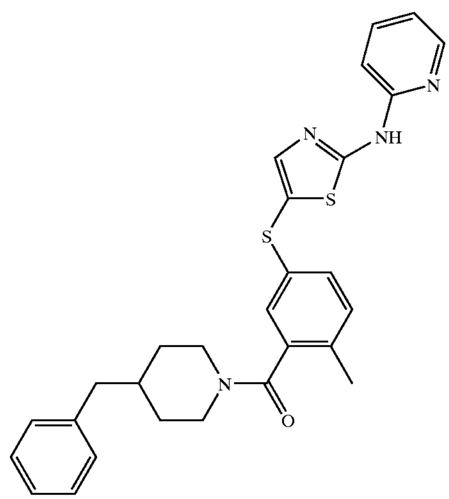 | 499.4 |
| 267 | 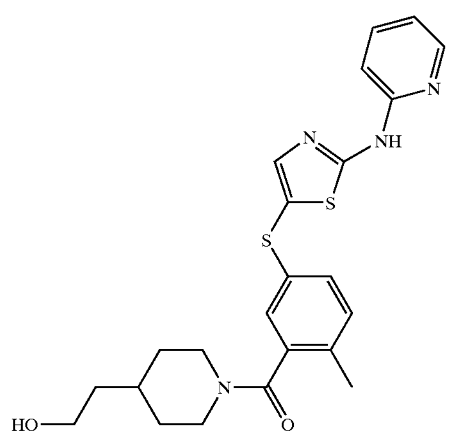 | 453.4 |
| 268 | 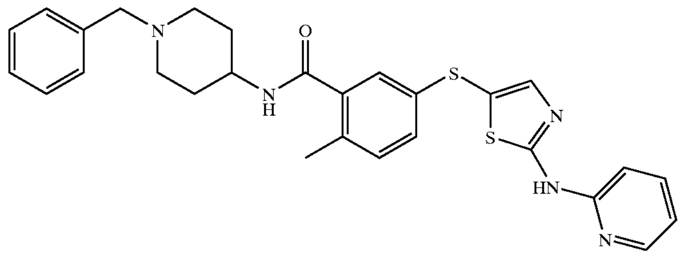 | 516.4 |

-continued

| Ex. No. | Structure | MS (M + H)+ |
|---|---|---|
| 269 | 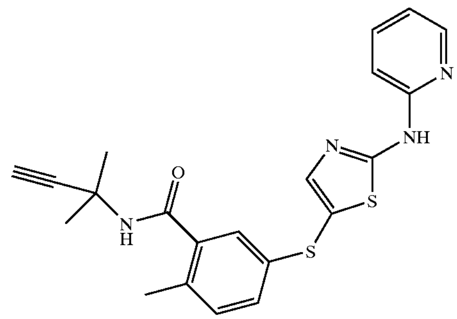 | 407.3 |
| 270 | 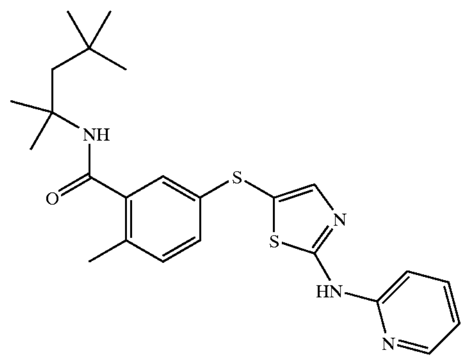 | 453.4 |
| 271 | 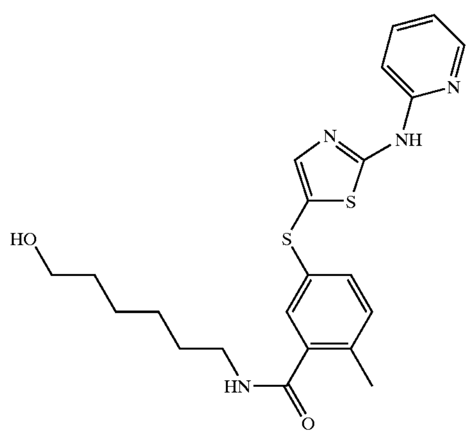 | 441.4 |
| 272 | 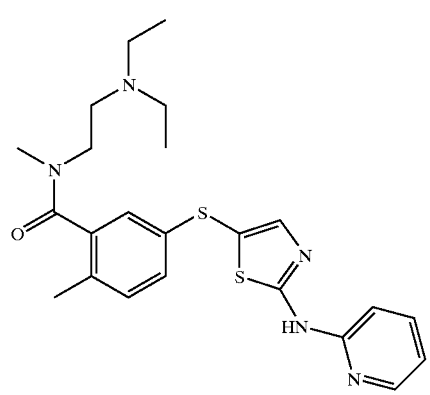 | 456.4 |

-continued

| Ex. No. | Structure | MS (M + H)+ |
|---|---|---|
| 273 | 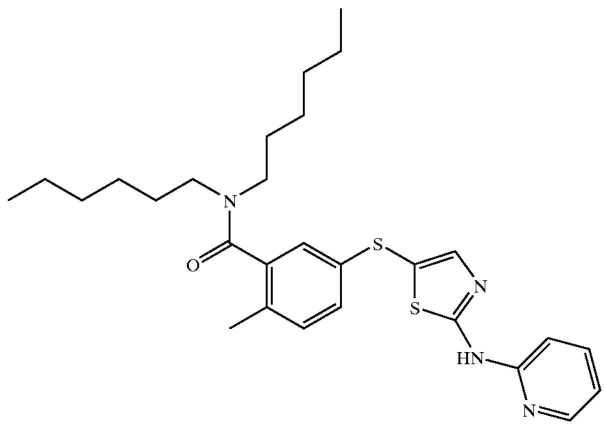 | 511.5 |
| 274 | 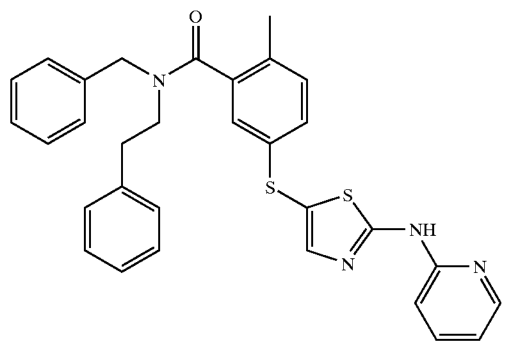 | 535.4 |
| 275 | 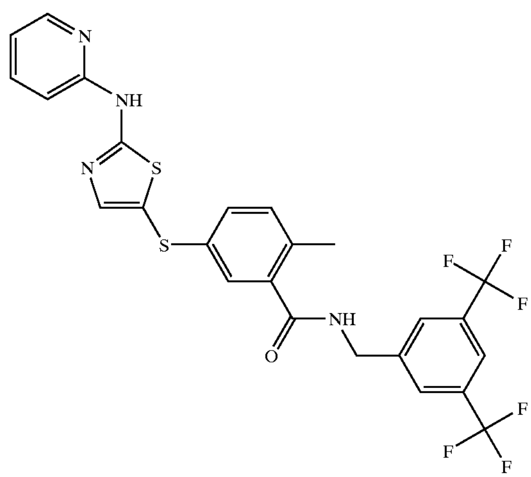 | 567.3 |

-continued
| Ex. No. | Structure | MS (M + H)+ |
|---|---|---|
| 276 | 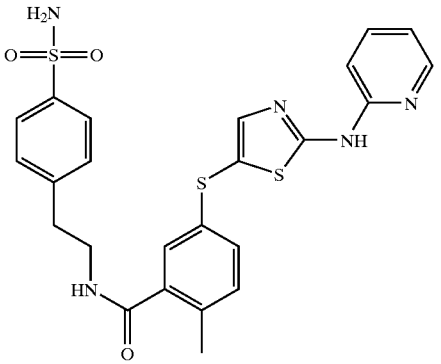 | 524.3 |
| 277 | 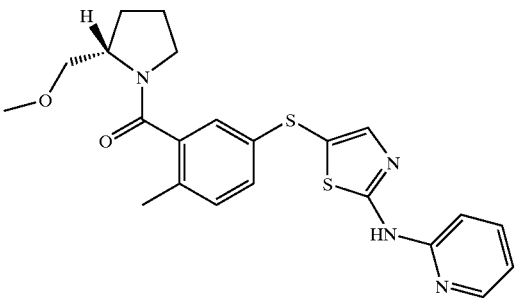 | 441.4 |
| 278 | 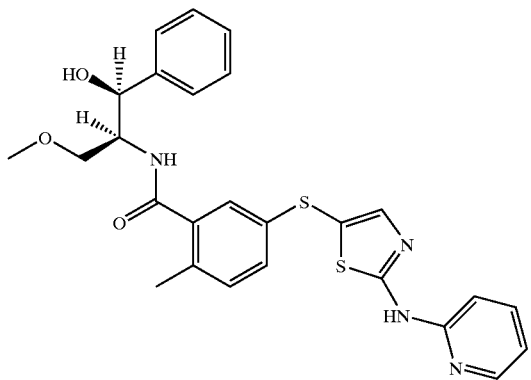 | 507.3 |
| 279 | 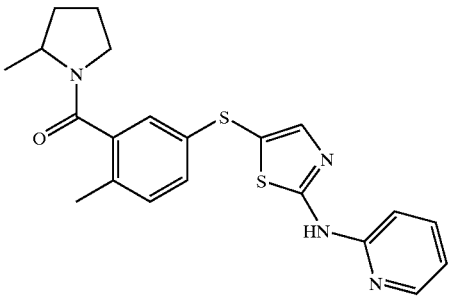 | 409.3 |

-continued

| Ex. No. | Structure | MS (M + H)+ |
|---|---|---|
| 280 | 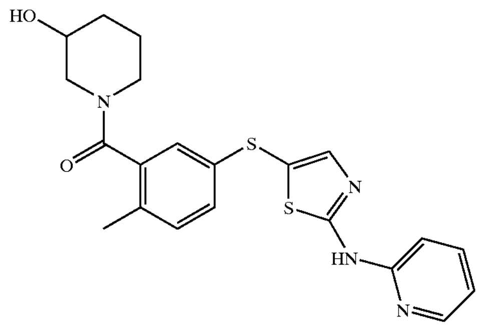 | 427.3 |
| 281 | 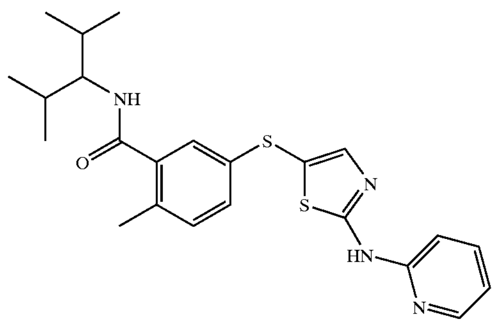 | 441.4 |
| 282 | 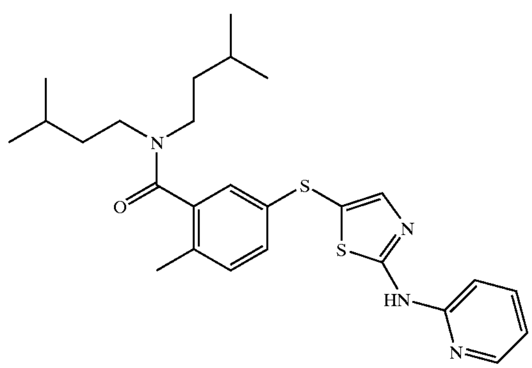 | 483.4 |
| 283 | 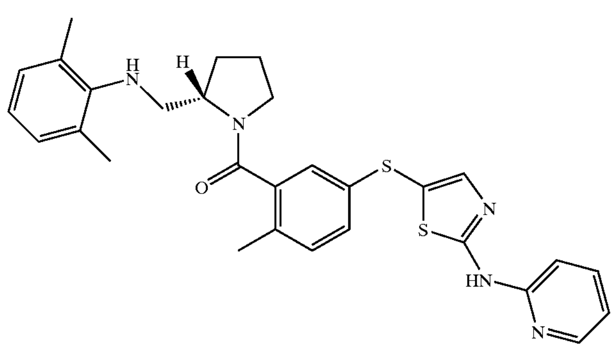 | 530.4 |

| Ex. No. | Structure | MS (M + H)+ |
|---|---|---|
| 284 | 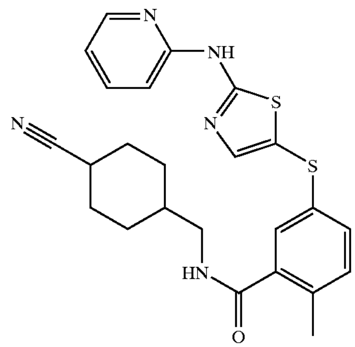 | 462.4 |
| 285 | 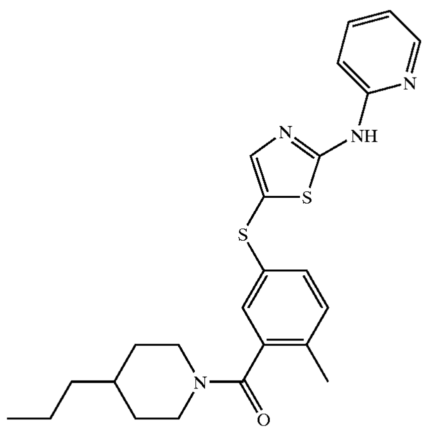 | 453.4 |
| 286 | 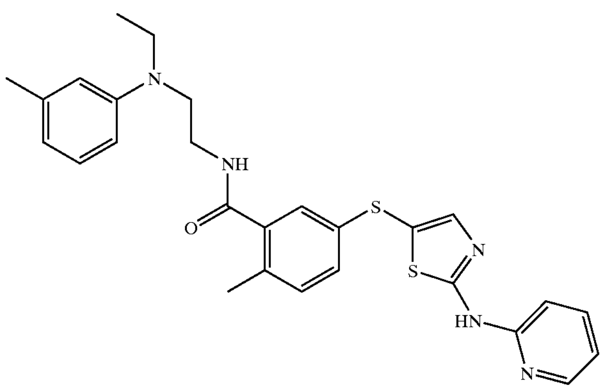 | 502.4 |
| 287 | 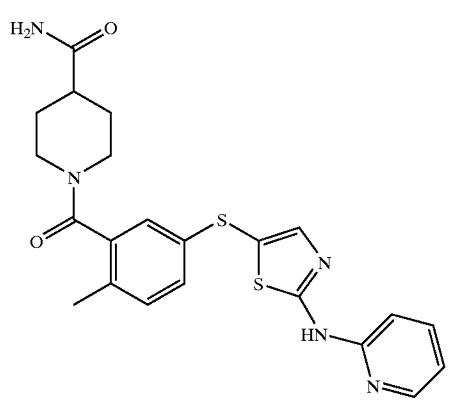 | 452.3 |

| Ex. No. | Structure | MS (M + H)+ |
|---|---|---|
| 288 | 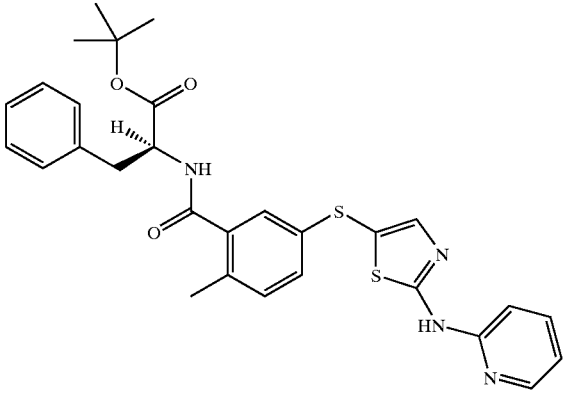 | 545.4 |
| 289 | 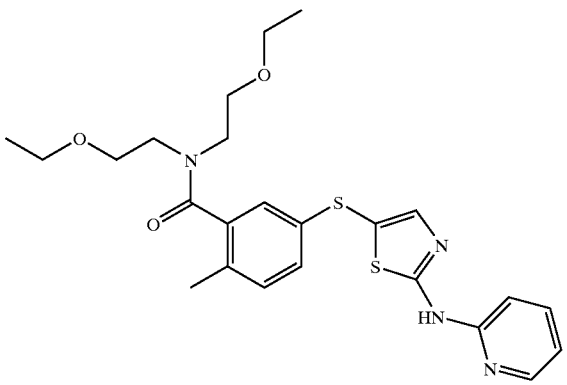 | 487.4 |
| 290 | 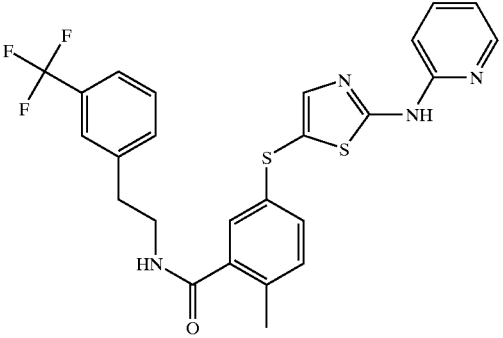 | 513.3 |
| 291 | 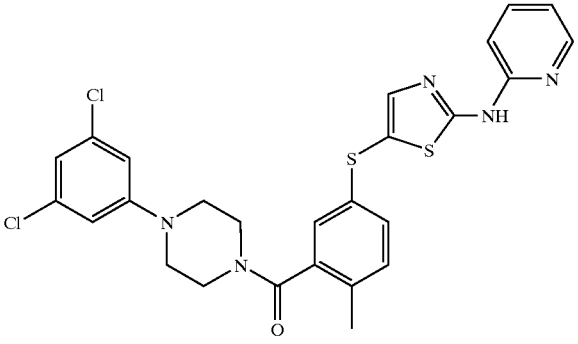 | 554.2 |

| Ex. No. | Structure | MS (M + H)+ |
|---|---|---|
| 292 | 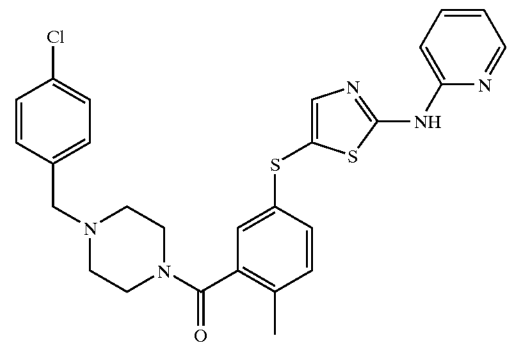 | 534.3 |
| 293 | 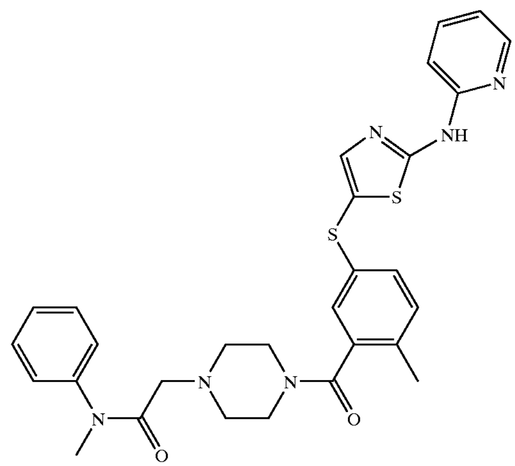 | 559.4 |
| 294 | 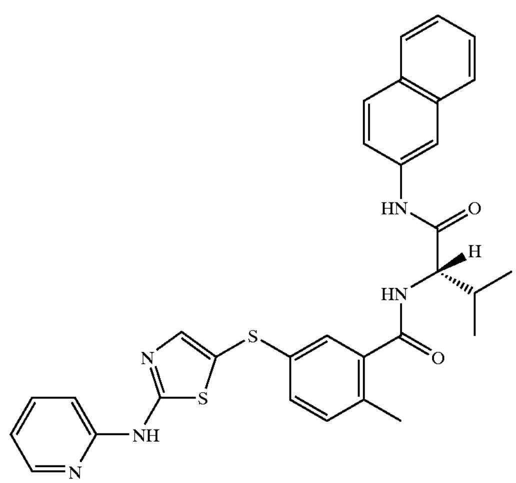 | 566.4 |

-continued
| Ex. No. | Structure | MS (M + H)+ |
|---|---|---|
| 295 | 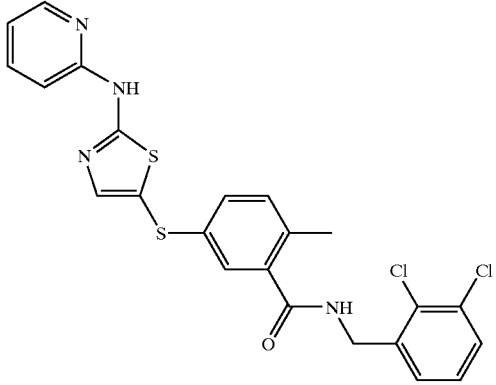 | 501.1 |
| 296 | 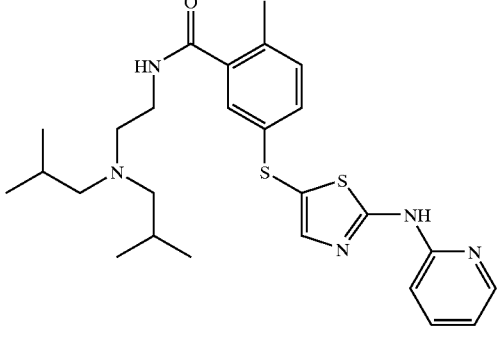 | 498.4 |
| 297 | 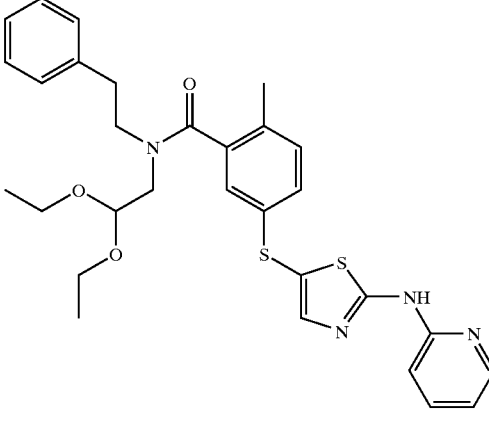 | 535.2 |
| 298 | 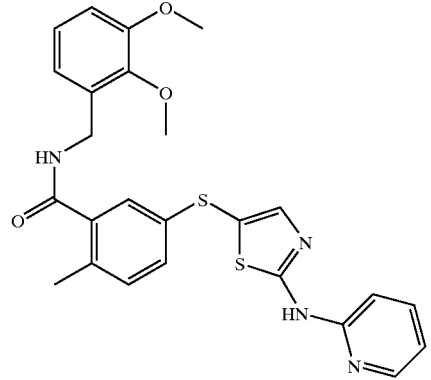 | 491.4 |

US 6,958,336 B2
145 146
-continued
| Ex. No. | Structure | MS (M + H)+ |
|---|---|---|
| 299 | 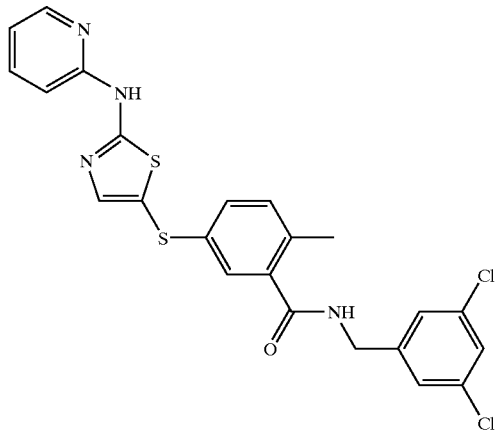 | 499.2 |
| 300 | 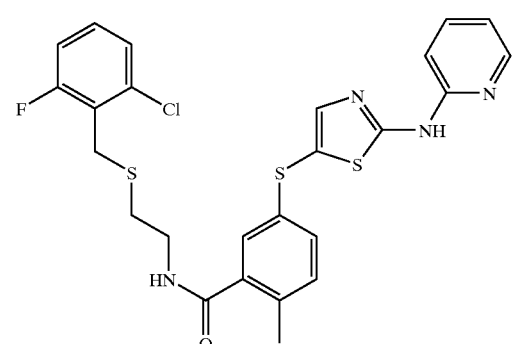 | 543.3 |
| 301 | 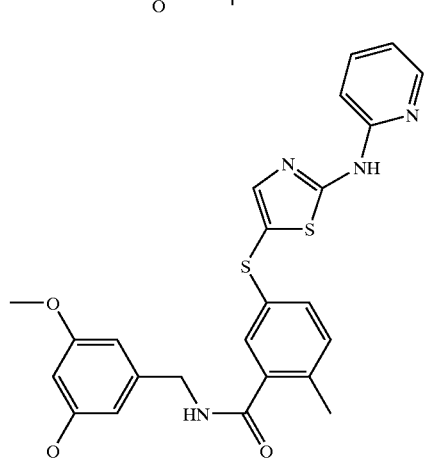 | 491.4 |
| 302 | 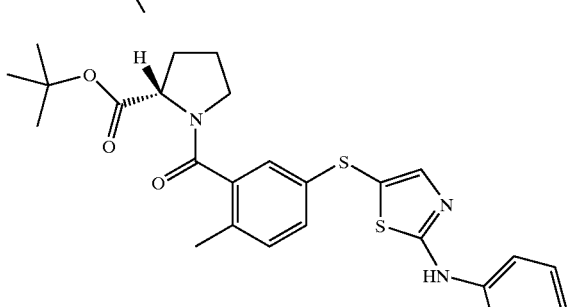 | 495.4 |

-continued
| Ex. No. | Structure | MS (M + H)+ |
|---|---|---|
| 303 | 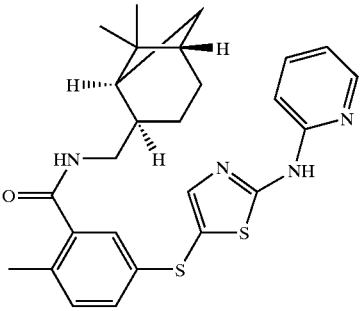 | 477.4 |
| 304 | 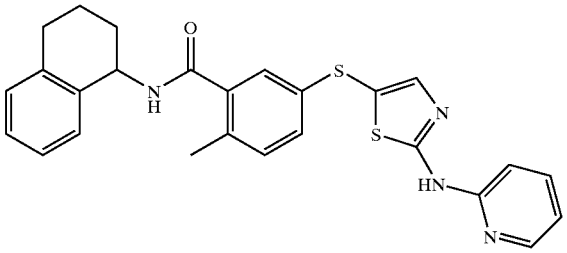 | 473.3 |
| 305 | 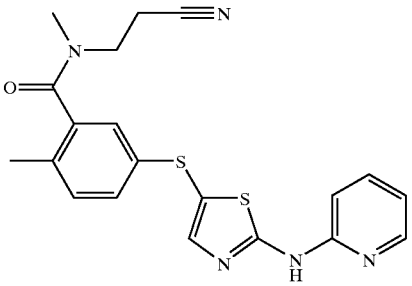 | 410.3 |
| 306 | 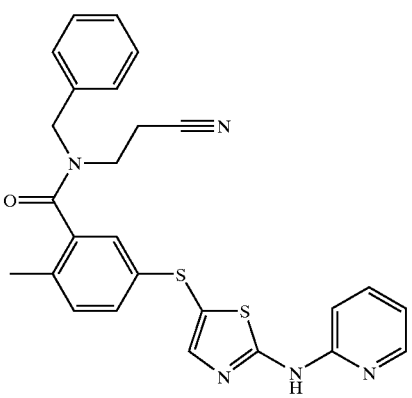 | 486.2 |

-continued

| Ex. No. | Structure | MS (M + H)+ |
|---|---|---|
| 307 | 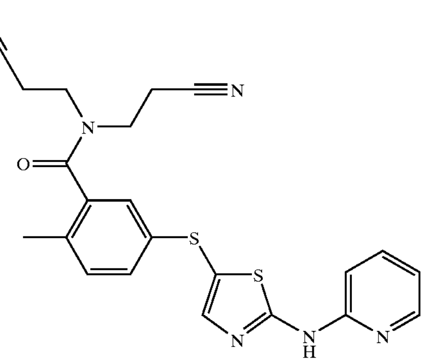 | 449.2 |
| 308 | 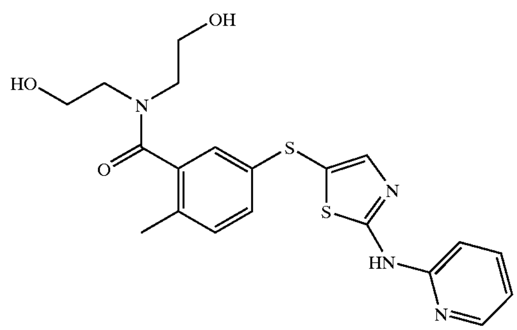 | 431.3 |
| 309 | 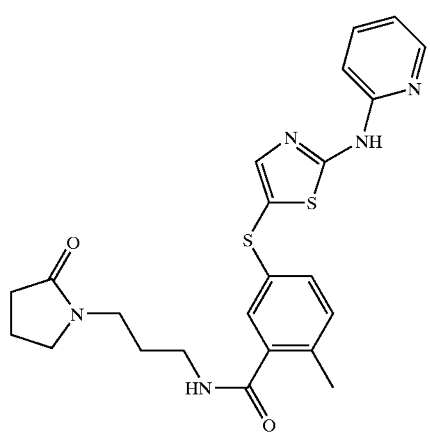 | 468.4 |
| 310 | 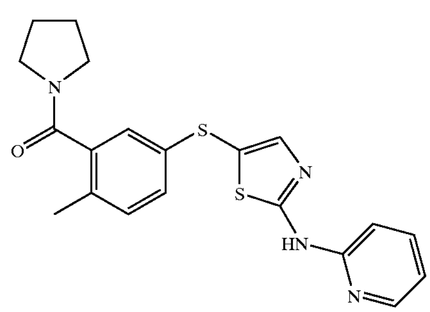 | 397.3 |

-continued

| Ex. No. | Structure | MS (M + H)+ |
|---|---|---|
| 311 | 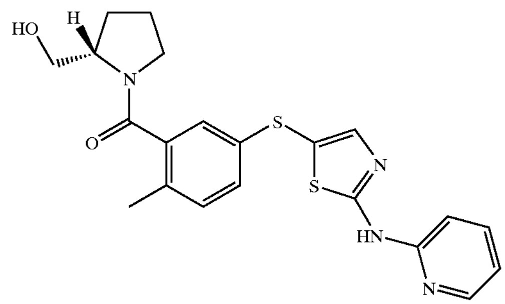 | 425.3 |
| 312 | 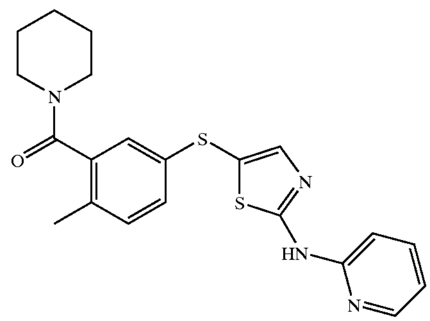 | 411.3 |
| 313 | 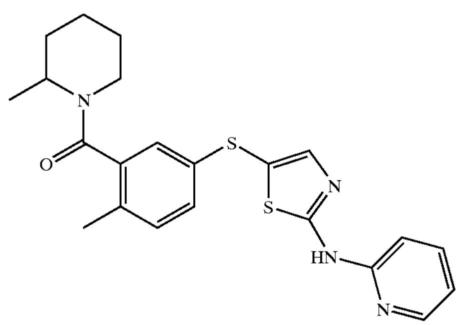 | 425.3 |
| 314 | 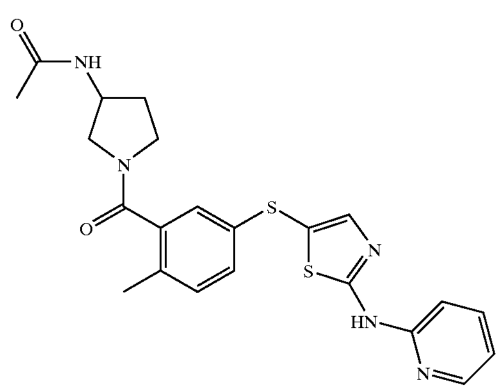 | 452.4 |

-continued
| Ex. No. | Structure | MS (M + H)+ |
|---|---|---|
| 315 | 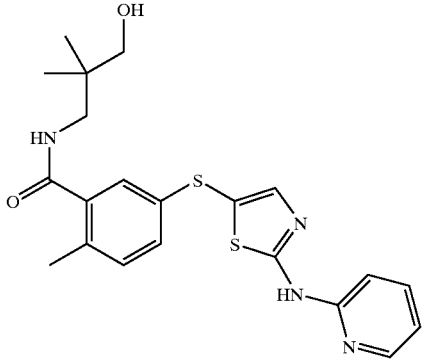 | 429.4 |
| 316 | 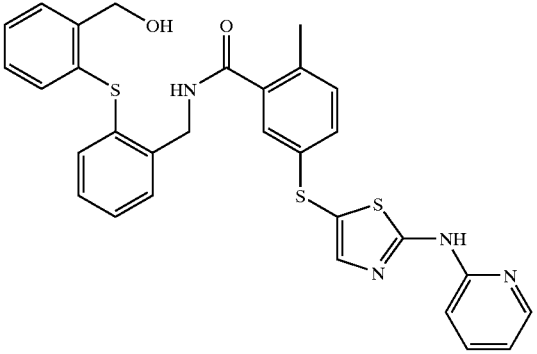 | 571.1 |
| 317 | 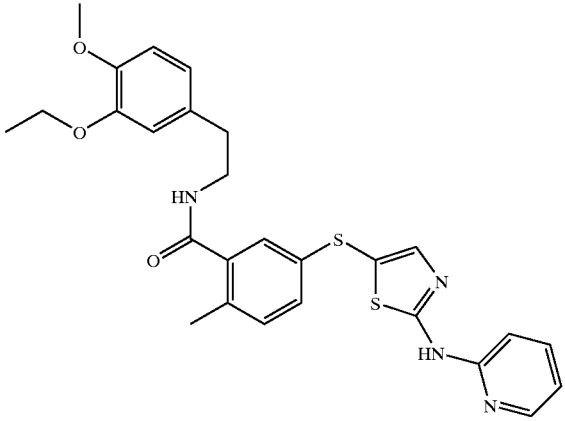 | 521.4 |
| 318 | 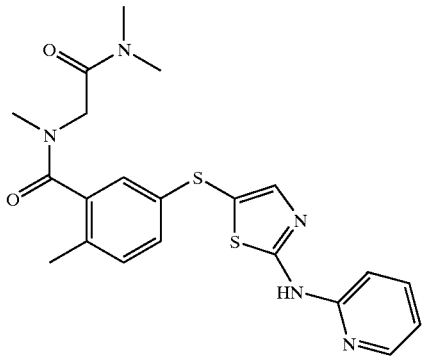 | 442.2 |

-continued

| Ex. No. | Structure | MS (M + H)+ |
|---|---|---|
| 319 | 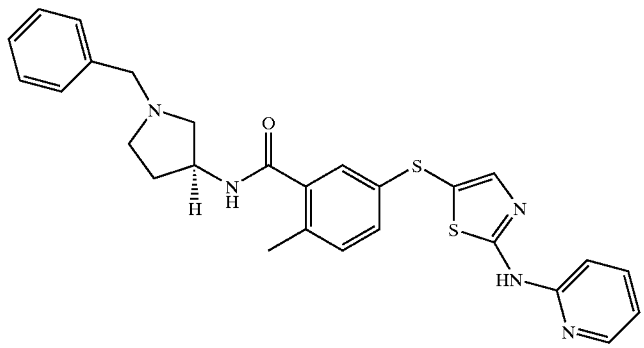 | 500.4 |
| 320 | 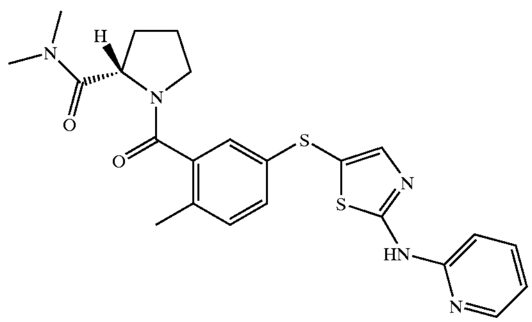 | 468.4 |
| 321 | 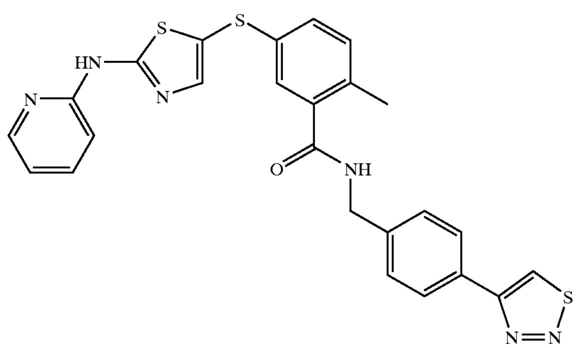 | 517.1 |
| 322 | 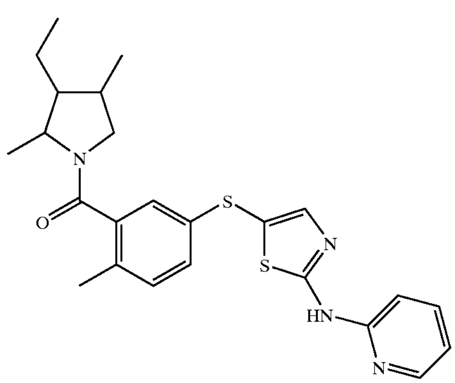 | 453.4 |

-continued

| Ex. No. | Structure | MS (M + H)+ |
|---|---|---|
| 323 | 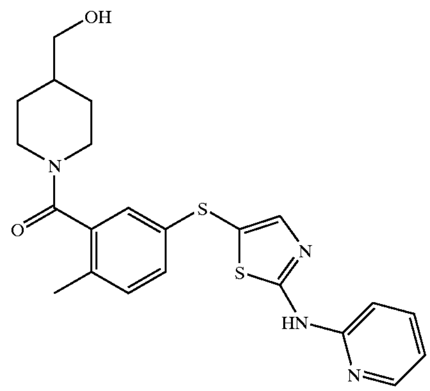 | 441.4 |
| 324 | 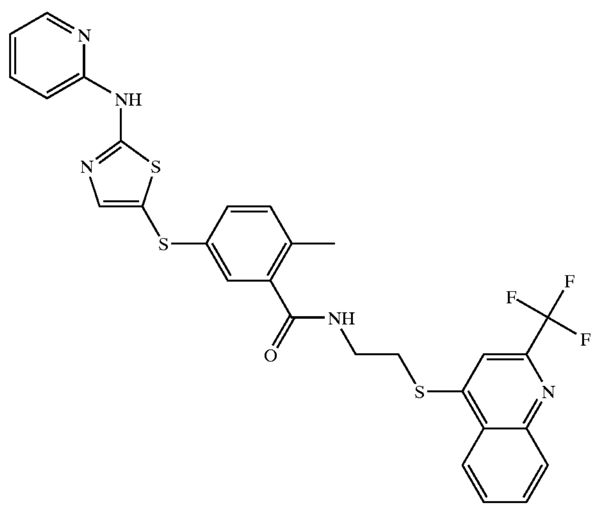 | 598.1 |
| 325 | 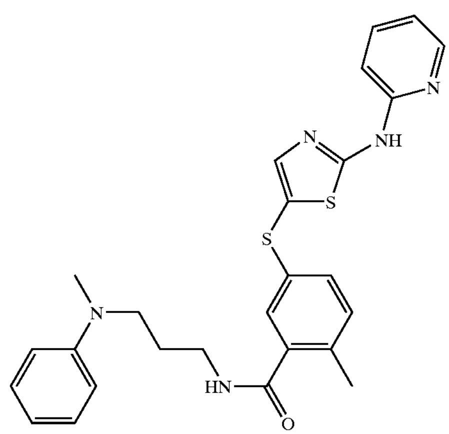 | 488.3 |

-continued

| Ex. No. | Structure | MS (M + H)+ |
|---|---|---|
| 326 | 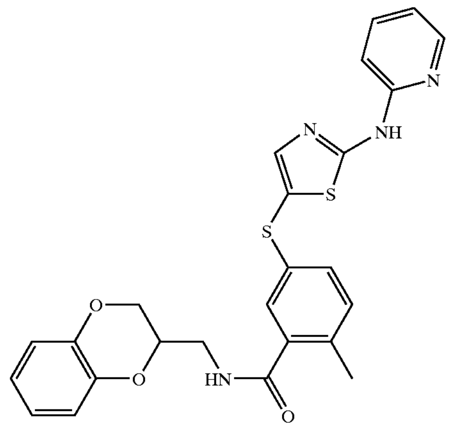 | 489.3 |
| 327 | 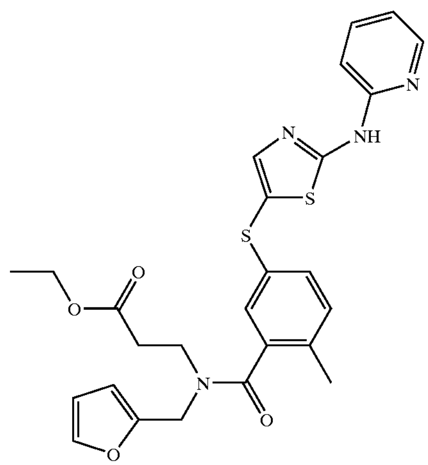 | 591.6 |
| 328 | 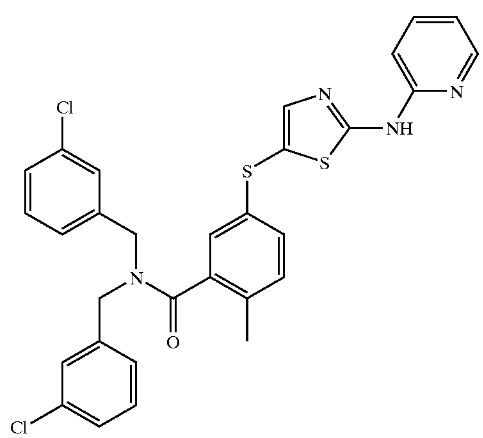 | 589.3 |

-continued
| Ex. No. | Structure | MS (M + H)+ |
|---|---|---|
| 329 | 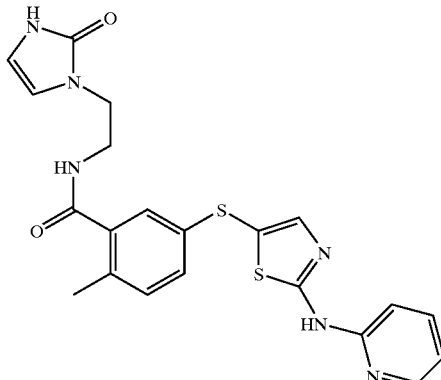 | 453.3 |
| 330 | 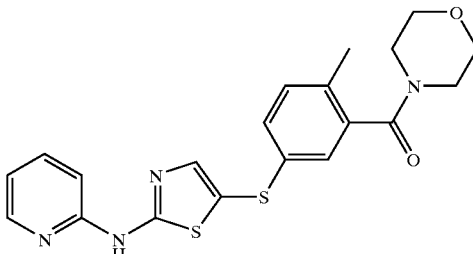 | 413.16 |
| 331 | 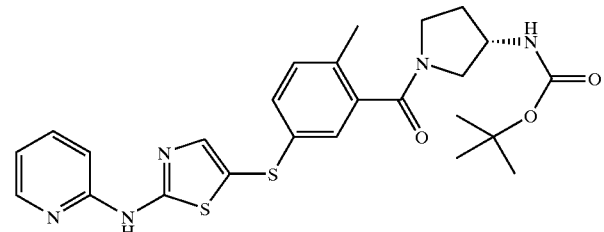 | 512.21 |
| 332 | 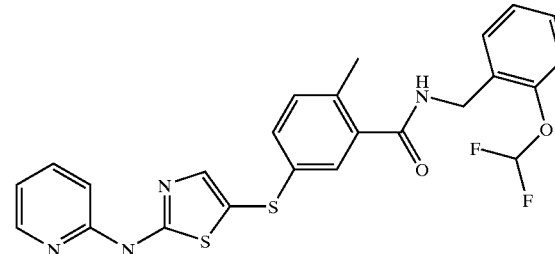 | 499.14 |
| 333 | 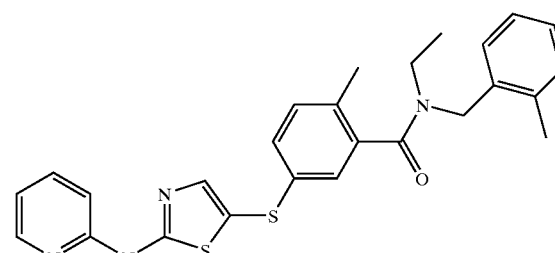 | 475.2 |

-continued

| Ex. No. | Structure | MS (M + H)+ |
|---|---|---|
| 334 | 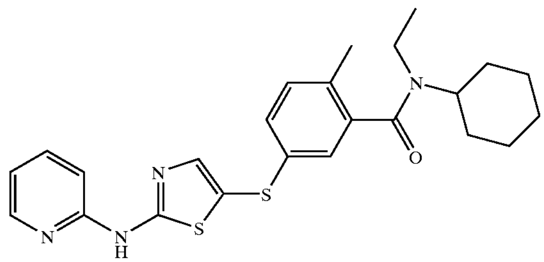 | 453.22 |
| 335 | 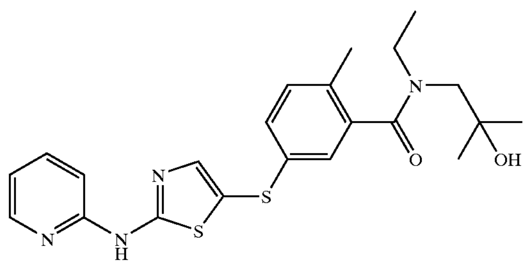 | 443.38 |
| 336 | 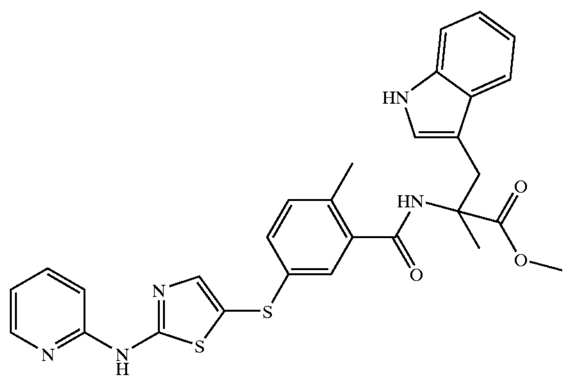 | 558.22 |
| 337 | 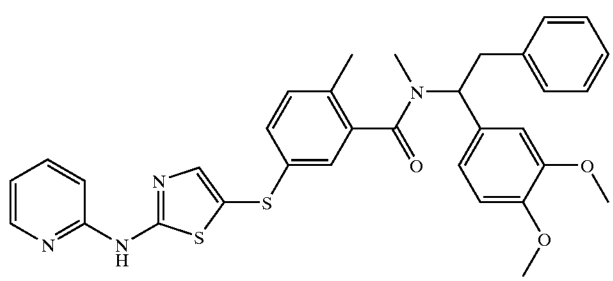 | 597.52 |
| 338 | 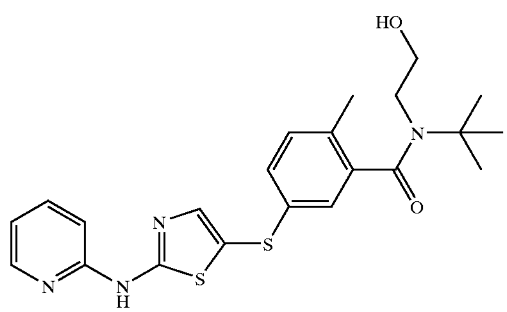 | 443.24 |

-continued

| Ex. No. | Structure | MS (M + H)+ |
|---|---|---|
| 339 | 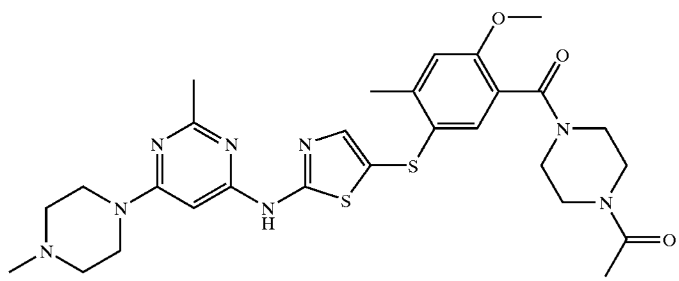 | 597.37 |
| 340 | 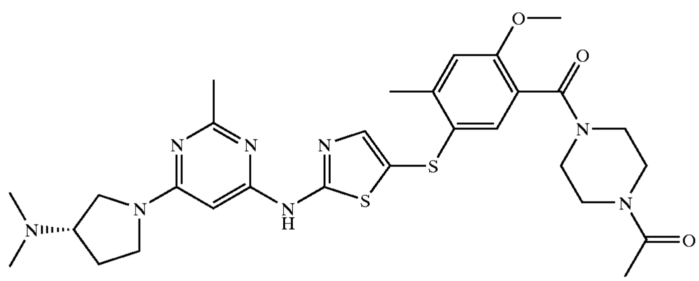 | 611.47 |
| 341 | 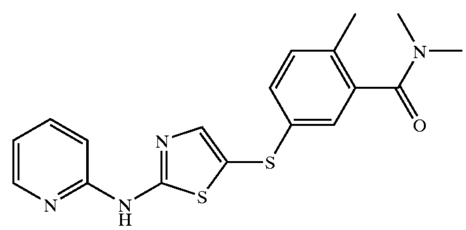 | 371.24 |
| 342 | 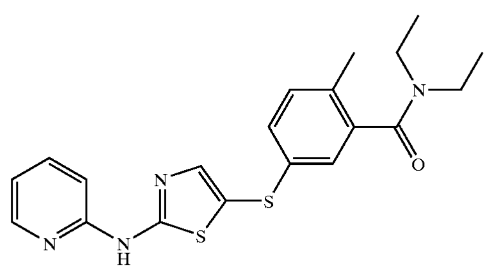 | 399.29 |
| 343 | 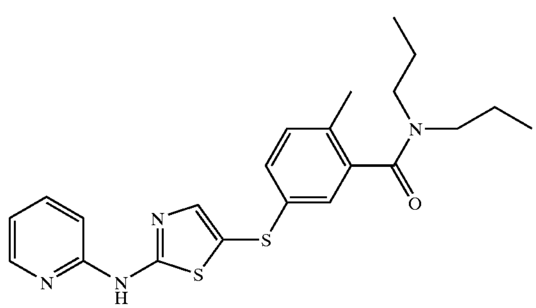 | 427.32 |

-continued

| Ex. No. | Structure | MS (M + H)+ |
|---|---|---|
| 344 | 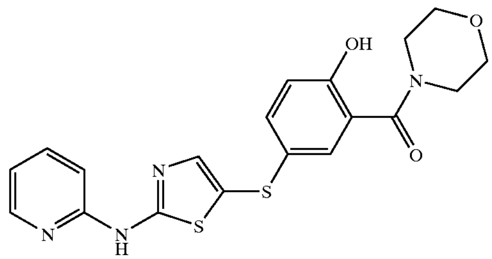 | 415.31 |
| 345 | 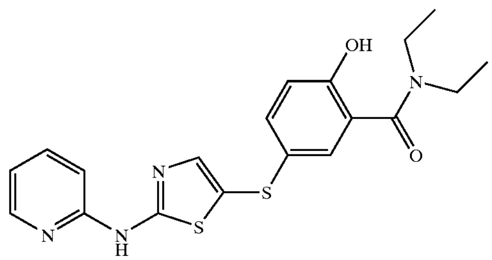 | 401.34 |
| 346 | 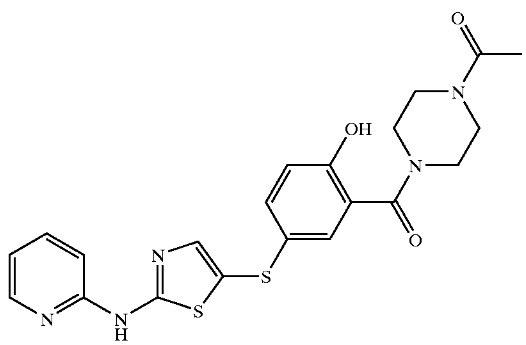 | 456.35 |
| 347 | 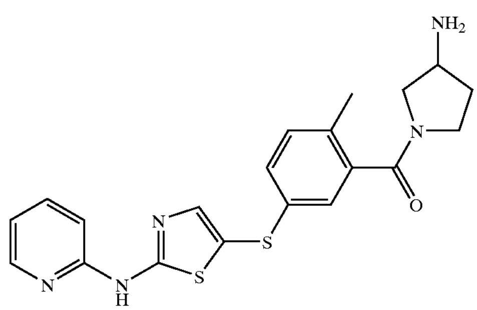 | 412.19 |
| 348 | 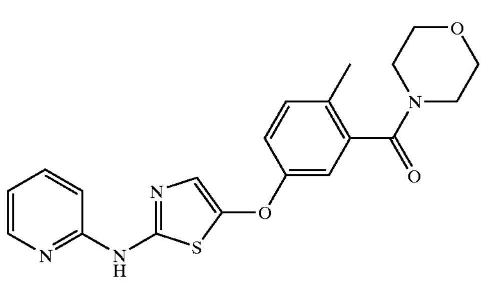 | 397.59 |

-continued

| Ex. No. | Structure | MS (M + H)+ |
|---|---|---|
| 349 | 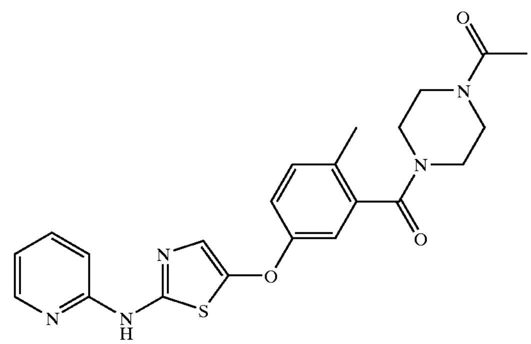 | 438.59 |
| 350 | 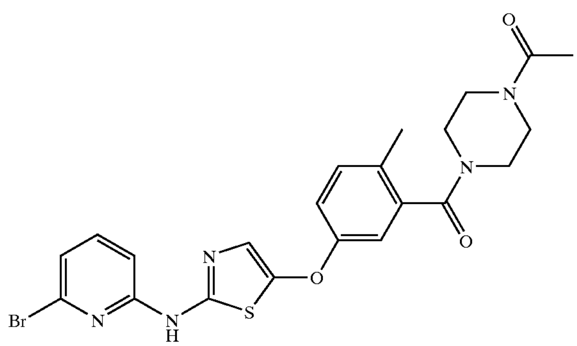 | 516.45 |
| 351 | 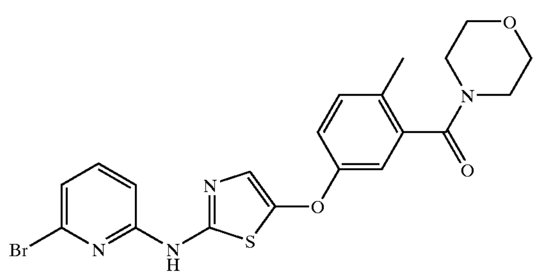 | 477.44 |
| 352 | 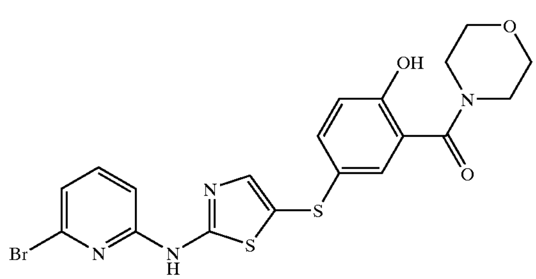 | 495.01 |

| Ex. No. | Structure | MS (M + H)+ |
|---|---|---|
| 353 | 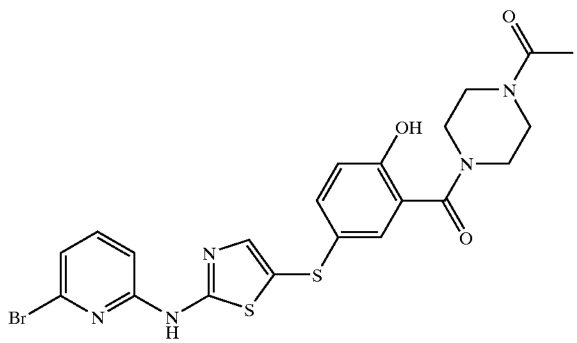 | 535.98 |
| 354 | 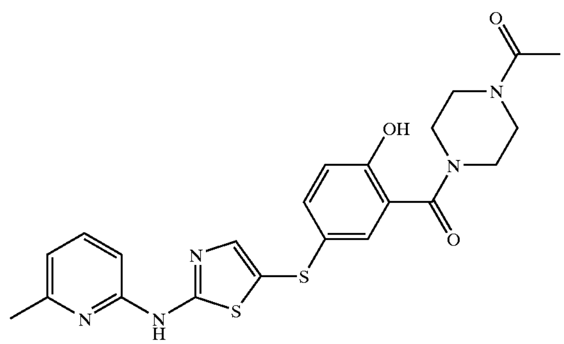 | 470.09 |
| 355 | 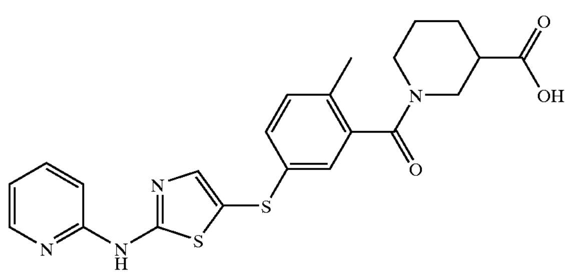 | 455.07 |
| 356 | 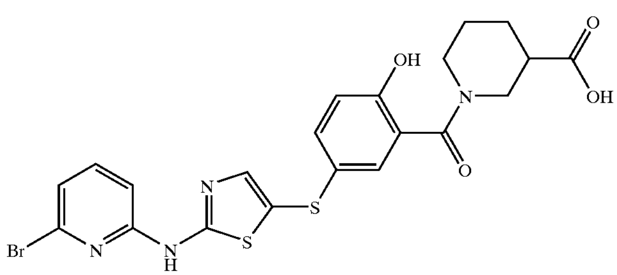 | 537.29 |

-continued
| Ex. No. | Structure | MS (M + H)+ |
|---|---|---|
| 357 | 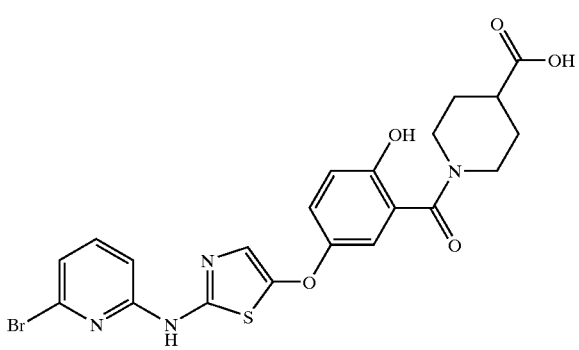 | 537.33 |
| 358 | 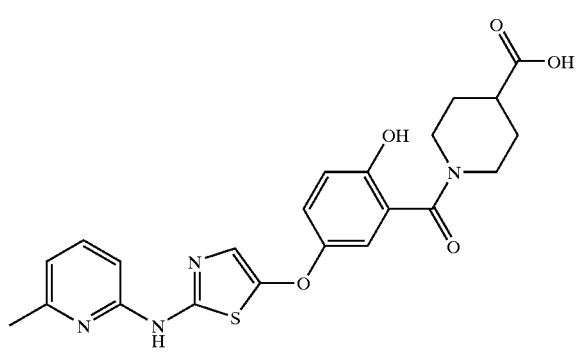 | 471.05 |
| 359 | 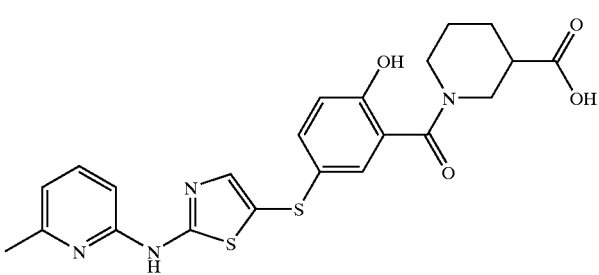 | 471.44 |
| 360 | 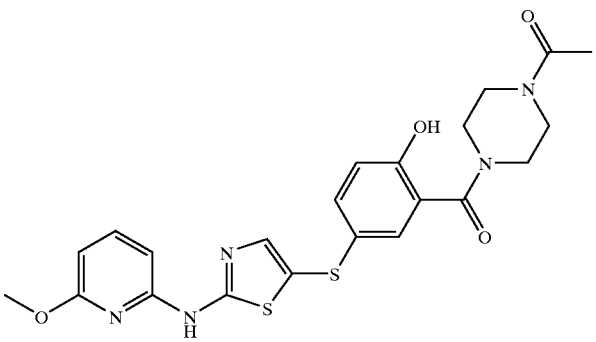 | 486.42 |

| Ex. No. | Structure | MS (M + H)+ |
|---|---|---|
| 361 | (morpholine-pyridine-NH-thiazole-S-phenyl(OH)-C(O)-piperazine-C(O)CH3) | 541.08 |
| 362 | (pyrrolidine-pyridine-NH-thiazole-S-phenyl(OH)-C(O)-piperazine-C(O)CH3) | 525.12 |
| 363 | (4-hydroxypiperidine-pyridine-NH-thiazole-S-phenyl(OH)-C(O)-piperazine-C(O)CH3) | 555.11 |
| 364 | (piperidine-pyridine-NH-thiazole-S-phenyl(OH)-C(O)-piperazine-C(O)CH3) | 539.34 |

-continued
| Ex. No. | Structure | MS (M + H)+ |
|---|---|---|
| 365 | 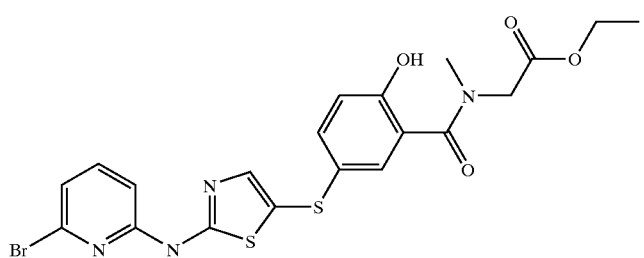 | 524.94 |
| 366 | 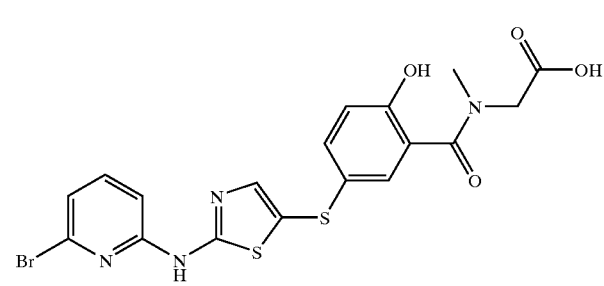 | 496.92 |
| 367 | 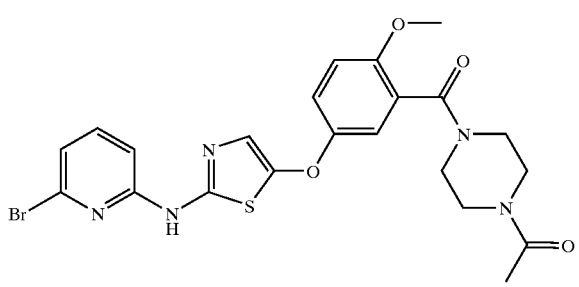 | 534.01 |
| 368 | 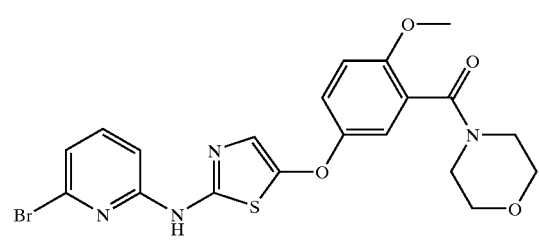 | 492.99 |
| 369 | 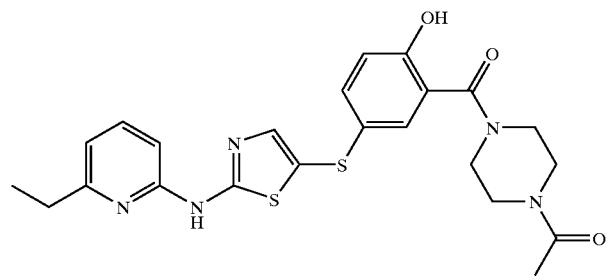 | 484.07 |

| Ex. No. | Structure | MS (M + H)+ |
|---|---|---|
| 370 | 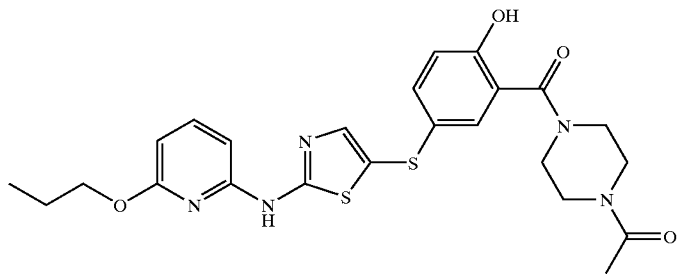 | 514.13 |
| 371 | 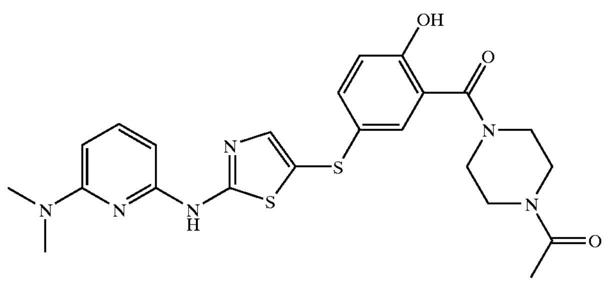 | 499.12 |
| 372 | 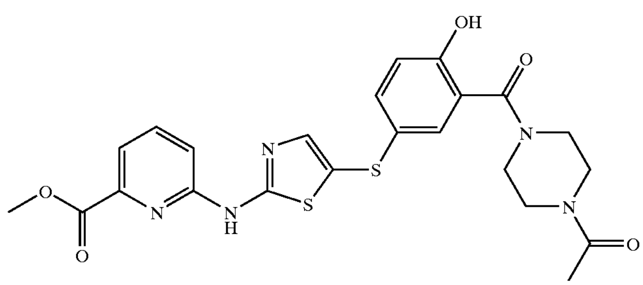 | 514.06 |
| 373 | 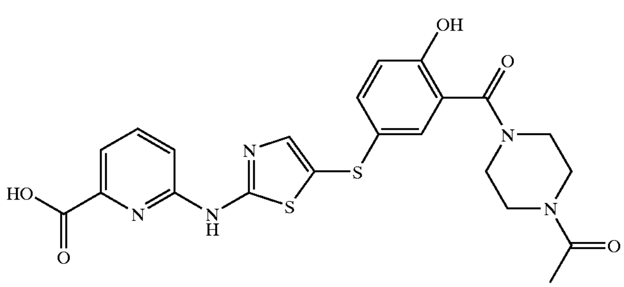 | 500.33 |
| 374 | 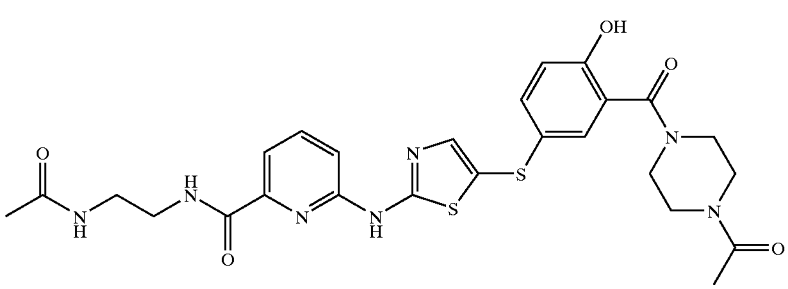 | 584.12 |

-continued

| Ex. No. | Structure | MS (M + H)+ |
|---|---|---|
| 375 | 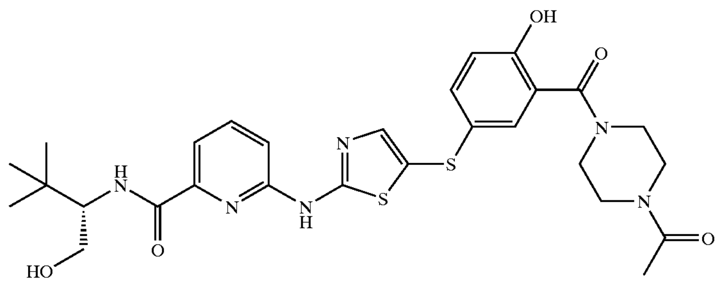 | 599.18 |
| 376 | 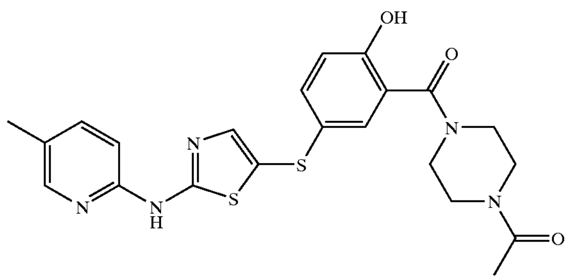 | 470.05 |
| 377 | 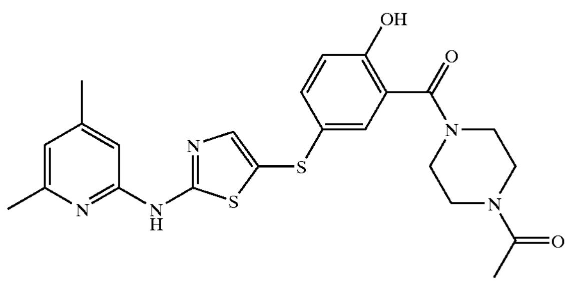 | 484.09 |
| 378 | 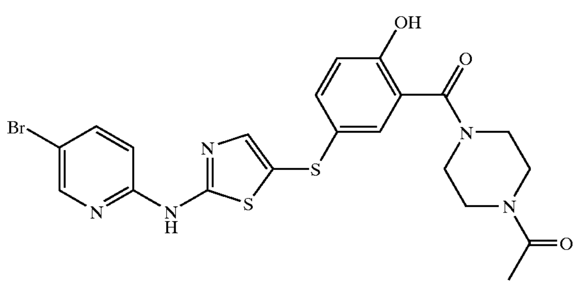 | 535.96 |
| 379 | 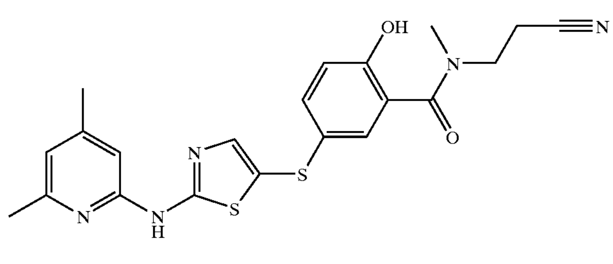 | 440.1 |

-continued

| Ex. No. | Structure | MS (M + H)+ |
|---|---|---|
| 380 | 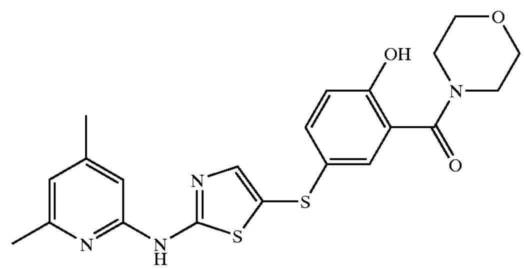 | 443.06 |
| 381 | 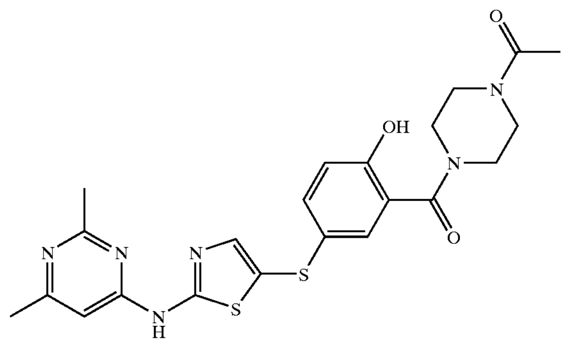 | 485.36 |
| 382 | 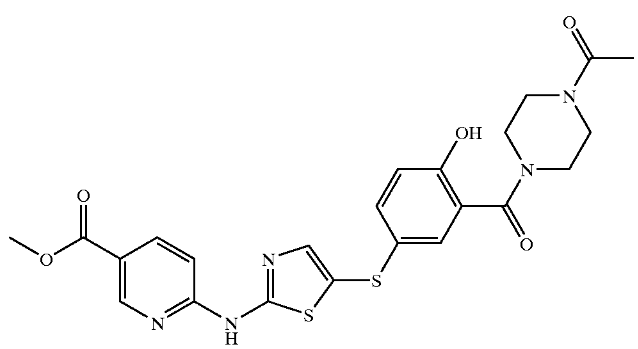 | 514.07 |
| 383 | 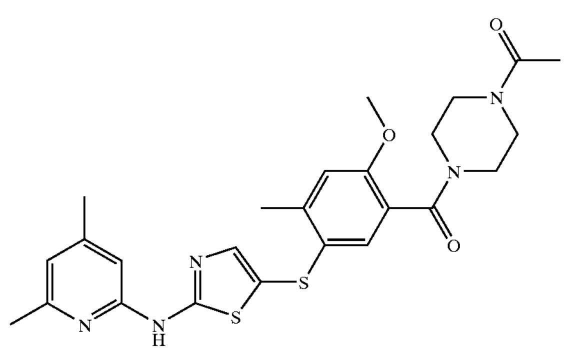 | 512.19 |

-continued

| Ex. No. | Structure | MS (M + H)+ |
|---|---|---|
| 384 | 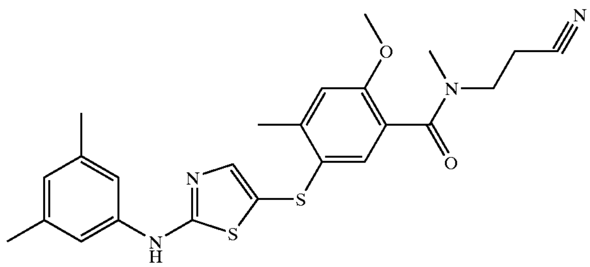 | 468.13 |
| 385 | 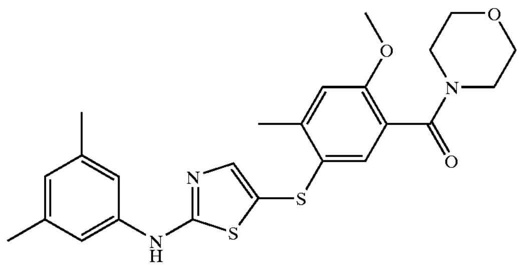 | 471.16 |
| 386 | 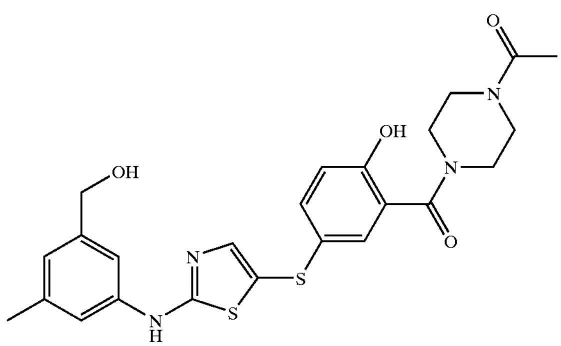 | 500.1 |
| 387 | 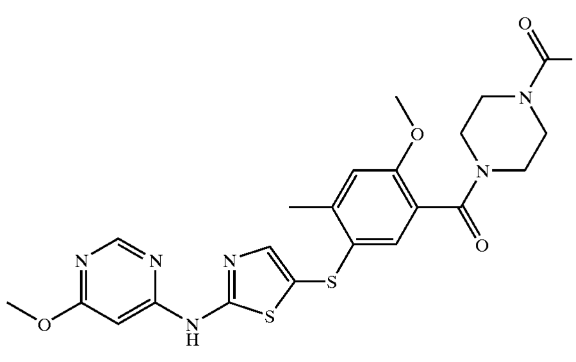 | 515.28 |

-continued

| Ex. No. | Structure | MS (M + H)+ |
|---|---|---|
| 388 | 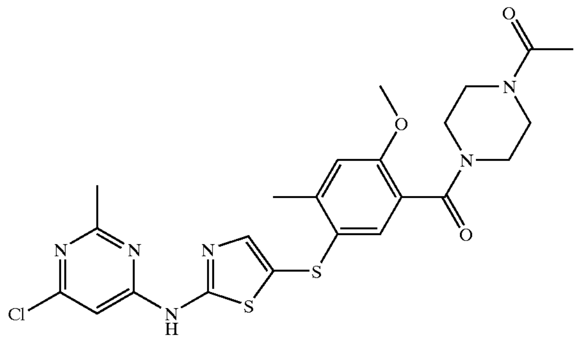 | 533.21 |
| 389 | 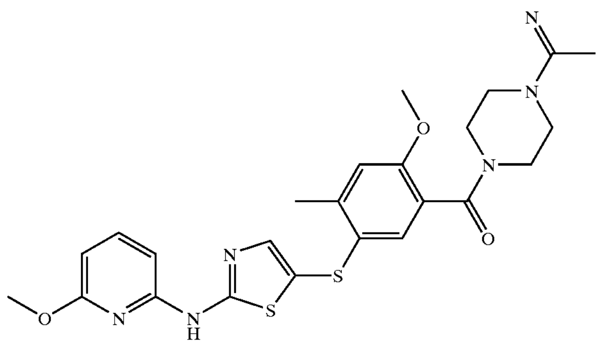 | 514.29 |
| 390 | 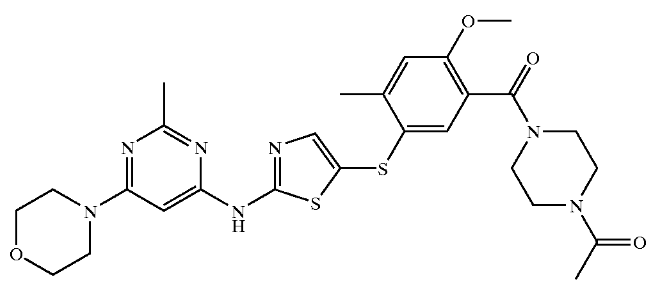 | 584.34 |
| 391 | 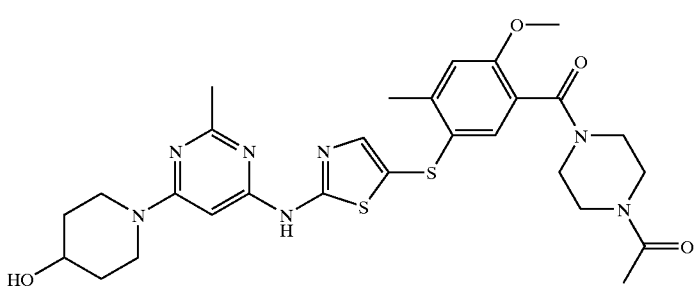 | 598.36 |

-continued
| Ex. No. | Structure | MS (M + H)+ |
|---|---|---|
| 392 | 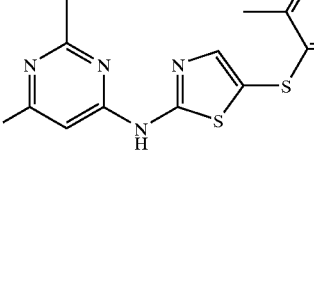 | 625.42 |
| 393 | 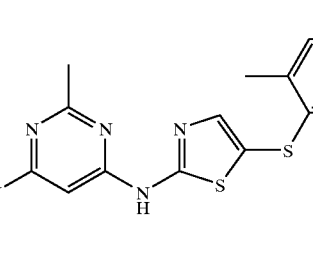 | 619.38 |
| 394 | 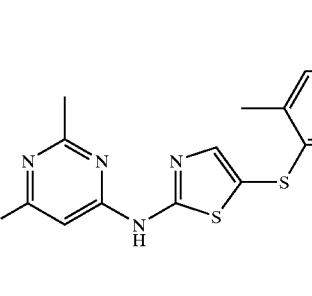 | 585.12 |
| 395 | 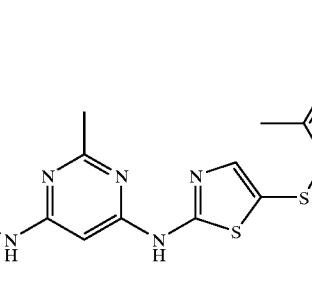 | 599.13 |
| 396 | 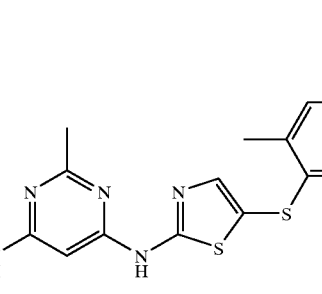 | 558.1 |

-continued

| Ex. No. | Structure | MS (M + H)+ |
|---|---|---|
| 397 | 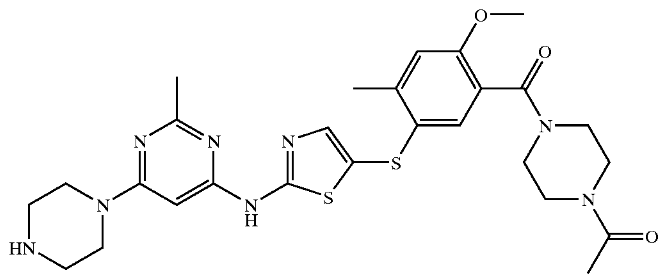 | 583.11 |
| 398 | 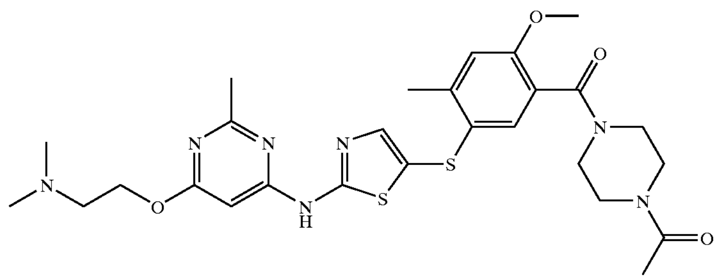 | 586.28 |
| 499 | 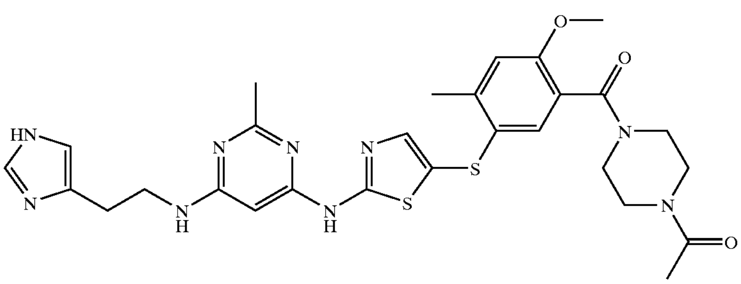 | 608.27 |
| 400 | 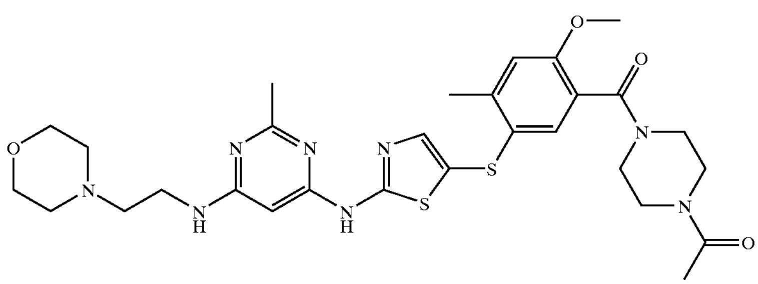 | 627.3 |
| 401 | 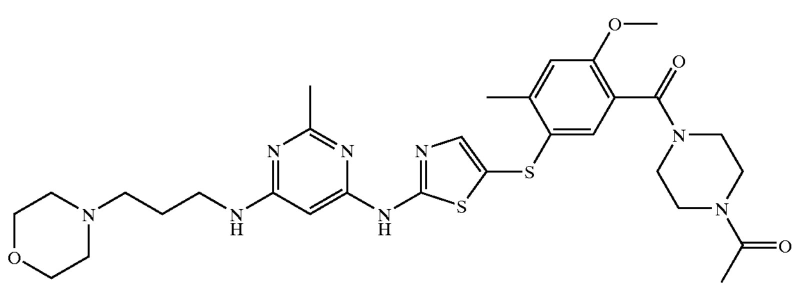 | 641.34 |

-continued
| Ex. No. | Structure | MS (M + H)+ |
|---|---|---|
| 402 | 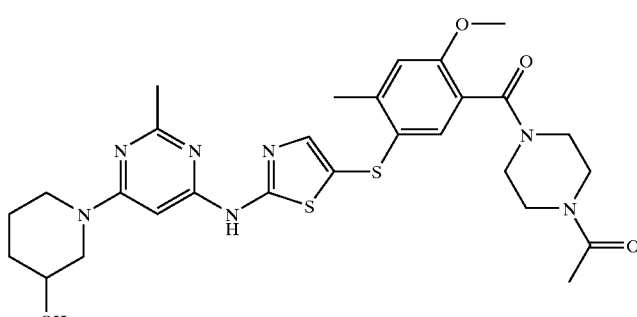 | 598.29 |
| 403 | 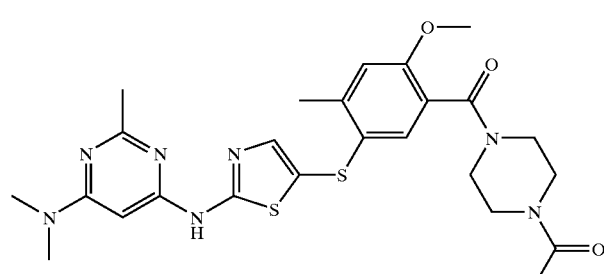 | 542.25 |
| 404 | 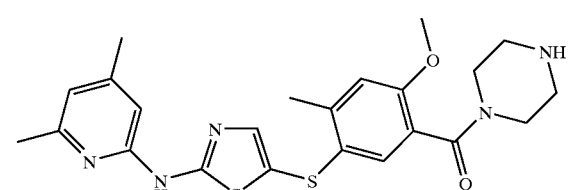 | 470.1 |
| 405 | 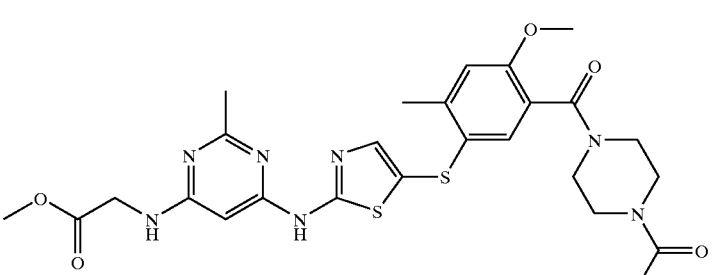 | 586.25 |
| 406 | 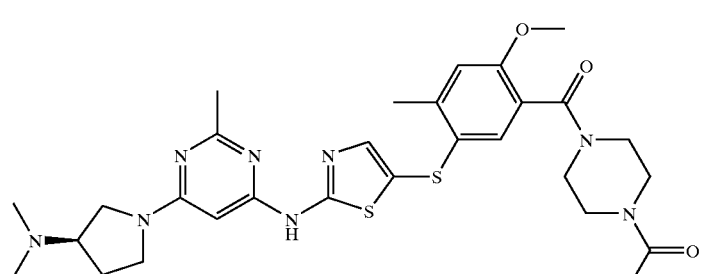 | 611.17 |

-continued

| Ex. No. | Structure | MS (M + H)+ |
|---|---|---|
| 407 | 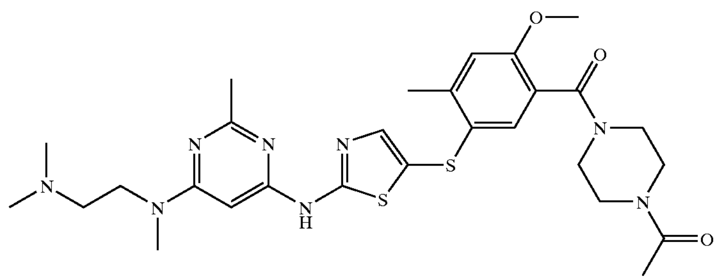 | 599.62 |
| 408 | 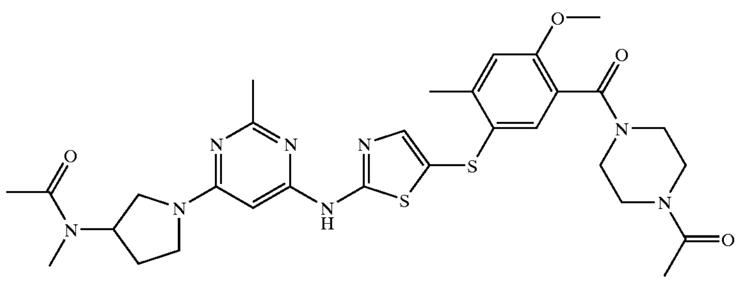 | 639.29 |
| 409 | 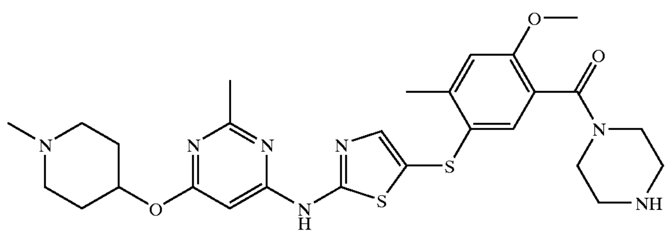 | 570.23 |
| 410 | 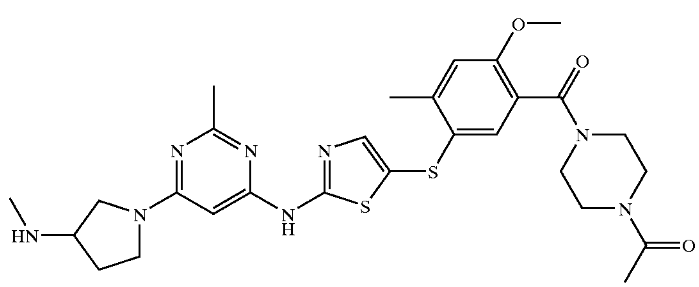 | 597.25 |
| 411 | 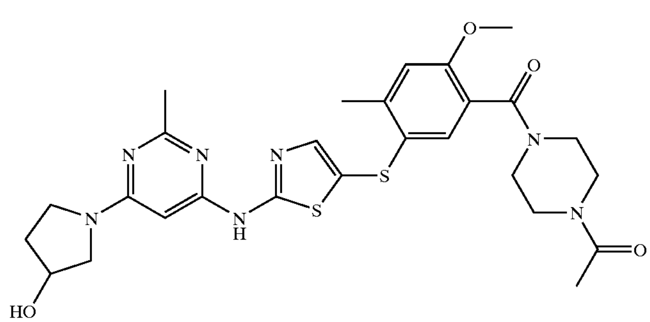 | 585.24 |

-continued

| Ex. No. | Structure | MS (M + H)+ |
|---|---|---|
| 412 | 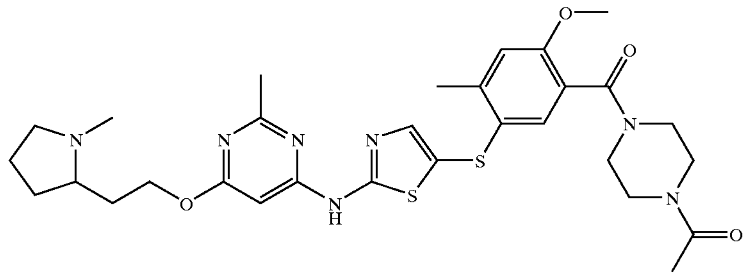 | 626.31 |
| 413 | 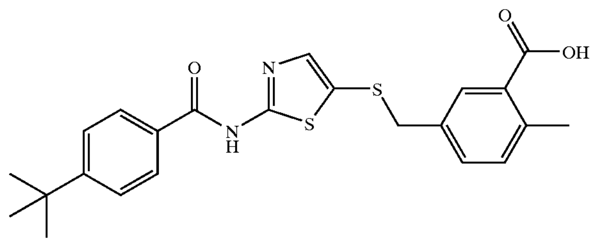 | 441.3 |
| 414 | 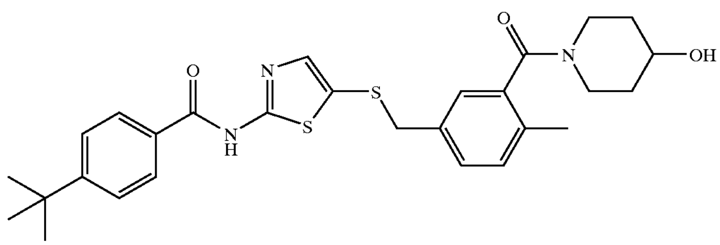 | 524.34 |
| 415 | 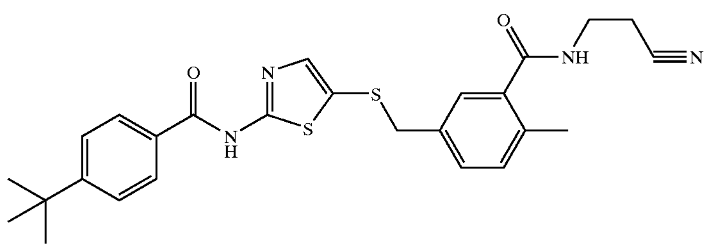 | 493.34 |
| 416 | 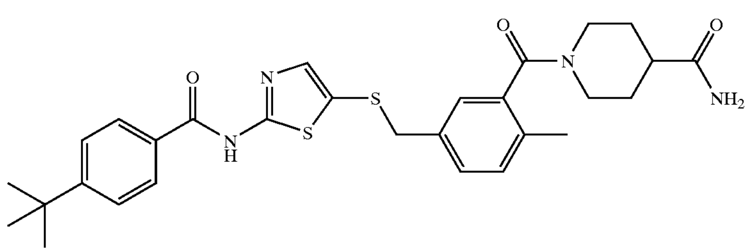 | 551.35 |
| 417 | 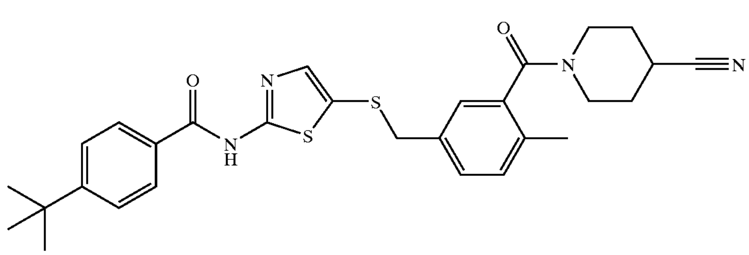 | 533.33 |

-continued

| Ex. No. | Structure | MS (M + H)+ |
|---|---|---|
| 418 | 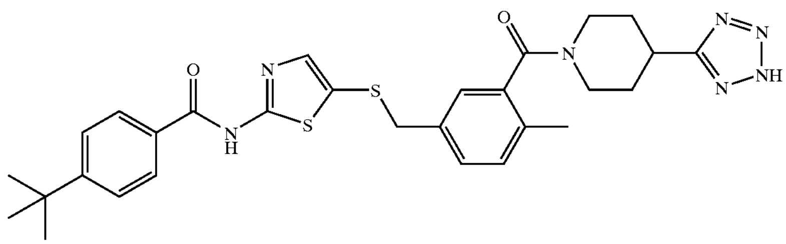 | 576.35 |
| 419 | 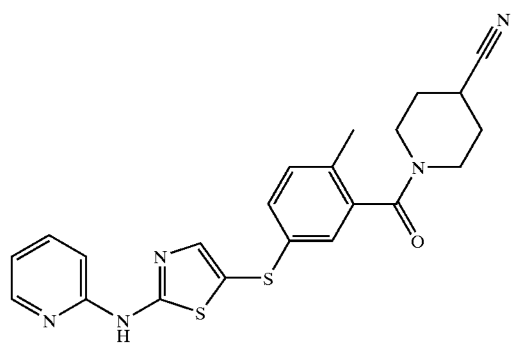 | 436.37 |
| 420 | 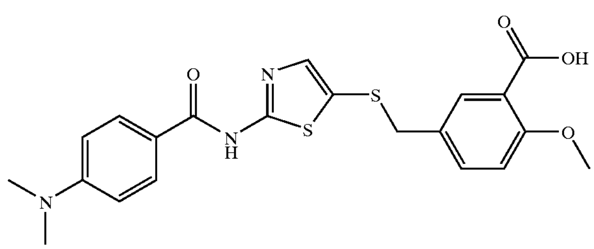 | 444.34 |
| 421 | 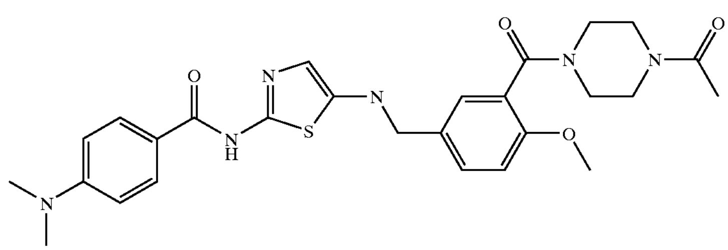 | 554.35 |
| 422 | 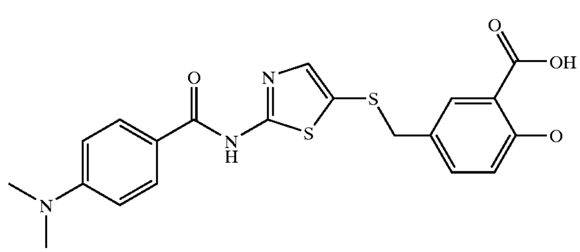 | 430.32 |

-continued

| Ex. No. | Structure | MS (M + H)+ |
|---|---|---|
| 423 | 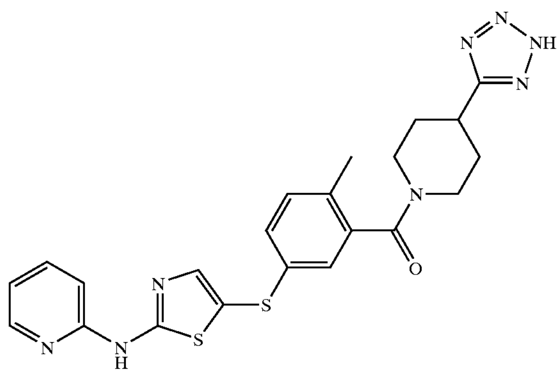 | 479.37 |
| 424 | 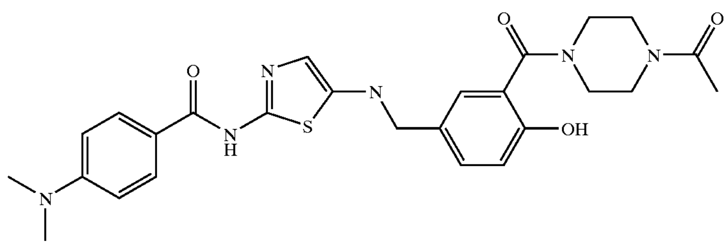 | 540.32 |
| 425 | 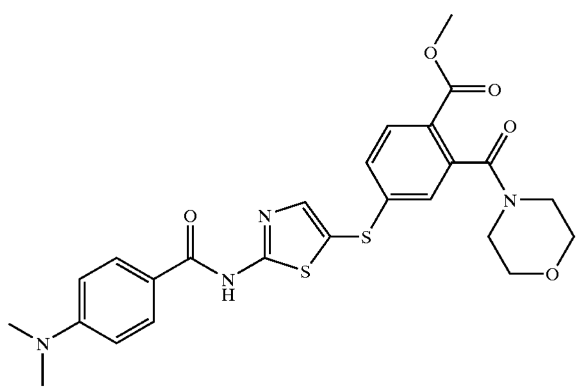 | 527.09 |
| 426 | 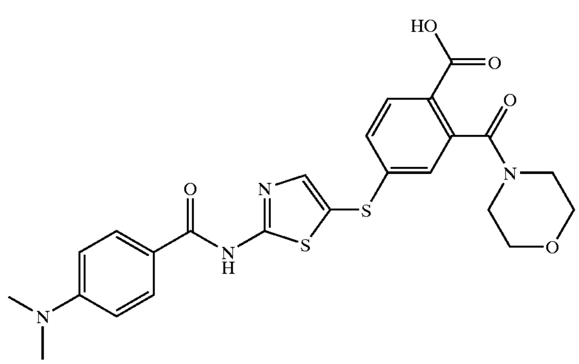 | 513.5 |

-continued

| Ex. No. | Structure | MS (M + H)+ |
|---|---|---|
| 427 | 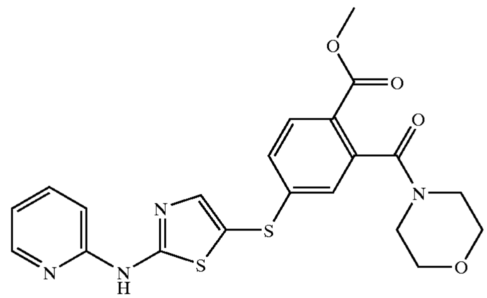 | 457.06 |
| 428 | 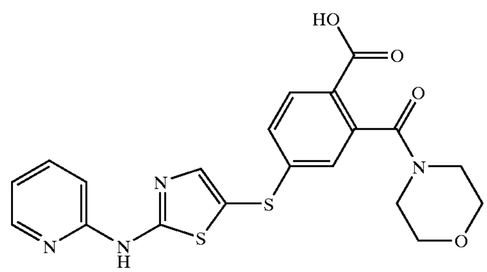 | 443.49 |
| 429 | 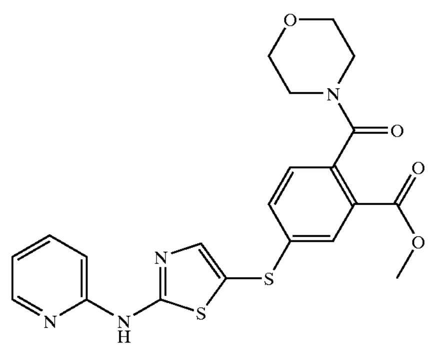 | 457.44 |
| 430 | 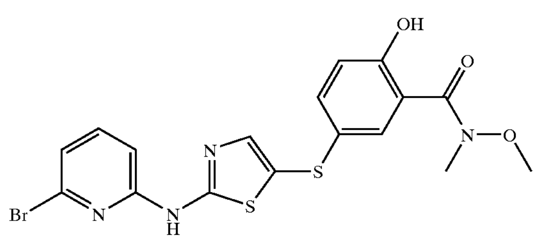 | 467.30<br>469.30 |
| 431 | 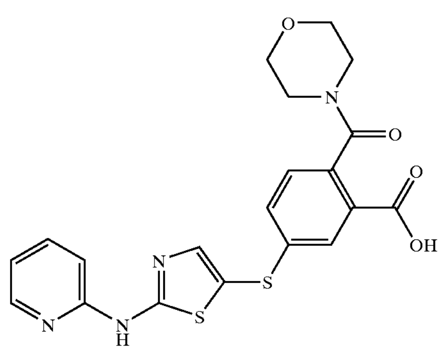 | 443.31 |

-continued

| Ex. No. | Structure | MS (M + H)+ |
|---|---|---|
| 432 | 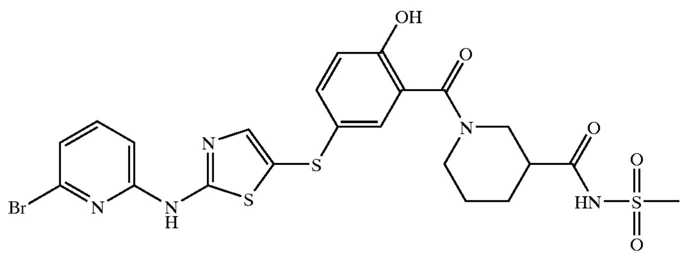 | 612.18 614.18 |
| 433 | 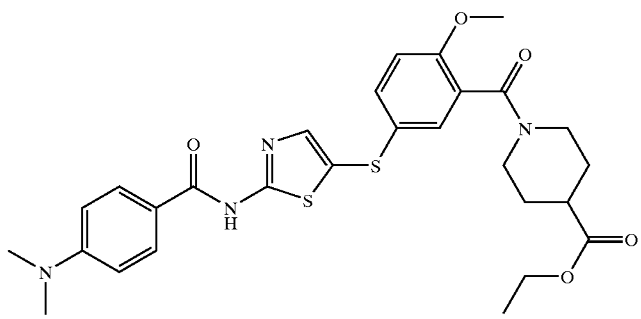 | 569.42 |
| 434 | 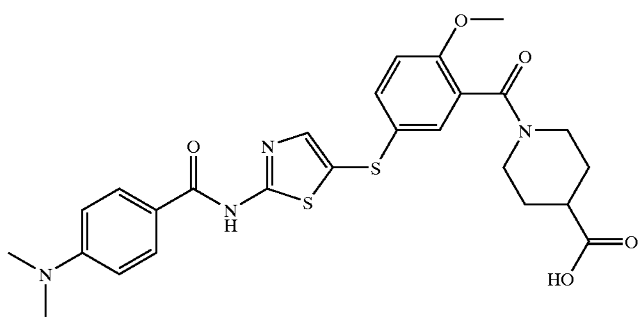 | 541.4 |
| 435 | 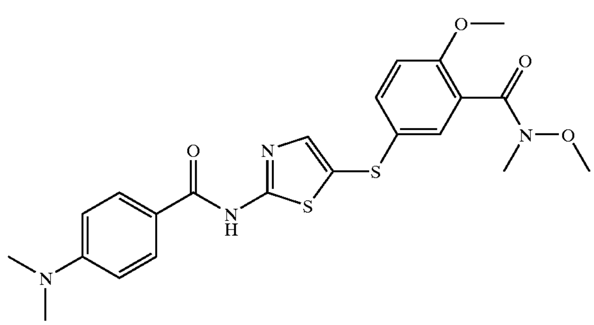 | 473.45 |

-continued

| Ex. No. | Structure | MS (M + H)+ |
|---|---|---|
| 436 | 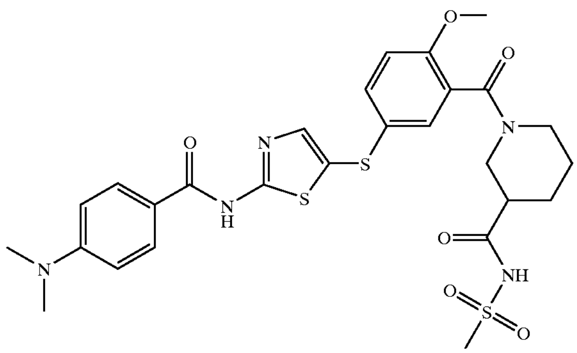 | 618.06 |
| 437 | 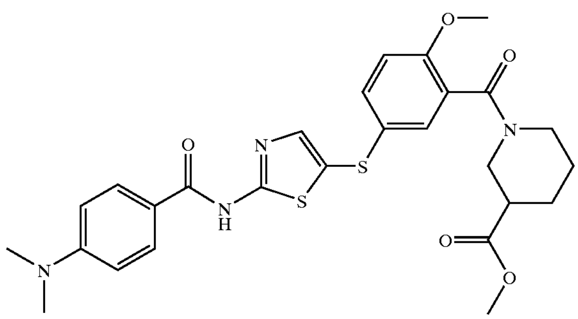 | 569.4 |
| 438 | 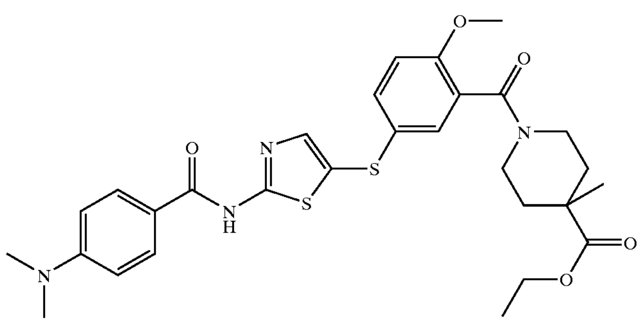 | 583.4 |
| 439 | 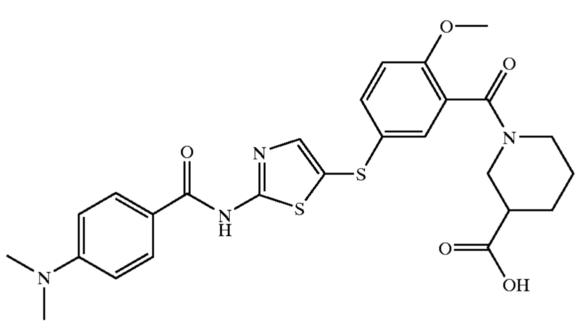 | 555.1 |

-continued
| Ex. No. | Structure | MS (M + H)+ |
|---|---|---|
| 440 | 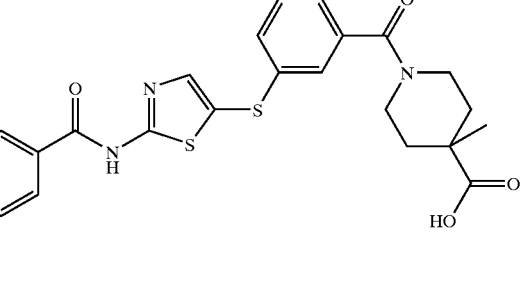 | 555.1 |
| 441 | 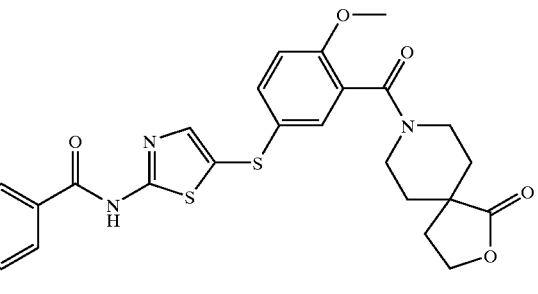 | 567.29 |
| 442 | 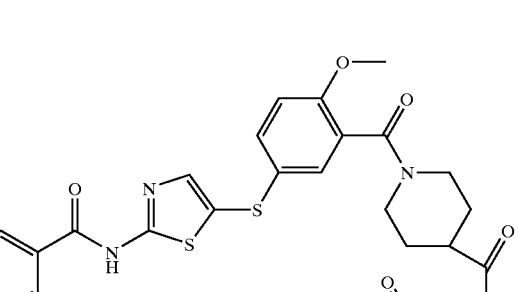 | 638.31 |
| 443 | 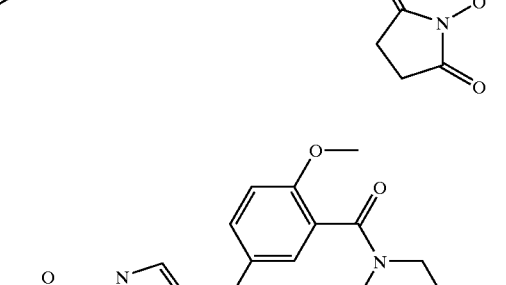 | 570.3 |

-continued

| Ex. No. | Structure | MS (M + H)+ |
|---|---|---|
| 444 | 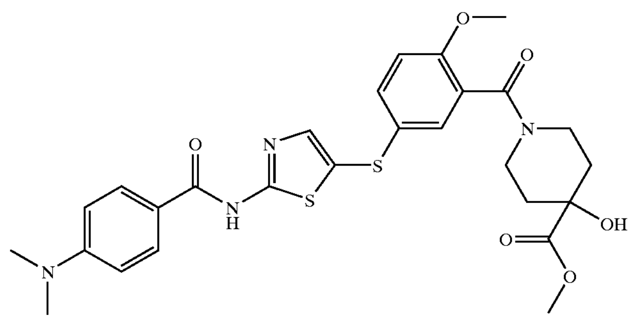 | 571.28 |
| 445 | 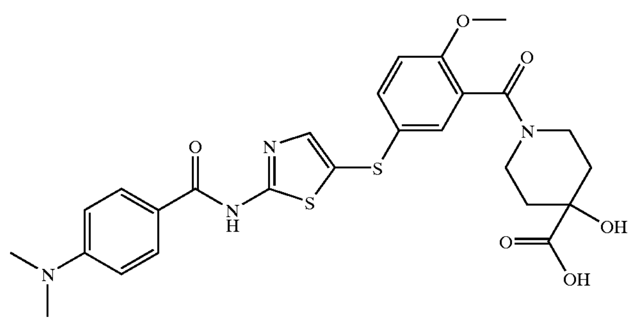 | 557.33 |
| 446 | 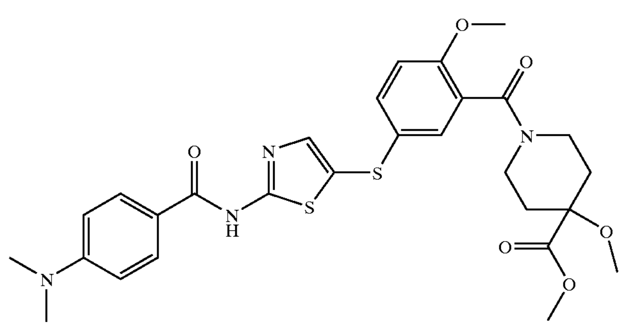 | 585.39 |
| 447 | 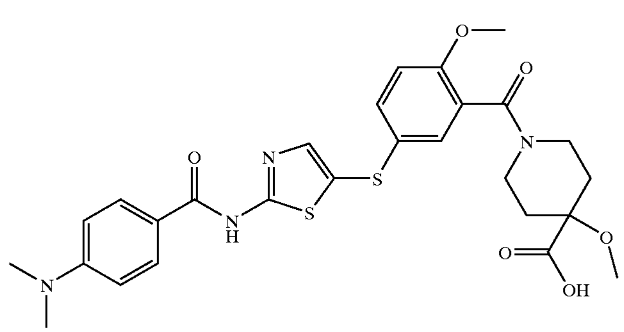 | 571.27 |

-continued

| Ex. No. | Structure | MS (M + H)+ |
|---|---|---|
| 448 | 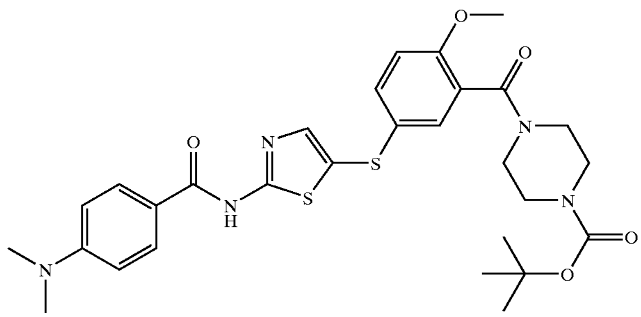 | 598.15 |
| 449 | 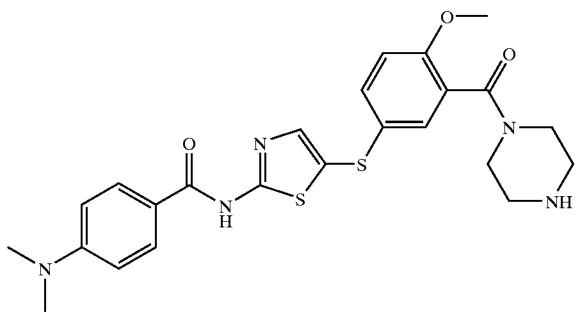 | 498.19 |
| 450 | 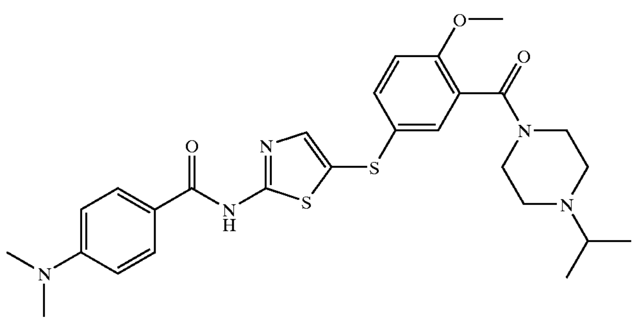 | 540.19 |
| 451 | 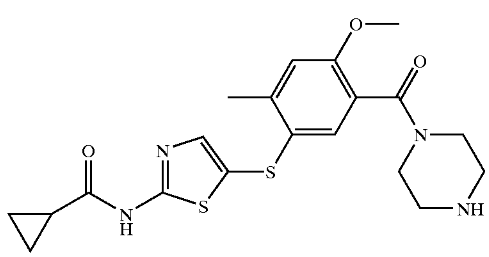 | 433.56 |
| 452 | 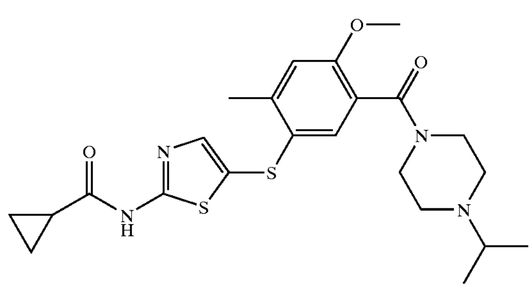 | 475.27 |

| Ex. No. | Structure | MS (M + H)+ |
|---|---|---|
| 453 | 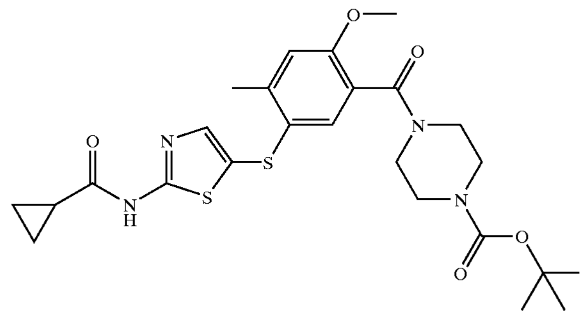 | 533.56 |
| 454 | 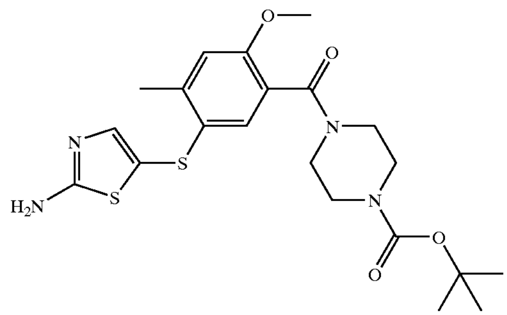 | 465.59 |
| 455 | 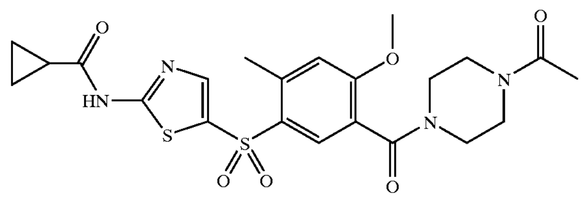 | 507.24 |

We claim:

1. A compound of formula I

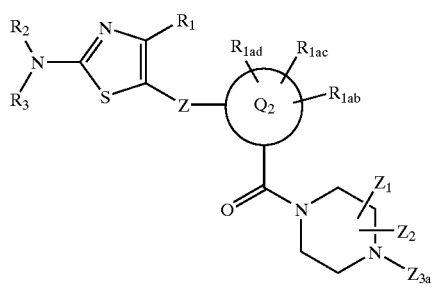

diastereomers, enantiomers or salts thereof
where $Q_2$ is phenyl;

Z is
- (1) —O—,
- (2) —S—,
- (3) —$CR_4R_5$—,
- (4) —$CR_4R_5$—O—$CR_{4a}R_{5a}$—,
- (5) —$CR_4R_5$—$NR_{4b}$—$CR_{4a}R_{5a}$—, or
- (6) —S—$CR_4R_5$—, $R_1$, $R_{1ab}$, $R_{1ac}$ and $R_{1ad}$ are independently
- (1) hydrogen or $R_6$,
- (2) —OH or —$OR_6$,
- (3) —$C(O)_qH$ or —$C(O)_qR_6$, where q is 1 or 2,
- (4) halo,
- (5) -$Z_4$-$NR_7R_8$, $R_2$ and $R_3$ are each independently H or -$Z_4$-$R_{6a}$;

$R_6$, $R_{6a}$, and $R_{6b}$ are independently alkyl, cycloalkyl, aryl, or aralkyl, each of which is unsubstituted or substituted with $Z_1$, $Z_2$ and one or more groups $Z_3$;

$R_4$, $R_{4a}$, $R_{4b}$, $R_5$ and $R_{5a}$ are each independently hydrogen, alkyl, aryl, aralkyl, or cycloalkyl;

$R_7$ and $R_8$ are each independently hydrogen or -$Z_4R_{6b}$;

$Z_{3a}$ is H, hydroxy, optionally substituted alkyl, —$OZ_6$, —C(O)H, —$C(O)_qZ_{6a}$, -$Z_4$-$NZ_7Z_8$, or -$Z_4$-$N(Z_{10})$-$Z_5$-$Z_6$;

$Z_1$, $Z_2$ and $Z_3$ are each independently
- (1) hydrogen or Z,
- (2) —OH or —$OZ_6$,
- (3) —$C(O)_qH$ or —$C(O)_qZ_6$,
- (4) halo,
- (5) -$Z_4$-$NZ_7Z_8$,
- (6) -$Z_4$-$N(Z_{10})$-$Z_5$-$Z_6$,
- (7) -$Z_4$-$N(Z_{10})$-$Z_5$-H,
- (8) oxo;

$Z_4$ and $Z_5$ are independently
(1) a single bond;
(2) —C(O)—;
(3) —S(O)$_q$—; or
(4) alkyl;

$Z_6$ and $Z_{6a}$ are independently
(i) alkyl, hydroxyalkyl, alkoxyalkyl, cycloalkyl, aryl, or aralkyl;
(ii) a group (i) which is itself substituted by one or more of the same or different groups (i); or
(iii) a group (i) or (ii) which is independently substituted by one or more of the groups (2) to (8) of the definition of $Z_1$;

$Z_7$, $Z_8$ and $Z_{10}$ are each independently hydrogen or -$Z_4$-$Z_{6a}$;

provided that said compound is other than a compound of formula I where
$Q_2$ is phenyl;
Z is —S—;
$R_1$ is hydrogen or $R_6$;
$R_{1ab}$ and $R_{1ac}$ are independently hydrogen, $R_6$ or —OR$_6$;
$R_{1ad}$ is hydrogen;
one of $R_2$ or $R_3$ is hydrogen or alkyl and the other $R_2$ or $R_3$ is -$Z_4$-$R_{6a}$, where:
$Z_4$ is —C(O)— and $R_{6a}$ is phenyl substituted with $Z_3$;
$R_6$ is alkyl;
$Z_{3a}$ is —C(O)$_q$Z$_{6a}$, where q is 1;
$Z_1$ and $Z_2$ are hydrogen;
$Z_3$ is -$Z_4$-NZ$_7$Z$_8$, where $Z_4$ is alkyl;
$Z_{6a}$ is alkyl;
$Z_7$ and $Z_8$ are each independently hydrogen or -$Z_4$-$Z_{6a}$, where $Z_4$ is a single bond.

2. A compound of claim 1 where
Z is
(1) —O—,
(2) —S—,
(3) —CR$_4$R$_5$—,
(4) —S—CR$_4$R$_5$—,
$R_1$, $R_{1ab}$, $R_{1ac}$ and $R_{1ad}$ are independently hydrogen, $R_6$ or —OR$_6$;
$R_2$ and $R_3$ are each independently H or -$Z_4$-$R_{6a}$;
$R_6$ and $R_{6a}$ are independently alkyl, cycloalkyl, or aryl, each of which is unsubstituted or substituted with $Z_1$, $Z_2$ and one or more groups $Z_3$;
$R_4$ and $R_5$ are each independently hydrogen or alkyl;
$Z_{3a}$ is H, hydroxy, optionally substituted alkyl, or —C(O)$_q$Z$_{6a}$;
$Z_1$, $Z_2$ and $Z_3$ are each independently
(1) hydrogen or $Z_6$,
(2) —OH or —OZ$_6$, or
(3) —C(O)$_q$H or —C(O)$_q$Z$_6$;
$Z_4$ is
(1) a single bond; or
(2)—C(O)—;
$Z_6$ and $Z_{6a}$ are independently
(i) alkyl, cycloalkyl, or aryl;
(ii) a group (i) which is itself substituted by one or more of the same or different groups (i); or
(iii) a group (i) or (ii) which is independently substituted by one or more of the groups (2) to (3) of the definition of $Z_1$.

3. A compound of claim 2 where
Z is
(1) —S—,
(2) —S—CR$_4$R$_5$—,
$R_1$, $R_{1ab}$, $R_{1ac}$ and $R_{1ad}$ are independently hydrogen, $R_6$ or —OR$_6$;
$R_2$ and $R_3$ are each independently H or -$Z_4$-$R_{6a}$;
$R_6$ and $R_{6a}$ are independently alkyl or aryl, each of which is unsubstituted or substituted with $Z_1$, $Z_2$ and one or more groups $Z_3$;
$R_4$ and $R_5$ are each independently hydrogen or alkyl;
$Z_{3a}$ is H, optionally substituted alkyl, or —C(O)$_q$Z$_{6a}$;
$Z_1$, $Z_2$ and $Z_3$ are each independently
(1) hydrogen or $Z_6$,
(2) —OH or —OZ$_6$, or
(3) —C(O)$_q$H or —C(O)$_q$Z$_6$;
$Z_4$ is
(1) a single bond; or
(2) —C(O)—;
$Z_6$ and $Z_{6a}$ are independently
(i) alkyl, cycloalkyl, or aryl;
(ii) a group (i) which is itself substituted by one or more of the same or different groups (i); or
(iii) a group (i) or (ii) which is independently substituted by one or more of the groups (2) to (3) of the definition of $Z_1$.

4. A compound of claim 3 where
Z is
(1) —S—,
(2) —S—CR$_4$R$_5$—,
$R_1$, $R_{1ab}$, $R_{1ac}$ and $R_{1ad}$ are independently hydrogen, $R_6$ or —OR$_6$;
$R_2$ is H;
$R_3$ is -$Z_4$-$R_{6a}$;
$R_6$ and $R_{6a}$ are independently alkyl or aryl, each of which is unsubstituted or substituted with $Z_1$, $Z_2$ and one or more groups $Z_3$;
$R_4$ and $R_5$ are each independently hydrogen;
$Z_{3a}$ is optionally substituted alkyl or —C(O)$_q$Z$_{6a}$;
$Z_1$, $Z_2$ and $Z_3$ are each independently hydrogen, $Z_6$ or —OZ$_6$;
$Z_4$ is —C(O)—;
$Z_6$ and $Z_{6a}$ are independently alkyl, cycloalkyl, or aryl.

5. A compound of claim 4 where
Z is —S—,
$R_{6a}$ is aryl, which is unsubstituted or substituted with $Z_1$, $Z_2$ and one or more groups $Z_3$; $Z_1$, $Z_2$ and $Z_3$ are each independently hydrogen, $Z_6$ or —OZ$_6$;
$Z_6$ is alkyl.

6. A compound of claim 1 having the formula

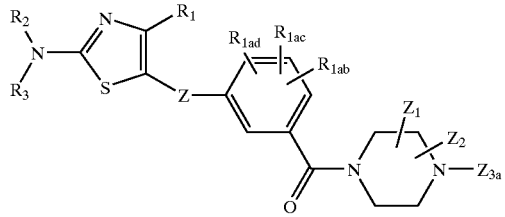

wherein $R_1$, $R_2$, $R_3$, Z, $R_{1ad}$, $R_{1ab}$, $R_{1ac}$, $Z_1$, $Z_2$ and $Z_{3a}$ are as defined in claim 1.

7. A compound of claim 6 where
R$_2$ is H or alkyl; and
R$_3$ is -Z$_4$-R$_{6a}$, where:
  Z$_4$ is —C(O)— and R$_{6a}$ is
    (1) aryl optionally substituted with one or more Z$_1$, Z$_2$ or Z$_3$; or
    (2) cycloalkyl optionally substituted with one or more Z$_1$, Z$_2$ or Z$_3$.

8. A compound of claim 7 wherein R$_1$, R$_{1ab}$, R$_{1ac}$ and R$_{1ad}$ are independently H, alkyl, hydroxy, halo, —OR$_6$, or —NR$_7$R$_8$.

9. A compound of claim 8 wherein at least one of R$_{1ab}$, R$_{1ac}$ and R$_{1ad}$ is other than H.

10. A compound of claim 6 having the following formula

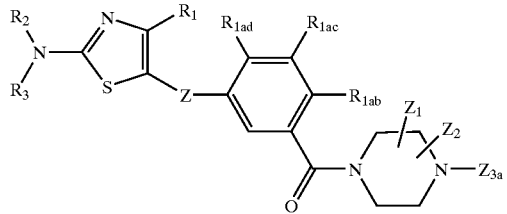

where one of R$_{1ab}$, R$_{1ac}$ and R$_{1ad}$ is H and the other two are independently alkyl, hydroxy, halo, —OR$_6$, or —NR$_7$R$_8$.

11. A compound of claim 10 wherein one of R$_{1ab}$, R$_{1ac}$ and R$_{1ad}$ is H and the other two are independently alkyl or —OR$_6$.

12. A compound of claim 11 wherein Z is —S— and R$_{1ac}$ is H.

13. A compound of claim 11 wherein Z is —S—CR$_4$R$_5$—, and R$_{1ad}$ is H.

14. A compound of claim 10 where Z$_{3a}$ is —C(O)-alkyl.

15. A pharmaceutical composition comprising at least one compound of claim 1 and a pharmaceutically acceptable vehicle or carrier therefor.

16. A pharmaceutical composition of claim 15 further comprising at least one additional therapeutic agent selected from anti-inflammatory agents, anti-proliferative agents, anti-cancer agents or anti-cytotoxic agents.

17. A pharmaceutical composition of claim 16 wherein the additional therapeutic agents are selected from steroids, mycophenolate mofetil, LTD$_4$ inhibitors, CTLA4-Ig, LEA-29Y, phosphodiesterase inhibitors, antihistamines, or p$^{38}$ MAPK inhibitors.

* * * * *

UNITED STATES PATENT AND TRADEMARK OFFICE
CERTIFICATE OF CORRECTION

| | | |
|---|---|---|
| PATENT NO. | : 6,958,336 B2 | Page 1 of 1 |
| APPLICATION NO. | : 10/641933 | |
| DATED | : October 25, 2005 | |
| INVENTOR(S) | : Barrish et al. | |

It is certified that error appears in the above-identified patent and that said Letters Patent is hereby corrected as shown below:

Column 216, Line 59 "(1) hydrogen or Z," should read:

-- (1) hydrogen or $Z_6$, --

Signed and Sealed this

Third Day of July, 2007

JON W. DUDAS
*Director of the United States Patent and Trademark Office*